(12) United States Patent
Muir et al.

(10) Patent No.: US 10,087,485 B2
(45) Date of Patent: Oct. 2, 2018

(54) DNA BARCODING OF DESIGNER MONONUCLEOSOME AND CHROMATIN ARRAY LIBRARIES FOR THE PROFILING OF CHROMATIN READERS, WRITERS, ERASERS, AND MODULATORS THEREOF

(71) Applicant: The Trustees of Princeton University, Princeton, NJ (US)

(72) Inventors: Tom W. Muir, Princeton, NJ (US); Uyen T. T. Nguyen, Princeton, NJ (US); Manuel M. Mueller, Princeton, NJ (US)

(73) Assignee: The Trustees of Princeton University, Princeton, NJ (US)

(*) Notice: Subject to any disclaimer, the term of this patent is extended or adjusted under 35 U.S.C. 154(b) by 459 days.

(21) Appl. No.: 14/405,303

(22) PCT Filed: Jun. 6, 2013

(86) PCT No.: PCT/US2013/044537
§ 371 (c)(1),
(2) Date: Dec. 3, 2014

(87) PCT Pub. No.: WO2013/184930
PCT Pub. Date: Dec. 12, 2013

(65) Prior Publication Data
US 2015/0197801 A1     Jul. 16, 2015

Related U.S. Application Data

(60) Provisional application No. 61/656,233, filed on Jun. 6, 2012, provisional application No. 61/712,148, filed on Oct. 10, 2012.

(51) Int. Cl.
*C40B 20/04* (2006.01)
*C12Q 1/6876* (2018.01)
(Continued)

(52) U.S. Cl.
CPC ....... *C12Q 1/6876* (2013.01); *C12N 15/1065* (2013.01); *C12Q 1/48* (2013.01);
(Continued)

(58) Field of Classification Search
None
See application file for complete search history.

(56) References Cited

U.S. PATENT DOCUMENTS

| 5,972,608 A | 10/1999 | Peterson et al. |
| 8,354,231 B2 | 1/2013 | Kwong et al. |

(Continued)

FOREIGN PATENT DOCUMENTS

| WO | WO 2012/019765 A1 | 2/2012 |
| WO | WO-2012/050963 A2 | 4/2012 |
| WO | WO-2013/030579 A1 | 3/2013 |

OTHER PUBLICATIONS

Bartke et al. (2010) "Nucleosome-Interacting Proteins Regulated by DNA and Histone Methylation" Cell 143(3):470-484.*
(Continued)

*Primary Examiner* — Karen S. Weiler
(74) *Attorney, Agent, or Firm* — Panitch Schwarze Belisario & Nadel LLP; Lars H. Genieser

(57) ABSTRACT

Compositions and methods are provided for DNA barcoding of designer mononucleosome and polynucleosome (chromatin array) libraries for use, for example, for the profiling of chromatin readers, writers, erasers, and modulators thereof.

19 Claims, 22 Drawing Sheets

Specification includes a Sequence Listing.

(51) Int. Cl.
    C12Q 1/48      (2006.01)
    G01N 33/68     (2006.01)
    C40B 30/08     (2006.01)
    C40B 30/04     (2006.01)
    C12N 15/10     (2006.01)
(52) U.S. Cl.
    CPC .............. *C40B 20/04* (2013.01); *C40B 30/04* (2013.01); *C40B 30/08* (2013.01); *G01N 33/6875* (2013.01)

(56) References Cited

U.S. PATENT DOCUMENTS

| | | | |
|---|---|---|---|
| 2002/0081638 A1* | 6/2002 | Jenuwein | C07K 16/40 435/7.23 |
| 2003/0082668 A1* | 5/2003 | Tamai | C12Q 1/34 435/24 |
| 2007/0161031 A1 | 7/2007 | Trinklein et al. | |
| 2007/0274912 A1 | 11/2007 | Allis et al. | |
| 2009/0062130 A1 | 3/2009 | Steinman et al. | |
| 2010/0184611 A1 | 7/2010 | Neri et al. | |
| 2010/0279898 A1 | 11/2010 | Li et al. | |

OTHER PUBLICATIONS

Nikolov et al. (2011) "Chromatin Affinity Purification and Quantitative Mass Spectrometry Defining the Interactome of Histone Modification Patterns" Molecular and Cellular Proteomics 10(11):M110. 005371.*
Dorigo et al. (2003) "Chromatin Fiber Folding: Requirement for the Histone H4 N-terminal Tail" J. Mol. Biol. 327(1):85-96.*
Agasti et al., (2012). Photocleavable DNA Barcode-Antibody Conjugates Allow Sensitive and Multiplexed Protein Analysis in Single Cells. *Journal of the American Chemical Society*, 134(45), 18499-18502. doi:10.1021/ja307689w.
Al-Sady et al., "Division of Labor between the Chromodomains of HP1 and Suv39 Methylase Enables Coordination of Heterochromatin Spread," Molecular Cell 51, 80-91, Jul. 2013.
Allis et al., (2011). Spreading chromatin into chemical biology. *Chembiochem : a European journal of chemical biology*, 12(2), 264-279. doi:10.1002/cbic.201000761.
Blacketer et al., (2010). Nucleosome interactions and stability in an ordered nucleosome array model system. *The Journal of biological chemistry*, 285(45), 34597-34607. doi:10.1074/jbc.M110.140061.
Britton et al., (2011). Breaking the histone code with quantitative mass spectrometry. *Expert review of proteomics*, 8(5), 631-643. doi:10.1586/epr.11.47.
Buller et al., (2010). Drug discovery with DNA-encoded chemical libraries. *Bioconjugate* 21(9), pp. 1571-1580.
Clark, M. A. (2010). Selecting chemicals: the emerging utility of DNA-encoded libraries. *Current Opinion in Chemical Biology*, 14(3), 396-403. doi:10.1016/j.cbpa.2010.02.017.
Dawson et al., (2000). Synthesis of native proteins by chemical ligation. *Annual Review of Biochemistry*, 69, 923-960. doi:10.1146/annurev.biochem.69.1.923.
Dignam et al., (1983). Accurate transcription initiation by RNA polymerase II in a soluble extract from isolated mammalian nuclei. *Nucleic Acids Research* Mar. 11, 1983; 11(5): 1475-1489.
Dyer et al., (2004). Reconstitution of nucleosome core particles from recombinant histones and DNA. *Methods in enzymology*, 375, 23-44.
Encode Project Consortium, Dunham et al. (2012). An integrated encyclopedia of DNA elements in the human genome. Nature, 489(7414), 57-74. doi:10.1038/nature11247.
Fierz et al., (2011). Histone H2B ubiquitylation disrupts local and higher-order chromatin compaction. Nature chemical biology, 7(2), 113-119. doi:10.1038/nchembio.501.

Fierz et al., (2012). Chromatin as an expansive canvas for chemical biology. Nature chemical biology, 8(5), 417-427. doi:10.1038/nchembio.938.
Fierz et al., (2012). Stability of Nucleosomes Containing Homogenously Ubiquitylated H2A and H2B Prepared Using Semisynthesis. Journal of the American Chemical Society, 134(48), 19548-19551. doi:10. 1021/ja308908p.
Garske et al., (2010). Combinatorial profiling of chromatin binding modules reveals multisite discrimination. Nature Methods, 6(4), 283-290. doi:10.1038/nchembio.319.
Goldman et al., (2010). Chromatin remodeling by imitation switch (ISWI) class ATP-dependent remodelers is stimulated by histone variant H2A.Z. The Journal of biological chemistry, 285(7), 4645-4651. doi:10.1074/jbc.M109.072348.
Grzybowski et al., "Calibrating ChIP-Seq with Nucleosomal Internal Standards to Measure Histone Modification Density Genome Wide," Molecular Cell 58, 886-899, Jun. 4, 2015.
Heller, M. J. (2002). DNA microarray technology: devices, systems, and applications. *Annual review of biomedical engineering*, 4, 129-153. doi:10.1146/annurev.bioeng.4.020702.153438.
Kleer et al., (2003). EZH2 is a marker of aggressive breast cancer and promotes neoplastic transformation of breast epithelial cells. *Proceedings of the National Academy of Sciences*, 100(20), 11606-11611. doi:10.1073/pnas.1933744100.
Kleiner et al., (2011). Small-molecule discovery from DNA-encoded chemical libraries. *Chemical Society Reviews* 2011,40, 5707-5717.
Krutzik et al., (2006). Fluorescent cell barcoding in flow cytometry allows high-throughput drug screening and signaling profiling. Nature Methods, 3(5), 361-368. doi:10.1038/nmeth872.
Li et al., (2011). A Direct Method for Site-Specific Protein Acetylation. Angewandte Chemie vol. 50, Issue 41, pp. 9611-9614, Oct. 4, 2011.
Lowary et al., (1998). New DNA sequence rules for high affinity binding to histone octamer and sequence-directed nucleosome positioning. Journal of Molecular Biology, 276(1), 19-42. doi:10.1006/jmbi.1997.1494.
Mardis, E. R. (2008). Next-generation DNA sequencing methods. Annual review of genomics and human genetics, 9, 387-402. doi:10.1146/annurev.genom.9.081307.164359.
Merriman et al., (2012). Progress in Ion Torrent semiconductor chip based sequencing. Electrophoresis, 33(23), 3397-3417. doi:10.1002/elps.201200424.
Muir, T. W. (2003). Semi synthesis of proteins by expressed protein ligation. Annual Review of Biochemistry, 72, 249-289. doi:10.1146/annurev.biochem.72.121801.161900.
Rothberg et al., (2011). An integrated semiconductor device enabling non-optical genome sequencing. Nature, 475(7356), 348-352. doi:10. 1038/nature10242.
Schones et al., (2008). Genome-wide approaches to studying chromatin modifications. Nature reviews. Genetics, 9(3), 179-191. doi:10. 1038/nrg2270.
Simon et al., (2007). The site-specific installation of methyl-lysine analogs into recombinant histones. Cell, 128(5), 1003-1012. doi:10. 1016/j.cell.2006.12.041.
Spacil et al., (2013). High-throughput assay of 9 lysosomal enzymes for newborn screening. Clinical chemistry, 59(3), 502-511. doi:10. 1373/clinchem.2012.189936.
Wang et al., (2006). Expanding the genetic code. Annual review of biophysics and biomolecular structur, Annu Rev Biophys Biomol Struct. 2006;35:225-49.
Weibel et al., (2006). Applications of microfluidics in chemical biology. Current Opinion in Chemical Biolog, vol. 10, Issue 6, pp. 584-591.
Whitesides, G. M. (2006). The origins and the future of microfluidics. Nature, 442(7101), 368-373. doi:10.1038/nature05058.
Supplementary European Search Report and Opinion in European Patent Application No. 13800410.6, dated Apr. 11, 2016.
Myrriah S Chavez et al. "The conformational flexibility of the C-terminus of histone H4 promotes histone octamer and nucleosome stability and yeast viability", Epigenetics & Chromatin, Apr. 27, 2012, vol. 5, No. 1, p. 5 (pp. 1-20) Biomed Central LTD, London, UK.

(56) References Cited

OTHER PUBLICATIONS

Shima Nakanishi et al. "A comprehensive library of histone mutants identifies nucleosomal residues required for H3K4 methylation", Nature Structural and Molecular Biology, Aug. 2008, pp. 881-888, vol. 15, No. 8.

H. Huang et al. "HistoneHits: A database for histone mutations and their phenotypes", Genome Research, Feb. 13, 2009, pp. 674-681, vol. 19, No. 4.

Clayton K. Collings et al. "Oligonucleotide Sequence Motifs as Nucleosome Positioning Signals", PLoS ONE, Jun. 3, 2010, p. e10933 (pp. 1-18), vol. 5, No. 6.

R.B. Deal et al. "Genome-wide Kinetics of Nucleosome Turnover Determined by Metabolic Labeling of Histones", Science, May 28, 2010, pp. 1161-1164, vol. 328, No. 5982.

International Search Report and Written Opinion in International Application No. PCT/US13/44537, dated Aug. 18, 2014.

U.T.T. Nguyen et al. "Accelerated chromatin biochemistry using DNA-barcoded nucleosome libraries", Nature Methods, vol. 11, No. 8 (Aug. 2014) pp. 834-840 and Online Methods (8 pages) (doi:10.1038/nmeth.3022).

J. Dai et al. "Probing Nucleosome Function: A Highly Versatile Library of Synthetic Histone H3 and H4 Mutants", Cell, vol. 134, No. 6 (Sep. 19, 2008) pp. 1066-1078 and Supplemental Data (12 pages) (doi:10.1016/j.cell.2008.07.019).

A.J. Ruthenburg et al. "Recognition of a Mononucleosomal Histone Modification Pattern by BPTF via Multivalent Interactions", Cell, vol. 145, No. 5 (May 2011) pp. 692-706 and Supplemental Information (pp. S1-S20) (doi:10.1016/j.cell.2011.03.053).

J.L. Birch et al. "FACT facilitates chromatin transcription by RNA polymerases I and III", The EMBO Journal, vol. 28, No. 7 (Feb. 12, 2009) pp. 854-865 and Supplementary Information (12 pages).

A.Flaus et al. "Positioning and Stability of Nucleosomes on MMTV 3'LTR Sequences", J. Mol. Biol., vol. 275, No. 3 (Jan. 23, 1998) pp. 427-441.

Dai et al., "Probing Nucleosome Function: A Highly Versatile Library of Syntheric Histone H3 and H4 Mutants", Cell, vol. 134, No. 6, pp. 1066-1078. (2008).

Verzijlbergen, et al., "A Barcode Screen for Epigenetic Regulators Reveals a Role for the NuB4/HAT-B Histone Acetyltranserase Complex in Histone Turnover", PLOS Genetics, vol. 7, No. 10, pp. 1-15. (2011).

Ruthenburg et al., "Recognition of a Mononucleosomal Histone Modification Pattern by BPTF Via Multivalent Interactions", Cell, vol. 145, No. 5, pp. 1-15. (2011).

Kato et al., "Biochemical Screening of Stable Dinucleosomes Using DNA Fragments From a Dinucleosome DNA Library", Journal of Molecular Biology, vol. 350, No. 2, pp. 215-227. (2005).

Birch et al., "FACT Facilities Chromatin Transcription by RNA Polymerases I and III", The EMBO Journal, vol. 28, No. 7, pgs. (2009).

Carey et al., "Studying Chromatin Dynamics in Vitro: Chromatin Assembly, Remodeling, and Transcription", In: Transcriptional Regulation Eukaryotes: Concepts, Strategies, and Techniques, Second Edition, Cold Spring Harbor Laboratory Press, Chapter 13, pp. 539-620. (2009).

Luger et al., "Preparation of Nucleosome Core Particle From Recombinant Histones", Methods in Enzymology, vol. 34, pp. 3-19. (1999).

Flaus et al., "Positioning and Stability of Nucleosomes on MMTV 3'LTR Sequences", Journal of Molecular Biology, vol. 275, No. 3, pp. 427-441. (1997).

* cited by examiner

| MN ID | H2A | H2B | H3 | H4 | MN barcode |
|---|---|---|---|---|---|
| 1 | wt | wt | wt | wt | AGTGCA |
| 2 | wt | wt | wt | K5ac | ATCATA |
| 3 | wt | wt | wt | K8ac | AGATAC |
| 4 | wt | wt | wt | K12ac | CGATGC |
| 5 | wt | wt | wt | K16ac | CTGTAT |
| 6 | wt | wt | wt | K20ac | AGATGT |
| 7 | wt | wt | wt | Kac$_5$ | CATATC |
| 8 | wt | wt | K4me3 | wt | CGTGTC |
| 9 | wt | wt | K4me3 | K5ac | ATCTGA |
| 10 | wt | wt | K4me3 | K8ac | TCACTC |
| 11 | wt | wt | K4me3 | K12ac | ATGTGC |
| 12 | wt | wt | K4me3 | K16ac | TCTGTA |
| 13 | wt | wt | K4me3 | K20ac | ATGACA |
| 14 | wt | wt | K4me3 | Kac$_5$ | CGATGT |
| 15 | wt | wt | K9me3 | wt | ACGCAC |
| 16 | wt | wt | K9me3 | K5ac | CGATGA |
| 17 | wt | wt | K9me3 | K8ac | TACACT |
| 18 | wt | wt | K9me3 | K12ac | CATACA |
| 19 | wt | wt | K9me3 | K16ac | CATCGC |
| 20 | wt | wt | K9me3 | K20ac | TCGTGA |
| 21 | wt | wt | K9me3 | Kac$_5$ | ATATCT |
| 22 | wt | wt | K27me3 | wt | ATCGAC |
| 23 | wt | wt | K27me3 | K5ac | CGTATC |
| 24 | wt | wt | K27me3 | K8ac | CTCTCA |
| 25 | wt | wt | K27me3 | K12ac | ACACGT |
| 26 | wt | wt | K27me3 | K16ac | CAGCTC |
| 27 | wt | wt | K27me3 | K20ac | TGCGCT |
| 28 | wt | wt | K27me3 | Kac$_5$ | CGTAGC |
| 29 | wt | wt | Kac$_5$ | wt | TGTATC |
| 30 | wt | ubH2B | wt | wt | ACATCT |
| 31 | wt | ubH2B | K4me3 | wt | AGATGA |
| 32 | wt | ubH2B | K9me3 | wt | CACATC |
| 33 | wt | ubH2B | K27me3 | wt | CGCGCA |
| 34 | wt | ubH2B | Kac$_5$ | wt | ACAGAC |
| 35 | wt | ubH2B | wt | Kac$_5$ | AGTACT |
| 36 | ubH2A | wt | wt | wt | TAGCGC |
| 37 | ubH2A | wt | K4me3 | wt | CTATCA |
| 38 | ubH2A | wt | K9me3 | wt | ATAGAC |
| 39 | ubH2A | wt | K27me3 | wt | TATGTC |

FIG. 12B

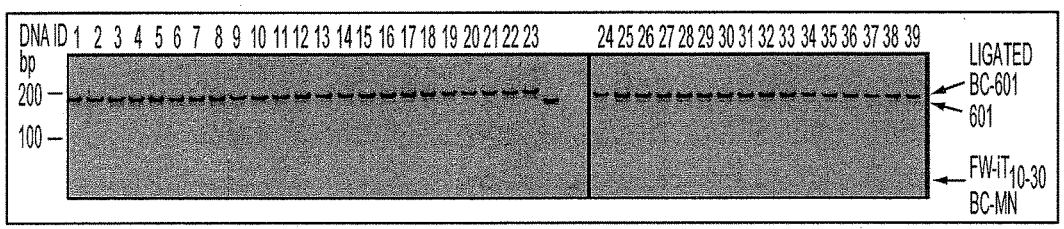

FIG. 12C

SEQUENCE LISTING

```
<160> NUMBER OF SEQ ID NOS: 57

<210> SEQ ID NO 1
<211> LENGTH: 4
<212> TYPE: PRT
<213> ORGANISM: Unknown
<220> FEATURE:
<223> OTHER INFORMATION: Description of Unknown: "PWWP" motif peptide

<400> SEQUENCE: 1

Pro Trp Trp Pro
1

<210> SEQ ID NO 2
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
accctaggtc tctgatgctg gagaatcccg gtgccgagg                               39

<210> SEQ ID NO 3
<211> LENGTH: 40
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 3
ctaccacatc gtgggatgta tatatctgac acgtgcctgg                              40

<210> SEQ ID NO 4
<211> LENGTH: 191
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
gatatcaccc taggtctctg atgctggaga atcccggtgc cgaggccgct caattggtcg       60
tagacagctc tagcaccgct taaacgcacg tacgcgctgt ccccgcgtt ttaaccgcca       120 aggggattac tccctagtct ccaggcacgt gtcagatata tacatcctgt cacgcggtga      180
acagcgatat c                                                            191

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(25)
<223> OTHER INFORMATION: a, c, t, g, unknown or other

<400> SEQUENCE: 5
cctgcgtgtc tccgactcag hnnnnh                                            26

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(9)
<223> OTHER INFORMATION: a, c, t, g, unknown or other

<400> SEQUENCE: 6
catcdnnnnd ctgagtcgga gacacgcagg aa                                     32

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: 5'-biotin

<400> SEQUENCE: 7
tatcacttgc aacagtccta acattcacct c                                      31

<210> SEQ ID NO 8
```

```
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
atccaaaaaa ctgtgccgca gtcgg                                            25

<210> SEQ ID NO 9
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(26)
<223> OTHER INFORMATION: a, c, t, g, unknown or other

<400> SEQUENCE: 9
cctgcgtgtc tccgactcag nnnnnngatg ctggagaatc ccggtgccga gg              52

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gtgacaggat gtatatatct gacacgtgcc tgg                                   33

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccatctcatc cctgcgtgtc tccgactcag                                       30

<210> SEQ ID NO 12
<211> LENGTH: 59
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (25)..(28)
<223> OTHER INFORMATION: a, c, t, g, unknown or other

<400> SEQUENCE: 12
cctctctatg ggcagtcggt gatbnnnndg gtgctagagc tgtctacgac caattgagc       59

<210> SEQ ID NO 13
<211> LENGTH: 152
<212> TYPE: DNA
<213> ORGANISM: Artificial Sequence
<220> FEATURE:
<223> OTHER INFORMATION: Description of Artificial Sequence: Synthetic
      polynucleotide
```

```
<220> FEATURE:
<223> OTHER INFORMATION: 5'-biotin

<400> SEQUENCE: 13
tatcacttgc aacagtccta acattcacct cttgtgtgtt tgtgtctgtt cgccatcccg      60
tctccgctcg tcacttatcc ttcactttcc agagggtccc cccgcagacc ccggcgaccc     120
tggtcggccg actgcggcac agttttttgg at                                   152

<210> SEQ ID NO 14
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ccatctcatc cctgcgtgtc tccgactcag atgcaggatg ctggagaatc ccggtgccga      60
gg                                                                     62

<210> SEQ ID NO 15
<211> LENGTH: 147
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
ctggagaatc ccggtgccga ggccgctcaa ttggtcgtag acagctctag caccgcttaa      60
acgcacgtac gcgctgtccc ccgcgtttta accgccaagg ggattactcc ctagtctcca    120
ggcacgtgtc agatatatac atcctgt                                        147

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
cctgcgtgtc tccgactcag                                                  20

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cctctctatg ggcagtcggt gat                                              23

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
```

```
ggtgctagag ctgtctacga ccaattgagc                                      30
```

<210> SEQ ID NO 19
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19

```
agtgca                                                                 6
```

<210> SEQ ID NO 20
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20

```
atcata                                                                 6
```

<210> SEQ ID NO 21
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21

```
agatac                                                                 6
```

<210> SEQ ID NO 22
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22

```
cgatgc                                                                 6
```

<210> SEQ ID NO 23
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23

```
ctgtat                                                                 6
```

<210> SEQ ID NO 24
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24 agatgt                                                                6

<210> SEQ ID NO 25
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25 catatc                                                                6

<210> SEQ ID NO 26
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26 cgtgtc                                                                6

<210> SEQ ID NO 27
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27 atctga                                                                6

<210> SEQ ID NO 28
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28 tcactc                                                                6

<210> SEQ ID NO 29
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29 atgtgc                                                                6

<210> SEQ ID NO 30
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30 tctgta                                                                6

<210> SEQ ID NO 31
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31 atgaca                                                                6

<210> SEQ ID NO 32
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32 cgatgt                                                                6

<210> SEQ ID NO 33
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33 acgcac                                                                6

<210> SEQ ID NO 34
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34 cgatga                                                                6

<210> SEQ ID NO 35
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35 tacact                                                                6

<210> SEQ ID NO 36
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36 cataca                                                                6

```
<210> SEQ ID NO 37
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37 catcgc                                                                     6

<210> SEQ ID NO 38
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38 tcgtga                                                                     6

<210> SEQ ID NO 39
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39 atatct                                                                     6

<210> SEQ ID NO 40
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40 atcgac                                                                     6

<210> SEQ ID NO 41
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41 cgtatc                                                                     6

<210> SEQ ID NO 42
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42 ctctca                                                                     6
```

<210> SEQ ID NO 43
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43 acacgt                                                                    6

<210> SEQ ID NO 44
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44 cagctc                                                                    6

<210> SEQ ID NO 45
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45 tgcgct                                                                    6

<210> SEQ ID NO 46
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46 cgtagc                                                                    6

<210> SEQ ID NO 47
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47 tgtatc                                                                    6

<210> SEQ ID NO 48
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48 acatct                                                                    6

<210> SEQ ID NO 49

```
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49 agatga                                                                   6

<210> SEQ ID NO 50
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50 cacatc                                                                   6

<210> SEQ ID NO 51
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51 cgcgca                                                                   6

<210> SEQ ID NO 52
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52 acagac                                                                   6

<210> SEQ ID NO 53
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53 agtact                                                                   6

<210> SEQ ID NO 54
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54 tagcgc                                                                   6

<210> SEQ ID NO 55
<211> LENGTH: 6
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55 ctatca                                                                    6

<210> SEQ ID NO 56
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56 atagac                                                                    6

<210> SEQ ID NO 57
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57 tatgtc                                                                    6
```

DNA BARCODING OF DESIGNER MONONUCLEOSOME AND CHROMATIN ARRAY LIBRARIES FOR THE PROFILING OF CHROMATIN READERS, WRITERS, ERASERS, AND MODULATORS THEREOF

This application is a National Stage of International Application No. PCT/US2013/044537, filed Jun. 6, 2013, which claims the benefit of the filing date of U.S. Provisional Application 61/656,233, filed Jun. 6, 2012, and of U.S. Provisional Application 61/712,148, filed Oct. 10, 2012, all of which are incorporated by reference in their entireties herein.

This invention was made with government support under Grant No. GM086868 and Grant No. GM107047awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Jun. 5, 2013, is named 32108-348453_SL.txt and is 14,653 bytes in size.

BACKGROUND INFORMATION

In eukaryotic cells, DNA is packaged along with histone proteins in a nucleoprotein complex referred to as chromatin. The minimal repeating units of chromatin are the nucleosomes, which enable the folding of chromatin into fibers and higher order structures. Gene regulation on the chromatin level ('epigenetics') is achieved by nature through dynamic chemical modifications ('marks') of both DNA and histones, mediated by specialized 'chromatin writer' and 'chromatin eraser' enzymes (collectively referred to as 'chromatin modifiers'). 'Histone modifiers' are proteins that attach ('histone writers') or remove ('histone erasers') one or more marks to or from histone proteins, respectively. 'DNA modifiers' are proteins that attach ('DNA writers') or remove ('DNA erasers') one or more marks to or from DNA, respectively. Examples include the pharmacologically relevant histone deacetylases (HDACs) and histone methyltransferases (HMTs). In combination, these modifications form local patterns (within the chromatin fiber, within a single nucleosome, and/or within a single histone), which are thought to serve as recruitment platforms for protein factors with specialized modules that recognize distinct marks ('chromatin readers' or 'chromatin interactors'). 'Histone readers' or 'histone interactors' are proteins that recognize, or bind to, one or more marks on histone proteins, respectively. 'DNA readers' or 'DNA interactors' are proteins that recognize, or bind to, one or more marks on DNA, respectively. DNA and histone marks are important in cellular development and differentiation, and, accordingly, aberrant modifications and impaired combinatorial read-out are implicated in human diseases, especially cancer. As a consequence, chromatin biology and epigenetics have become the focus of many research initiatives in academia and the pharmaceutical industry. And yet, there is a rapidly growing mismatch between the amount of information that is generated by top-down epigenomic and proteomic approaches and the ability to systematically fill in the molecular details of the associated chromatin biochemistry. Despite expanding genomic information and proteomic information about histone sequences, variations, and types and abundance of natural modifications, and some enzymes responsible for modifications, knowledge of highly complex epigenetic mechanisms remains fragmentary, and there is a lack of effective biochemistry tools.

Aberrant posttranslational modification patterns on histone proteins as well as those found on DNA bases are often found in diseases. There is a need for understanding, assaying, and manipulating the underlying mechanisms as a prerequisite for the rational design of next-generation epigenetic drugs.

DESCRIPTION

Figure 1:
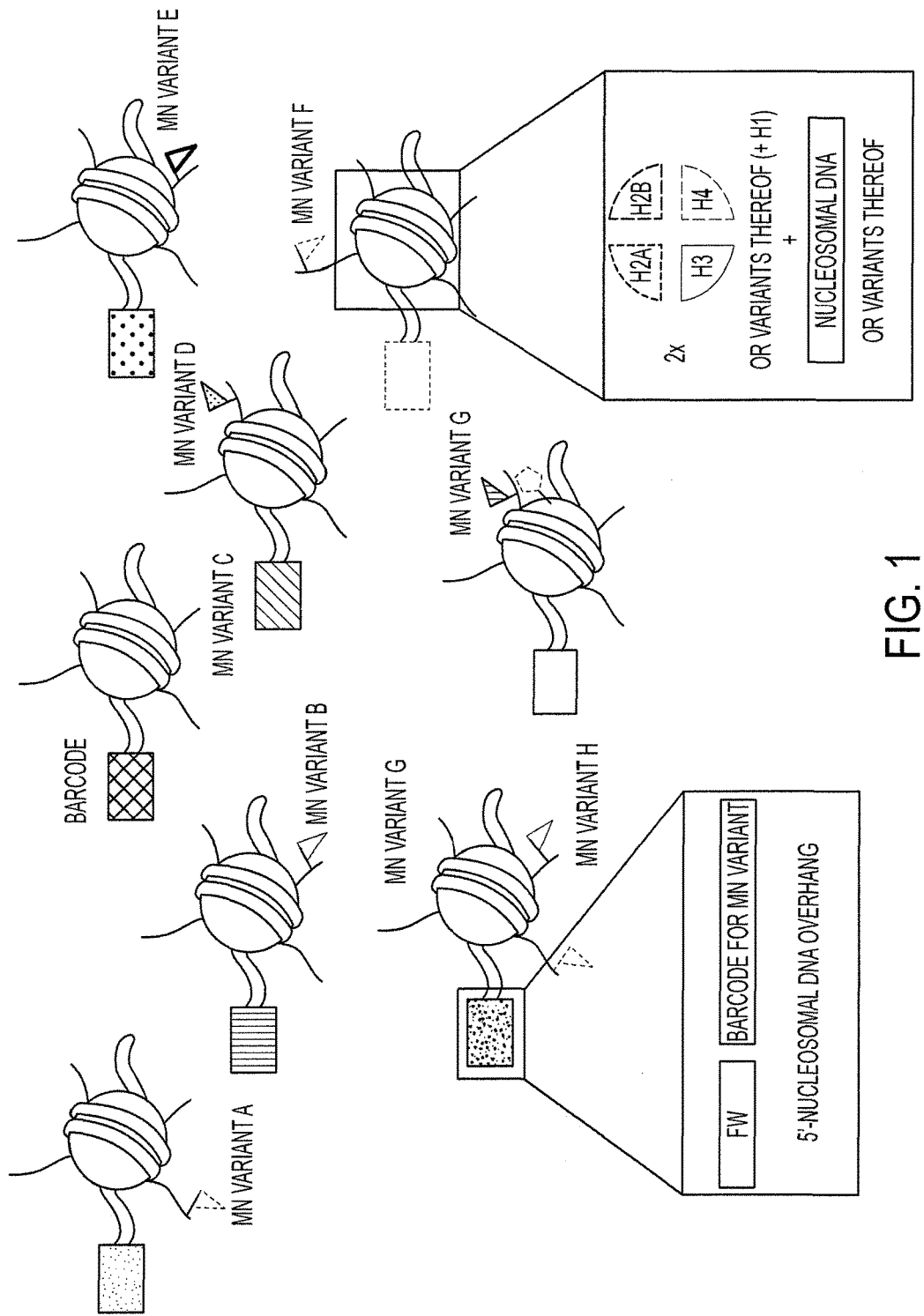
FIG. 1: Exemplary DNA-encoded MN library. In this particular version, each MN library member is barcoded at the 5'-end of the nucleosomal DNA and contains a forward (FW) polymerase chain reaction (PCR) and sequencing priming site for subsequent DNA sequencing readout. The MN barcode encodes the histone variants and/or DNA variant incorporated in the respective MN and/or other histone and non-histone proteins. In general, one or several barcodes can be incorporated anywhere within, at, or near the 5'- or 3'-end of the DNA. White: histone octamer; gray: nucleosomal DNA; black protrusions: N-terminal histone tails. The flags represent different modifications (shown here: modifications on the histones; modifications can also, or instead, be incorporated within the DNA sequence). The different barcodes represent different DNA sequences encoding the respective MN variant. H: histone. MN: mononucleosome. FW: forward sequencing priming site.

This invention relates, e.g., to DNA barcoding of designer mononucleosome and chromatin array libraries for the profiling of chromatin readers, writers, erasers, and modulators thereof. It provides components and methods for massively parallelized quantitative chromatin biochemistry, including a barcoded library of chemically defined nucleosomes, and a barcoded chemically defined polynucleosome library (sometimes referred to herein as a designer chromatin array library, or "CA").

This disclosure meets the need for a robust platform for high-throughput chromatin biochemistry and biophysics. Specifically, we assemble recombinant and synthetic histones (bearing specific post-translational modifications; PTMs) with barcoded DNA sequences (bearing specific epigenetic modifications such as methylation and hydroxymethylation and/or other non-natural modifications) and/or additional linker histone and/or non-histone proteins into designer mononucleosome (MN) and chromatin array (CA) libraries. The histone and/or DNA modifications may be referred to generally as nucleosomal modifications or nucleosome modifications. Sometimes herein, the term chromatin modifications is used. This is an in vitro model that is representative of a chromatin state existing in nature (e.g. in a cell of interest). Using appropriate isolation techniques, such as pull-down experiments, these libraries can be used to profile, among others, (a) mono- or multivalent chromatin readers to investigate their recognition pattern; (b) chromatin writers and erasers to investigate potential histone PTM and DNA modification cross-talks; (c) DNA and histone modifications that modulate the activity of protein factors or enzymes interacting with chromatin; and (d) molecules that modulate the activity of protein factors or enzymes interacting with and/or modifying chromatin. The inventive methods and compositions and devices are amenable to a high degree of parallelization. Additional barcodes, encoding for specific biochemical manipulations of the designer chromatin libraries, may be attached to the DNA molecules. These multiplexed DNA sequences (which code both for (a) specific nucleosome modifications, the nature and type of DNA, and the histone composition of library members as well as (b) the specific experiment) are simultaneously processed by next generation sequencing technologies and other DNA decoding technologies. Analysis of the sequencing data can reveal substrate specificities and potential cross-talks (writers and erasers) and relative binding affinities (readers). Additionally, these experiments enable mechanistic studies and can serve as a diagnostic tool for the activity of large chromatin-associated complexes found in vivo, that often combine chromatin readers, writers, and erasers, such as those derived from nuclear cell extracts of healthy and cancer patients. These methods and compositions provide for the rational design and profiling of next-generation epigenetic drugs.

One aspect of the invention is a library of synthetic (isolated, synthetically produced, free from components that are naturally found associated with mononucleosomes in a cell, purified before being put into the library) mononucleosomes, wherein the library comprises two or more (e.g., at least 10, 50, 100, 200, 500, 1000, 2000, 3000, 4000, 5000 up to about 10,000 or more) types of mononucleosomes (members of a set of mononucleosomes). The lowest number of library members is 2. The upper limit of the library size is defined by the combinatorics of histone variants (hundreds to thousands), DNA variants (hundreds to thousands), and non-histone chromatin-associated proteins (hundreds to thousands). One example is a library that contains one of each of the following modifications: histone posttranslational modifications (approximately 100 s) (ENCODE Project Consortium et al., 2012), histone isoforms (approximately 100 s), DNA modifications (approximately 100 s), and chromatin-associated proteins (approximately 100 s), resulting in a library of hundreds to thousands of nucleosomes. In another example, a library contains all biologically relevant chromatin states (a chromatin state is a chromatin molecule with a defined, naturally occurring combination of histone posttranslational modifications, histone isoforms, DNA modifications, and chromatin-associated proteins), resulting in a library of hundreds, potentially thousands of nucleosomes. In another example, a library can be geared toward a specific experiment. For example, the role of trimethyllysines in nucleosome binding/recognition can be addressed using only a fraction of naturally occurring nucleosome variants, namely the subset containing all known trimethyllysine-containing histone variants, resulting in a library of tens to hundreds of nucleosomes. Another example comprises library members from all three library types described above.

Each mononucleosome comprises a complex of:
(a) a protein octamer, containing 2 copies each of histones H2A, H2B, H3, and H4, and optionally, linker histone H1, wherein at least one of the histones is unmodified and/or wherein at least one of the histones is modified, to form a pattern of histone modifications, (Histone modifications can be histone isoforms, PTMs, and/or unnatural amino acids) and
(b) a nucleosomal DNA molecule (a DNA molecule that is part of a mononucleosome, e.g., is wound around the octamer of histone proteins. A nucleosomal DNA present in a mononucleosome is sometimes referred to herein as a "mononucleosomal or mononucleosome DNA." A nucleosomal DNA is associated with a nucleosome). The nucleosomal DNA comprises a (as used herein, the terms "a" and "the" refer to one or more than one, unless the context clearly dictates otherwise):
(i) a strong nucleosome positioning sequence (NPS) (e.g., which can bind tightly enough to prevent scrambling of the synthetic mononucleosomes, e.g. which bind to histone octamers approximately 50 times, 70 times, 80 times, 90 times, 100 times, 125 times, 150 times, 200 times, 250 times, or more, more tightly than bulk DNA), (ii) one or more DNA barcode(s) located at defined position(s) in the nucleosomal DNA (e.g. located within, or at or near one end of the nucleosomal DNA, such as at a specific distance from the NPS or other fixed point in the DNA), and, optionally, (iii) DNA extensions, including DNA linkers, on the 5'- and/or 3'-end of the NPS and/or within the NPS. These include covalently attached DNA sequences and artificial non-DNA molecules.

The nucleosomal DNA molecule may be unmodified and/or at least one of the nucleotides in the DNA may be modified, to form a unique pattern of DNA modifications.

Optionally, the mononucleosome may comprise (c) one or more non-histone chromatin-associated proteins.

In a synthetic mononucleosome library of the invention, each mononucleosome of the library may have a unique pattern of histone modifications and/or a unique pattern of DNA modifications, thereby forming a unique pattern of nucleosome modifications. The DNA molecule may comprise one or several unique barcode(s) whose sequence and position in the nucleosomal DNA is indicative of (correlated with, associated with, in a predetermined relationship with) the unique pattern of nucleosome modifications.

Another aspect of the invention is a synthetic polynucleosome (sometimes referred to herein as synthetic chromatin, or a synthetic chromatin array (CA)), which comprises two or more synthetic mononucleosomes (e.g., at least 3, 5, 7, 9, 12, 15, or 20) bonded together (linked together) by a defined DNA molecule (e.g. each of which defined DNA molecules can have the same or a different sequence), the mononucleosomes having a defined connectivity (spatial orientation with regard to one another).

Each of these mononucleosomes comprises a complex of (a) a protein octamer, containing 2 copies each of histones H2A, H2B, H3, and H4, and optionally, linker histone H1, wherein at least one of the histones is unmodified, and/or at least one of the histones is modified to form a pattern of mononucleosomal histone modifications; and (b) a nucleosomal DNA molecule; and optionally (c) one or more non-histone chromatin-associated proteins.

In a synthetic polynucleosome of the invention, the pattern of mononucleosomal nucleosome modifications of the mononucleosomes in the polynucleosome may be uniform or may be different (unique), resulting in a unique pattern of polynucleosomal nucleosome modifications. The polynucleosome may comprise a (one or more) barcode(s) located at a defined position in the polynucleosomal DNA (e.g. located internally within the polynucleosomal DNA, or at or near the 5' or 3 end of the polynucleosomal DNA). A nucleosomal DNA present in a polynucleosome is sometimes referred to herein as a "polynucleosomal DNA." The defined position of the barcode may be, e.g., at a specific distance from a nucleosome positioning sequence (NPS) or other fixed point in the polynucleosomal DNA. The combination of the sequence of the barcode and position in the polynucleosomal DNA is indicative of the unique pattern of polynucleosomal nucleosome modifications.

Another aspect of the invention is a library of synthetic polynucleosomes (sometimes referred to herein as synthetic chromatin, or a synthetic chromatin array (CA)), which comprises two or more synthetic polynucleosomes as described above. Each member of such a library has one or more unique barcodes, whose sequence and location in the polynucleosomal DNA is indicative of a unique pattern of polynucleosomal modifications.

In a library of the invention (a mononucleosome library or a polynucleosome library), the histones may be modified in any of a variety of ways. These modifications may comprise, e.g., histone isoforms, PTMs, and/or unnatural amino acids.

Histone isoforms or variants may be naturally occurring or artificial. They are characterized by amino acid substitutions (for example the most common histone H3 variants are H3.1, H3.2, H3.3) or amino acid insertions within the protein sequences or extensions at the end of the protein sequences (e.g. macro-H2A). A partial list of histone isoforms in humans includes:

(a) Histone H2A:
H2AF, H2AFB1, H2AFB2, H2AFB3, H2AFJ, H2AFV, H2AFX, H2AFY, H2AFY2, H2AFZ, H2A1, HIST1H2AA, HIST1H2AB, HIST1H2AC, HIST1H2AD, macro-H2A, HIST1H2AE, HIST1H2AG, HIST1H2AI, HIST1H2AJ, HIST1H2AK, HIST1H2AL, HIST1H2AM, H2A2 HIST2H2AA3, HIST2H2AC (b) Histone H2B:
H2BF, H2BFM, H2BFS, H2BFWT, H2B1, HIST1H2BA, HIST1H2BB, HIST1H2BC, HIST1H2BD, HIST1H2BE, HIST1H2BF, HIST1H2BG, HIST1H2BH, HIST1H2BI, HIST1H2BJ, HIST1H2BK, HIST1H2BL, HIST1H2BM, HIST1H2BN, HIST1H2BO, H2B2, HIST2H2BE (c) Histone H3:
H3A1, HIST1H3A, HIST1H3B, HIST1H3C, HIST1H3D, HIST1H3E, HIST1H3F, HIST1H3G, HIST1H3H, HIST1H3I, HIST1H3J, H3A2, HIST2H3C, H3A, HIST3H3, CENP-A (d) Histone H4:
H41, HIST1H4A, HIST1H4B, HIST1H4C, HIST1H4D, HIST1H4E, HIST1H4F, HIST1H4G, HIST1H4H, HIST1H4I, HIST1H4J, HIST1H4K, HIST1H4L, H44, HIST4H4

(e) Linker histone H1:
H1F, H1F0, H1FNT, H1FOO, H1FX, H1H1, HIST1H1A, HIST1H1B, HIST1H1C, HIST1H1D, HIST1H1E, HIST1H1T Other histone isoforms will be evident to skilled workers.

Additionally, mutations in histones have been observed in cancers (e.g. Lys27Met in the tail of H3.3 occurs frequently in pediatric brain stem tumors); and such mutants can be included in libraries of the invention as well.

A variety of PTMs of histones will be evident to a skilled worker. These include any naturally occurring histone modification, e.g., methylation, acetylation, phosphorylation, ubiquitination, ADP-ribosylation, SUMOylation, glycosylation, alkylation, acylation, prolyl cis/trans isomerization, nitrosylation and oxidation. PTMs that have not yet been discovered or characterized are included in the invention.

Unnatural aminoacids include synthetic analogs of PTMs, which can be chemically and/or biochemically inert, photo-crosslinkers, fluorescent labels, isotope labels or others that will be evident to a skilled worker.

The modifications can occur at one site, or at more than one site, in a nucleosome.

A "barcode" as used herein is a nucleic acid sequence that, in conjunction with its location in a DNA molecule, can be used to unambiguously identify that DNA molecule, e.g. in the context of a library of nucleosomes. The number of barcodes is dictated by the complexity of the library to be used, which in turn is dependent on the number and combinations of histone variants (in the examples shown herein, these histones differ in their histone PTM status), DNA sequences, additional chromatin-associated proteins used to form a unique nucleosome or chromatin array variant. For example, a 1 nucleotide (nt) barcode can code for 4 library members, a 2 nt barcode 16 variants, 3 nt barcode 64 variants, 4 nt 256 variants, 5 nt 1,024 variants and so on. The length of the DNA barcode(s) is determined by the size of the library. Depending on the library size, the DNA barcode has a number of bases sufficient to provide a sufficient number of variations to uniquely code each member of the library. The barcode(s) can be single-stranded (ss) DNA or double-stranded (ds) DNA (as shown in the Examples herein) or a combination thereof.

In the examples described herein, a 6 nucleotide barcode is used, which in principle encodes 4,096 different nucleosome or chromatin array variants. In general, barcodes of 4-12 nucleotide lengths cover most applications with library sizes that are realistic, but the barcode can be longer, if a higher combinatorial power is needed.

A "nucleosome positioning sequence (NPS)" is a natural or synthetic double-stranded DNA sequence of at least 146 base pairs which interacts strongly with histones and histone complexes, in particular histone octamers (which consist of 2 copies of the histones H2A, H2B, H3, and H4). An NPS forms the nucleosome with a specific position and orientation of the histone octamer with respect to the DNA. The histone-DNA complex must be stable for an extended period of time for storage (months at 4° C.), and during standard biochemical manipulations (at concentrations of low tens of nanomolar (nM) in common buffers and hours at 30° C.). The NPS used in the Examples herein is an artificial sequence referred to as 601, which binds to histone octamers approximately 100 times more tightly than bulk DNA (Lowary & Widom, 1998). Any alternative artificial or natural DNA sequence that meets the criteria described above, many of which will be evident to a skilled worker, can be used. For example, an NPS can bind to histone octamers approximately 10 times, 20 times, 30 times, 40 times, 50 times, 60 times, 70 times, 80 times, 90 times, 100 times, 125 times, 150 times, 200 times, 250 times, or more, more tightly than bulk DNA.

DNA extensions of the mononucleosome or polynucleosome DNAs of the invention can take any of a variety of forms. For example, they can be DNA barcodes, DNA priming sites (e.g. for the downstream sequencing readout or for PCR amplifications), DNA linkers (as outlined in the next paragraph), alternative positioning sequences, protein binding sites (for additional histone or non-histone proteins), enzyme DNA substrates, base-modified DNA, or any other artificial non-DNA molecules, such as affinity handles (e.g. biotin) or fluorescent probes.

DNA linkers in mononucleosome or polynucleosome DNAs of the invention can be of a variety of lengths and compositions. In nature, nucleosomes are usually separated by ~10-90 bp of linker DNA. These linkers vary among different tissues, species or even within a single cellular genome, and in base composition. Artificial linkers are characterized by their reluctance to be wrapped around histone octamers. Practically, an upper limit for DNA appendages is in the range of 100-1000 bp as longer sequences might perturb the positioning of the histones on the DNA strand.

The mononucleosome or polynucleosome DNAs of the invention can comprise one or more unmodified DNA bases, bases with naturally occurring modifications, such as methylation, alkylation or oxidation, or bases with artificial modifications. A variety of suitable modifications will be evident to the skilled worker.

A variety of non-histone chromatin-associated protein will be evident to the skilled worker and include transcription factors, histone interactors and modifiers, and chromatin remodeling proteins.

Figure 12A:
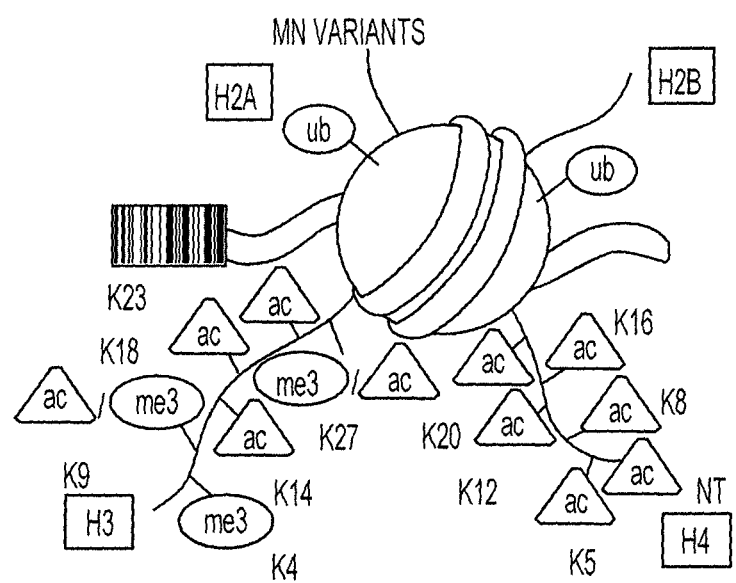
FIG. 12: (A) Diagrammatic representation of MN variants 1-39. (B) List of the histone composition of MN variants 1-39 and their corresponding nucleosomal DNA barcode. All wt histones were prepared recombinantly in *E. coli*. Semi-synthetic histone proteins were prepared by NCL (FIG. 9a). Semi-synthetic H4 proteins contained an additional N-terminal acetyl group (not indicated in the table). (C) Assessment of DNA ligation products by ethidium bromide-stained native polyacrylamide gels. ub: ubiquitin; ac: acetyl; me: methyl; wt: wild-type; MN: mononucleosome; ID: identification; H3 Kac$_5$: K9/14/18/23/27ac; H4Kac$_5$: K5/8/12/16/20ac. The sequences in FIG. 12B, reading from top to bottom, are SEQ ID NO's: 19-57, respectively.

Another aspect of the invention is a kit, e.g. for carrying out one of the methods described herein. The kit may comprise nucleosomes (mononucleosomes or polynucleosomes) or a mononucleosome or polynucleosome library of the invention. The kit may comprise a list (compendium, algorithm, summary, computer readable medium, or the like) indicating the correlation (relationship, association, predetermined relationship) between each unique barcode(s) and unique pattern of nucleosome modifications. An exemplary list of this type is shown in FIG. 12B. In embodiments of the invention, the nucleosomes or libraries are in test tubes, the wells of a multiwell plate, or in a reaction chamber of a microfluidic device. Other optional elements of a kit of the invention include suitable buffers, media components, substrates, cofactors, inhibitors, and the like; a computer or computer-readable medium for storing and/or evaluating the assay results; or packaging materials.

Another aspect of the invention is a method for determining the specificity of chromatin reader recognition patterns and affinities, specificities and cross-talks of chromatin writers and erasers, comprising incubating (contacting) a library of the invention with one or several chromatin interactors and/or modifiers of recombinant origin, or incubating a library of the invention with chromatin interactors and/or modifiers derived from a nuclear cell extract of a cell line to be investigated (e.g., including cells derived from human cancer patients), isolating bound and/or modified library members, and identifying and/or quantitating the bound or modified library members and any added marks or removed marks. The method may comprise analyzing large chromatin remodeling complexes. The method may comprise analyzing a cell line, including cells derived from human cancer patients.

Another aspect of the invention is a method for identifying the modifications associated with an interactor or modifier, comprising multiplexing a number greater than one of chromatin interactors and/or modifiers with a library of the invention, and dividing the library into the same number of sublibraries according to the modifications, and identifying the modifications associated with each interactor or modifier.

Another aspect of the invention is a method for identifying and profiling the specificity of epigenetic drugs, comprising combining a candidate molecule with a library of the invention, and detecting modulation of a nucleosome modification (e.g. inhibiting or agonizing protein factors or enzymes interacting with chromatin), thereby identifying candidate epigenetic drugs which modulate nucleosome modifications.

Another aspect of the invention is a library of nucleosomes in combination with a list of DNA barcodes and the associated nucleosome modifications and composition of each barcoded nucleosome.

Another aspect of the invention is a synthetic mononucleosome or polynucleosome comprising a DNA barcode at the 5'- and/or 3'-end of or anywhere within the DNA molecule.

Another aspect of the invention is a synthetic mononucleosome, comprising a complex of (a) a protein octamer, containing 2 copies each of histones H2A, H2B, H3, and H4, and optionally, linker histone H1, wherein at least one of the histones is unmodified and/or wherein at least one of the histones is modified, to form a pattern of histone modifications (e.g., histone isoforms, PTMs, and/or unnatural amino acids), and
   (b) a nucleosomal DNA molecule comprising
     (i) strong nucleosome positioning sequence (NPS),
     (ii) one or more DNA barcode(s) located at defined position(s) in the nucleosomal DNA (e.g. located within, at, or near one end of the nucleosomal DNA, such as at a specific distance from the NPS or other fixed point in the DNA),
     (iii) DNA extensions, including DNA linkers, on the 5'- and/or 3'-end of the NPS and/or within the NPS (e.g., covalently attached DNA sequences and artificial non-DNA molecules), and optionally
   (c) one or more non-histone chromatin-associated proteins,
wherein the sequence and position of the barcode(s) in the nucleosomal DNA is indicative of the pattern of nucleosome modifications in the mononucleosome. Another aspect of the invention is a method for assembling a mononucleosome of the invention, comprising combining histone proteins and barcoded nucleosome DNA. The method may comprise, e.g., combining histone proteins and barcoded nucleosomal DNA with a biotin-tagged MMTV buffer DNA, in a predetermined ratio. Any of a variety of sequences other than MMTV and affinity tags other than biotin can also be used. Suitable sequences and affinity tags will be evident to those of skill in the art.

In a library of the invention, the NPS in the mononucleosomes or polynucleosomes are generally sufficiently strong so that the library is stable, and no significant DNA scrambling occurs between mono- and polynucleosome library members after extended storage, e.g. for at least a month at 4° C. In aspects of the invention, the histone and/or DNA modifications comprise a representative set of biologically relevant chromatin states. In aspects of the invention, the ratio of the mono- and polynucleosome library members is equimolar (1:1 for each library member) or non-equimolar, ranging from 1 to 1000 (e.g., 1:10, 1:50, 1:100, 1:150, 1:200, 1:300, 1:400, 1:500, 1:600, 1:700, 1:800, 1:900) for one or for a subset of the library members (e.g., ranging from 1 to 1000, such as 1, 10, 50, 100, 150, 200, 300, 400, 500, 600, 700, 800, 900 or 1000) in a fixed, predetermined ratio.

Embodiments of the invention include the following.

(A) DNA Barcoding of the Synthetic History of Each MN or CA Library Member

This embodiment relates to the fabrication of designer mononucleosome (MN) and designer chromatin array (CA) libraries, where each library member carries (a) DNA barcode(s) that encode(s) the specific synthetic history of each MN or CA variant.

A MN is a complex consisting of
(1) a protein octamer, containing 2 copies of the canonical histones H2A, H2B, H3, and H4 (or modified versions thereof), and in some cases, linker histone H1,
(2) a nucleosomal DNA molecule comprising
   (i) strong nucleosome positioning sequence (NPS),
   (ii) one or more DNA barcode(s) located at defined position(s) in the nucleosomal DNA (e.g. located within, at, or near one end of the nucleosomal DNA, such as at a specific distance from the NPS or other fixed point in the DNA),
   (iii) DNA extensions, including DNA linkers, on the 5'- and/or 3'-end of the NPS and/or within the NPS (e.g., covalently attached DNA sequences and artificial non-DNA molecules), and optionally
   (c) one or more non-histone chromatin-associated proteins.

Specifically, each member of the MN library carries
   (a) a unique combination of histone variants, including histone isoforms, histone PTM patterns, histones with unnatural amino acids.
   and
   (b) a unique nucleosomal DNA variant, containing a NPS, DNA barcode(s), and/or DNA extensions. The DNA can either contain the canonical DNA bases, bases with naturally occurring modifications (such as methylation or oxidation), or bases with artificial modifications, and optionally,
   (c) one or more non-histone chromatin-associated proteins.

The composition of each unique MN, with different histone PTM and/or DNA modification patterns and/or other histone and non-histone proteins, is encoded in (a) DNA sequence(s) (herein referred to as MN barcode) anywhere within, at, or near the end of the nucleosomal DNA, such as the 5'-end (FIG. 1). The upper limit of the library size is defined by the combinatorics of histone and DNA variants. For practical reasons, the size of the library is defined by the downstream experiment and typically ranges from tens to hundreds to thousands of library members. For example, the size may be, or may be less than about, or greater than about 10, 20, 30, 50, 75, 100, 150, 200, 250, 300, 400, 500, 600, 700, 800, 900, 1000, 1250, 1500, 2000, 2500, 3000, 3500, 4000, or more library members.

A CA is a complex consisting of MN units (see MN definition above), which can be (a) uniformly modified, or (b) uniquely modified. The length of the array is variable and typically ranges from 2-12 MNs, such as a dimer, trimer, pentamer, and so on. The MNs are connected to one another in a defined sequence. A synthetic chromatin array may also be referred to here as a polynucleosome, in contrast to a synthetic mononucleosome.

The number may be any number up to 8, 10, 12, 14, 15, 16, 18, or 20.

Each member of the CA library is composed of individually modified MNs with a defined connectivity and carries:
   (a) MNs, with
     (i) a unique combination of histone variants, including histone isoforms, histone PTM patterns, histones with unnatural amino acids,
     (ii) a unique nucleosomal DNA variant, containing one or several different NPSs, DNA barcode(s), and/or DNA linkers. The DNA can either contain the canonical DNA bases, bases with naturally occurring modifications (such as methylation or oxidation), or bases with artificial modifications, and/or
   (c) linker histones, and/or other non-histone proteins.

Figure 2:
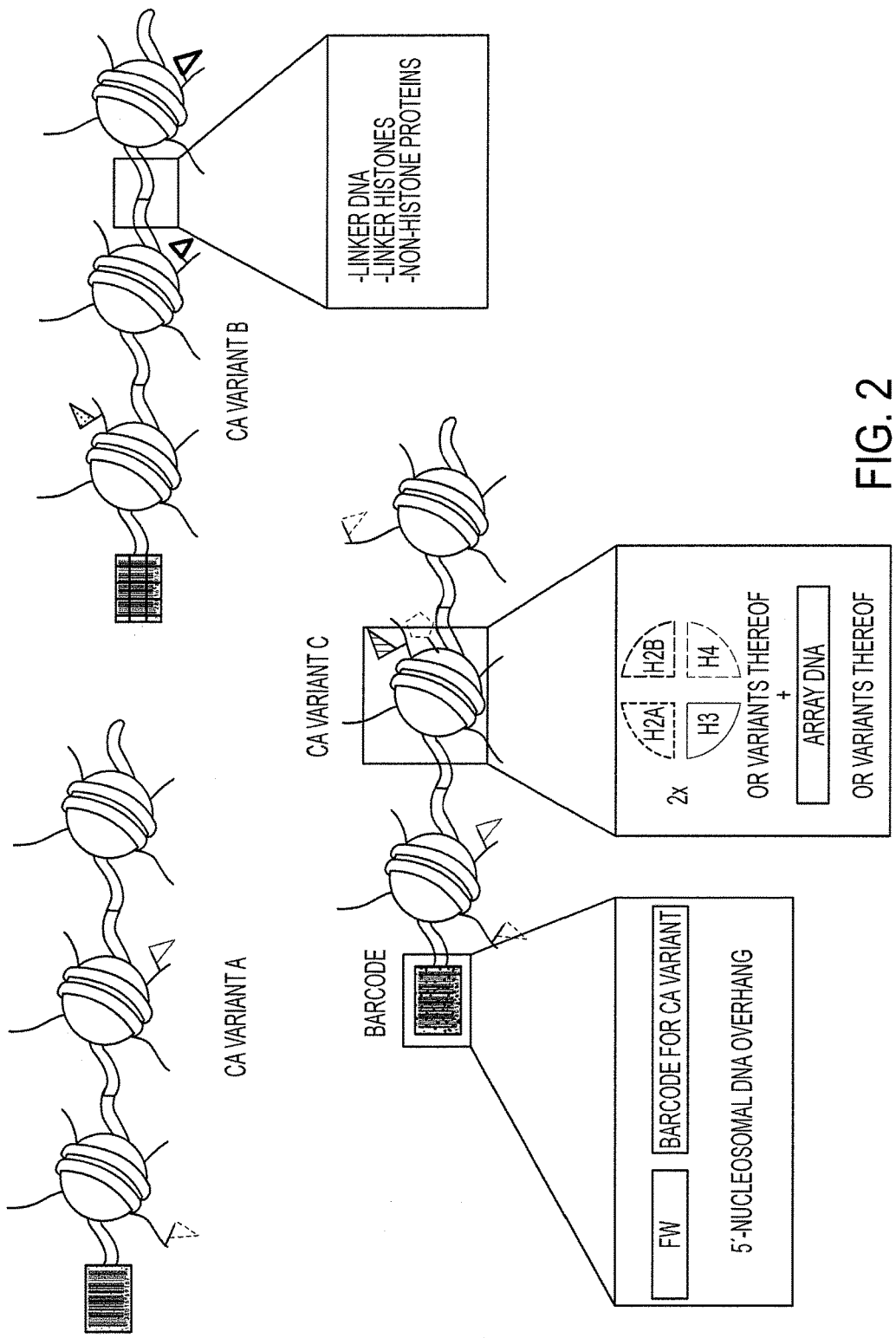
FIG. 2: Exemplary DNA-encoded CA library consisting of tri-MNs. In this particular version, each MN library member is barcoded at the 5'-end of the array DNA and contains a PCR and sequencing priming site for subsequent DNA sequencing readout. The CA barcode encodes the histone variants and/or DNA variants, DNA extensions, linker histones, and/or other non-histone proteins, incorporated in the respective CA. In general, one or several barcodes can be incorporated anywhere within, at, or near the 5'- or 3'-end of the DNA. White: histone octamer; gray: array DNA; black protrusions: N-terminal histone tails. The flags represent different modifications (histone or DNA) modifications as in FIG. 1. The different barcodes represent different DNA sequences encoding the respective CA variant. H: histone. MN: mononucleosome. CA: chromatin array. FW: forward sequencing priming site.

The protein PTM and/or DNA modification pattern, MN connectivity, length and identity of the DNA, presence and modification pattern of linker histones, and/or non-histone proteins are encoded in (a) DNA sequence(s) (herein referred to as CA barcode) anywhere within, at, or near the end of the array DNA, such as the 5'-end (FIG. 2). The upper limit of the library size is defined by the combinatorics of the individual PTM and/or DNA modifications, MN connectivity, DNA variant, linker histones, and/or non-histone proteins. For practical reasons, the size of the library is defined by the downstream experiment and typically ranges from hundreds to thousands of library members.

The MN or CA barcodes uniquely and unambiguously tag the chemical composition of the MN or CA within the library. These barcoded libraries can be used both for testing and generating various biochemical and biophysical hypotheses, such as profiling substrate specificities of chromatin interactors or modifiers (FIG. 3) through the process of barcode decoding (in analogy to existing procedures based on DNA-encoded chemical libraries (Buller, Mannocci, & Scheuermann, 2010; Clark, 2010)). Suitable methods include
(1) restriction-digestion
(2) Polymerase Chain Reaction (PCR)
(3) DNA microarray hybridization
(4) DNA sequencing, such as the next generation sequencing (Mardis, 2008) technologies
Ion Torrent (Rothberg et al., 2011) or Illumina.

In the case of DNA sequencing, the required forward (FW) and reverse (RV) sequencing priming sites can be added to the nucleosomal or array DNA at any stage of the process, such as by molecular cloning, PCR, or DNA ligation.

In addition to the identification of the MNs or CAs with the desired biochemical or biophysical properties, quantification of the isolated library members is feasible, in particular when using next generation sequencing technologies (Mardis, 2008) as a read-out. In combination with an absolute DNA quantification step prior to sequencing, e.g. by quantitative PCR (qPCR), relative binding affinities of MN or CA substrates can be obtained in a single multiplexed experiment, as outlined below.

Figure 3:
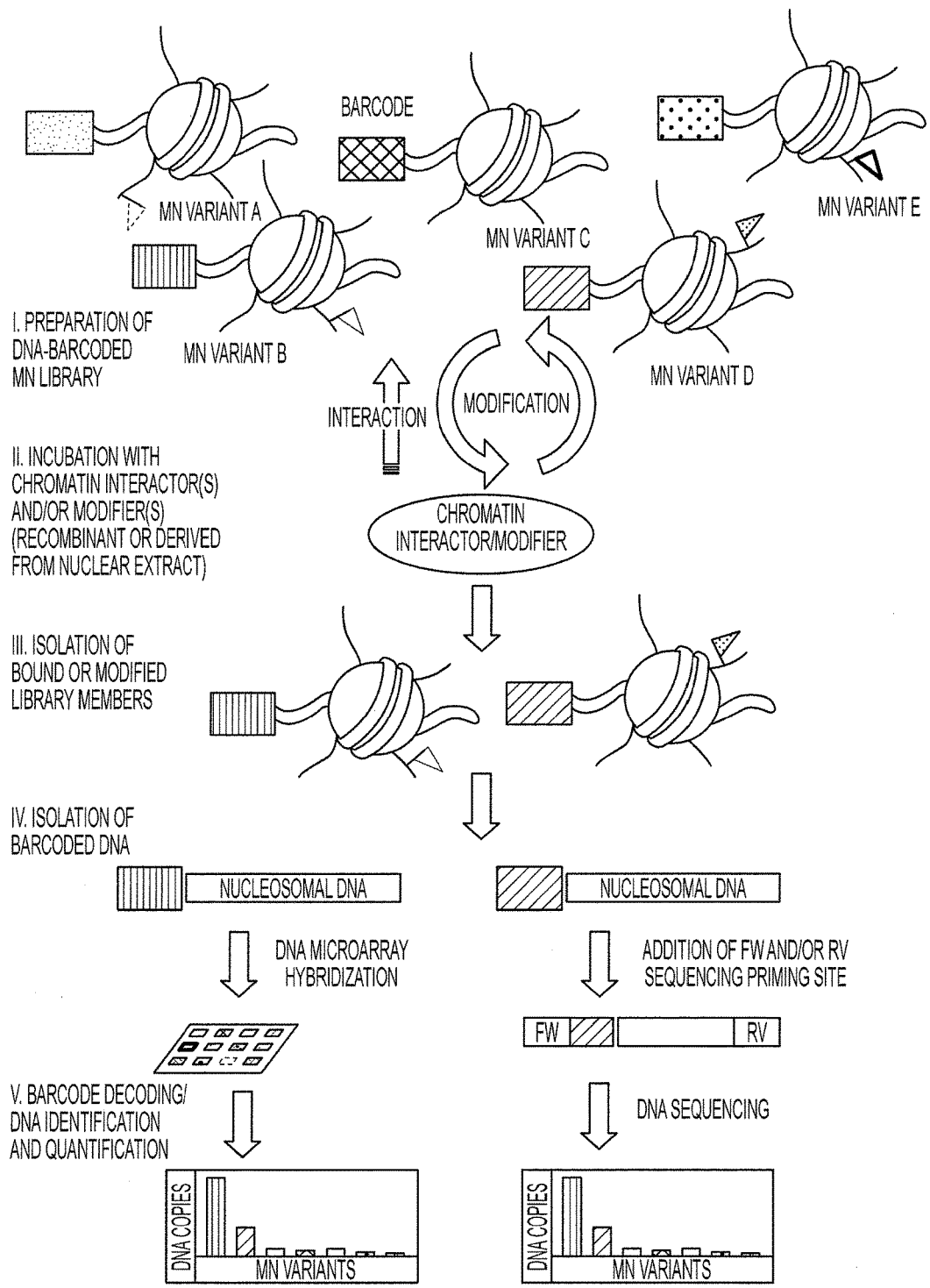
FIG. 3: Example for the use of a DNA-barcoded MN library for the profiling of chromatin interactors/modifiers. I. In this particular version, each MN library member is barcoded at the 5'-end of the nucleosomal DNA. The MN barcode encodes the histone variants and/or DNA variants. II. Incubation of the chromatin interactor(s) or modifier(s) with the library (recombinant or derived from nuclear cell extracts). III. Isolation of the bound or modified MN substrates, such as by antibody pull-down. IV. Isolation of barcoded DNA sequences using protein digestion and DNA purification. V. Data analysis: DNA identification and quantification after input normalization. Barcode decoding can be achieved either by DNA microarray hybridization or DNA sequencing after addition of FW and RV sequencing priming sites, such as by PCR or T4 DNA ligation (Note: optionally, the FW and/or RV priming site can also be included in the nucleosomal DNA prior to MN formation). White: histone octamer; gray: nucleosomal DNA; black protrusions: N-terminal histone tails. The flags represent different modifications shown on histones but potentially also on DNA. The different barcodes represent different DNA sequences encoding the respective MN variant. MN: mononucleosomes. FW: forward sequencing priming site. RV: reverse sequencing priming site.

For example, a protein interacting with chromatin (such as a chromatin reader) or modifying chromatin (such as a chromatin writer or eraser) of recombinant origin or derived from nuclear cell extracts is incubated with the barcoded MN or CA library (FIG. 3). In the particular case described in this example, it is a MN library with a ds barcode attached prior to MN formation at the 5'-end of the nucleosomal Widom 601 DNA, an artificial stretch of 147 bp of double-stranded (ds) DNA to which histone octamers bind with high affinity (Lowary & Widom, 1998). The size and composition of the libraries can be adapted to the downstream experiment in a modular fashion. In the following step, the MN or CA substrates with the desired biochemical or biophysical properties are isolated by appropriate methods, including:
(1) Pull-down (affinity- or immunoprecipitation) experiments
(2) Separation by differential physical or chemical properties upon MN or CA binding or modification, such as electrophoretic mobility (electrophoretic mobility shift assays), hydrophobicity, charge (ion exchange chromatography), or size (size exclusion chromatography, SEC)
(3) Fluorescence activated molecule cell sorting (FAMS) using
(1) Tagging of interactor (chromatin reader)
(2) Labels (affinity, chemical handle, fluorescence probe) on the interactor for direct isolation (e.g. using fluorescence-based molecule sorting) or further biochemical or chemical functionalization (chromatin reader)
(3) Secondary protein that recognizes interactor (chromatin reader)
(4) Antibodies against attached or removed mark (chromatin modifier)
(5) Secondary protein (reader) that recognizes attached or removed mark (chromatin modifier)
(6) Modified enzyme substrates with artificial labels (affinity, chemical handle, fluorescence probe) for direct isolation (e.g. using fluorescence-based molecule sorting techniques) or further biochemical or chemical functionalization (chromatin modifier)

For example, an antibody against the protein or the attached or removed modification is used to (a) pull down the chromatin interactor, such as a reader, in complex with its tightest MN or CA binders, or (b) to isolate the preferred MN or CA substrates of the chromatin modifier, such as a writer or eraser. After DNA isolation, the chromatin interactors or substrates are identified and quantified through decoding of the MN or CA barcode using methodologies such as DNA microarray hybridization or DNA sequencing (Mardis, 2008), e.g. Ion Torrent (Rothberg et al., 2011) or Illumina.

(B) DNA Barcoding of the Experimental History of Each MN or CA Library Member.

This embodiment involves manipulations by a biochemical or biophysical process, such as biochemical or biophysical manipulations in the presence of additional molecules that modulate the process, including inhibitors and/or activators of chromatin-interacting proteins and chromatin-modifying enzymes. DNA barcoding is known in the different context of labeling small molecule libraries (Buller et al., 2010; Clark, 2010; Kleiner, Dumelin, & Liu, 2011) and antibodies (Agasti, Liong, Peterson, Lee, & Weissleder, 2012; Krutzik & Nolan, 2006).

Figure 4:
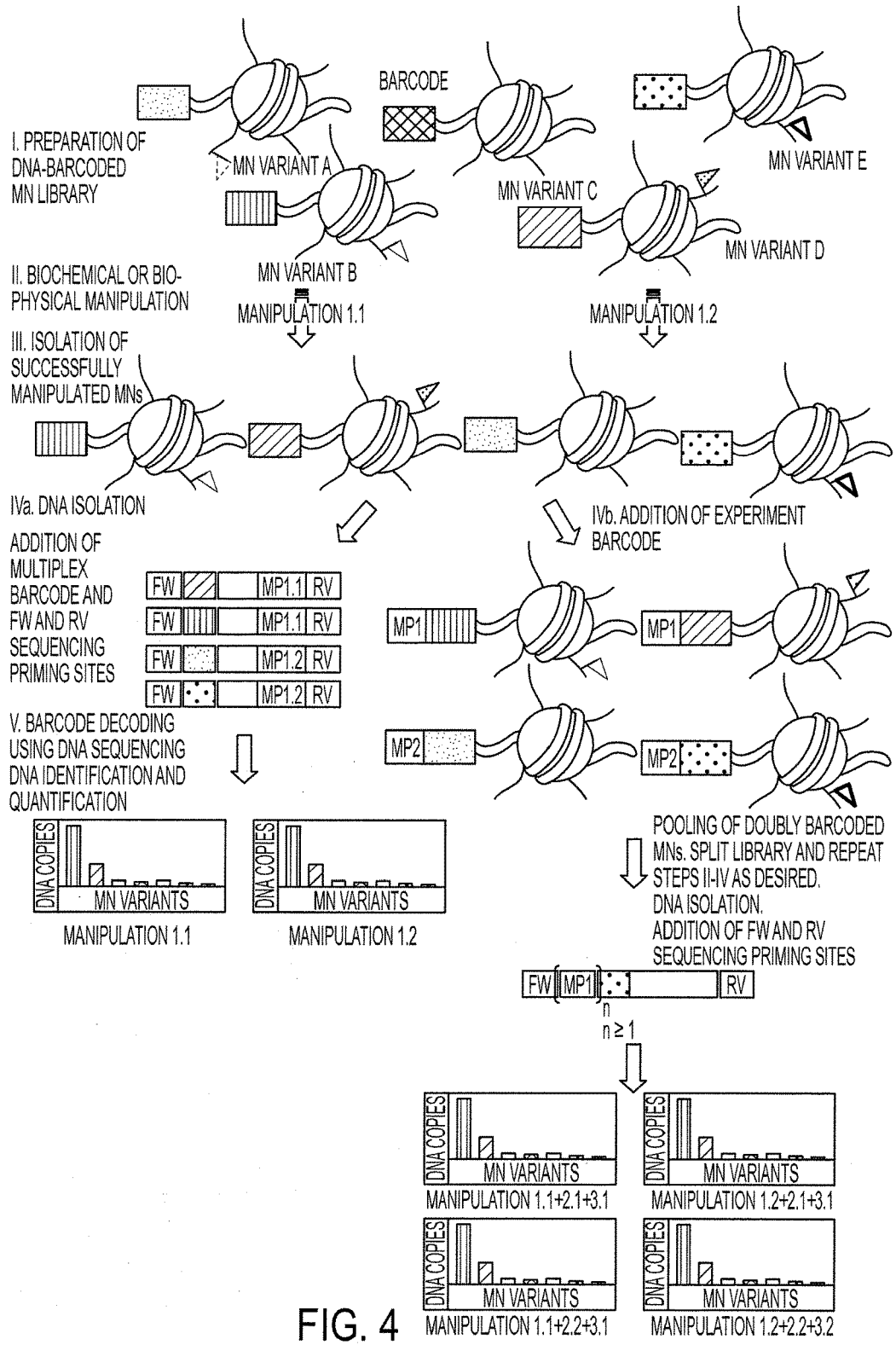
FIG. 4: Examples for barcoding the manipulation steps performed on a MN library. I. In this particular version, each MN library member is barcoded at the 5'-end of the nucleosomal DNA. The MN barcode encodes the histone variants and/or DNA variants. II. The library is split and subjected to various biochemical or biophysical manipulations, here to exemplary manipulations 1.1 and 1.2. III. Isolation of successfully manipulated MNs, such as by antibody pull-down. IVa. Preparation of DNA library for DNA sequencing: Isolation of barcoded DNA using protein digestion and DNA purification, followed by addition of experiment (multiplex) barcode (here: MP1.1 and MP1.2) as well as FW and RV sequencing priming sites by PCR (Optionally, the FW and/or RV priming site can also be included in the nucleosomal DNA prior to MN formation). IVb. Addition of experiment barcodes (here: MP1 and MP2), e.g. to the 5'-nucleosomal end of the DNA. Pooling of doubly barcoded MN. Split library and repetition of steps II-IVb as desired (shown here: 3 manipulation rounds with 2 different manipulations each). DNA isolation. Addition of FW and RV sequencing priming sites (Note: the FW and/or RV priming site can also be included in the nucleosomal DNA prior to MN formation). V. Data analysis: DNA identification and quantification. White: histone octamer; gray: nucleosomal DNA; black protrusions: N-terminal histone tails. The flags represent different modifications as in prior Figures. The different barcodes represent different DNA sequences encoding the respective MN variant. MN: mononucleosomes. MP: Multiplex (experiment) barcode. FW: forward sequencing priming site. RV: reverse sequencing priming site.

For example, a barcoded MN or CA library is manipulated by various biochemical or biophysical processes (FIG. 4). In the particular case described in this example, it is a MN library with a barcode attached prior to MN formation at the 5'-end of the nucleosomal 601 DNA. The manipulation steps are subsequently encoded in separate barcodes (herein referred to as experiment barcode).

Variant A: If the experiment is subjected to one experimental manipulation step only, the experiment (multiplex) barcode can be attached after substrate and DNA isolation by PCR. In this PCR step, the identity of the MN or CA variant is coupled to the specific experiment through the generation of a DNA sequence that contains both the MN or CA barcodes as well as the experiment (multiplex) barcode. The length of the doubly barcoded DNA sequence, which also comprises the FW and RV priming sites for subsequent sequencing, is limited by the length of reliable readout by the chosen DNA sequencing method.

Variant B: If multiple experimental manipulations are performed, the experiments barcodes can be attached to the 5'- or 3'-end of the nucleosomal or array DNA of each library member.

The sub-libraries that were subject to manipulation by the specific biochemical or biophysical process are isolated by suitable methods as outlined above, and a barcode encoding the specific manipulation performed is ligated to all sub-library members. The differentially barcoded libraries are pooled and split again for subsequent manipulation by a second biochemical or biophysical process and handled as described for the first step by attaching a second experiment barcode to the 5'- or 3'-end of the DNA. This can be repeated as desired. In the last barcoding step, the FW sequencing priming site is attached as well, e.g. by DNA ligation. After DNA isolation, the RV priming site for DNA sequencing is added by PCR. The respective MNs or CAs are identified and quantified through decoding of the manipulation barcode and the MN or CA barcode using DNA sequencing. This process can be adapted to experiments in the presence of molecules (e.g. small molecules or larger biomolecules, such as peptides or proteins) that modulate the activity or function of chromatin interactors and/or modifiers, such as chromatin readers, writers, or erasers or recombinant origin or derived from nuclear cell extracts.

The experiment barcode unambiguously encodes each biochemical or biophysical process that the MN or CA variant has undergone over the course of the experiment. The mononucleosomes and synthetic chromatin array libraries differ from nucleosomes and chromatin arrays previously isolated from nature in many ways, for example in that they are synthesized, chemically pure, and contain predetermined histone and DNA modifications in controlled patterns, and having one or more unique barcodes specifying a given mono- or polynucleosome variant. The also comprise strong, defined NPS sequences, as is discussed elsewhere herein, Chromatin obtained from organisms with native substrates has unknown modifications, no barcoding, and is unsuitable for a library of the invention, or for manipulating or tagging as is achieved using the synthetic mononucleosomes and arrays of the invention.

The described DNA barcoding compositions and methods can be utilized (1) to screen for and/or profile molecules that interact with and/or modify MNs and CAs; (2) for discovery and/or profiling of chromatin interactors and/or modifiers and their preferred MN or CA substrate specificity with regard to MN or CA variant; (3) for discovery and profiling of molecules that modulate chromatin interactors and/or modifiers; and (4) for profiling of MN and CA variants with regard to their biochemical and biophysical properties. Methods according to the invention include the following:

(1) Profiling of Chromatin Interactors, Such as Histone Readers and their Preferred Binding for Specific PTM and/or DNA Modification Patterns.

Figure 5:
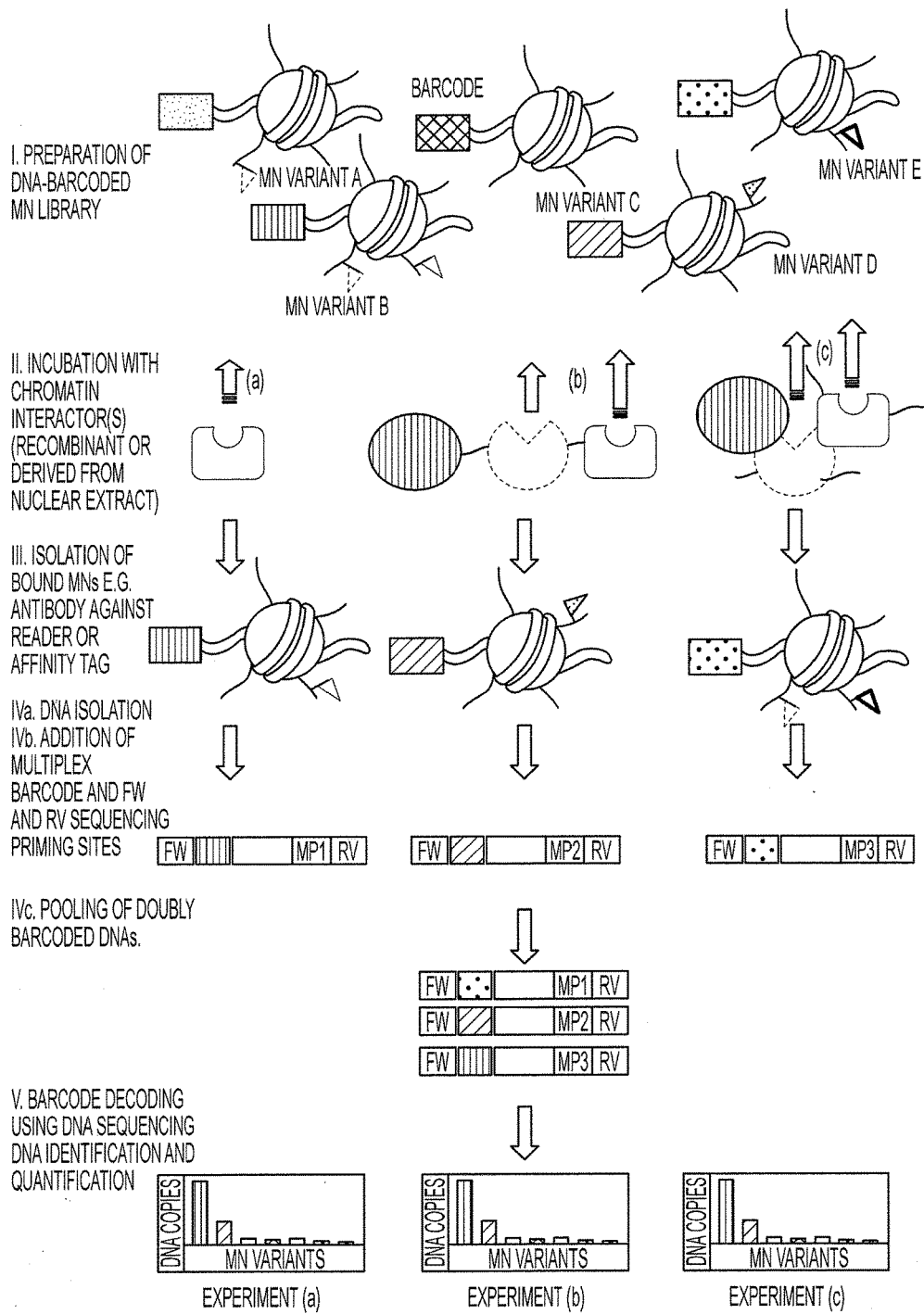
FIG. 5: Example for the use of a barcoded and multiplexed MN library for profiling of chromatin interactors. I. In this particular version, each MN library member is barcoded at the 5'-end of the nucleosomal DNA. The MN barcode encodes the histone variants and/or DNA variants. II. The library is split and incubated with various chromatin readers, such as a reader with one (a) or multiple (b, c) reader modules within one (b) or on different (c) polypeptide chain(s) (recombinant or derived from nuclear cell extracts). III. Isolation of bound MNs, such as by antibody pull-down. IV. Preparation of DNA library for DNA sequencing: IVa. Isolation of barcoded DNA using protein digestion and DNA purification. IVb. Addition of experiment (multiplex) barcode as well as FW and RV sequencing priming sites by PCR (Note: the FW and/or RV priming site can also be included in the nucleosomal DNA prior to MN formation). IVc. Pooling of doubly barcoded DNA sequences. V. DNA sequencing to decode MN and multiplex barcodes. VI. Data analysis for DNA identification and quantification. White: histone octamer; gray: nucleosomal DNA; black protrusions: N-terminal histone tails. The flags represent different modifications as in prior Figures. The different barcodes represent different DNA sequences encoding the respective MN variant. MN: mononucleosomes. MP: Multiplex (experiment) barcode. FW: forward sequencing priming site. RV: reverse sequencing priming site.

A chromatin reader, or versions thereof, e.g. containing either (a) one or (b, c) multiple reader modules (that reside (b) within one polypeptide chain or (c) on different polypeptide chains within a larger protein complex, FIG. 5), is incubated with the barcoded library (in this example, containing a single barcode at the 5'-end of the nucleosomal or array DNA) in solution. As an alternative approach, a nuclear cell lysate of the organism to be studied can be prepared and incubated with the barcoded library. This is followed by isolation of the MN or CA binders, such as by antibody pull-down of the chromatin reader or an affinity tag attached to the reader. After DNA isolation, a second barcode, or multiplex, which encodes the specific (pull-down) experiment ('MP'), as well as the FW and RV priming sites for DNA sequencing are added by PCR. (Note: optionally, the FW and/or RV priming site can also be included in the nucleosomal DNA prior to MN formation). The preferred binders are identified through decoding of the MN or CA and multiplex barcodes using DNA sequencing. Multiple experiments, e.g. using varying protein/MN concentrations, varying readers, truncations or mutants thereof, can be performed in parallel and read-out in a single sequencing step due to the multiplexing PCR step.

Figure 6:
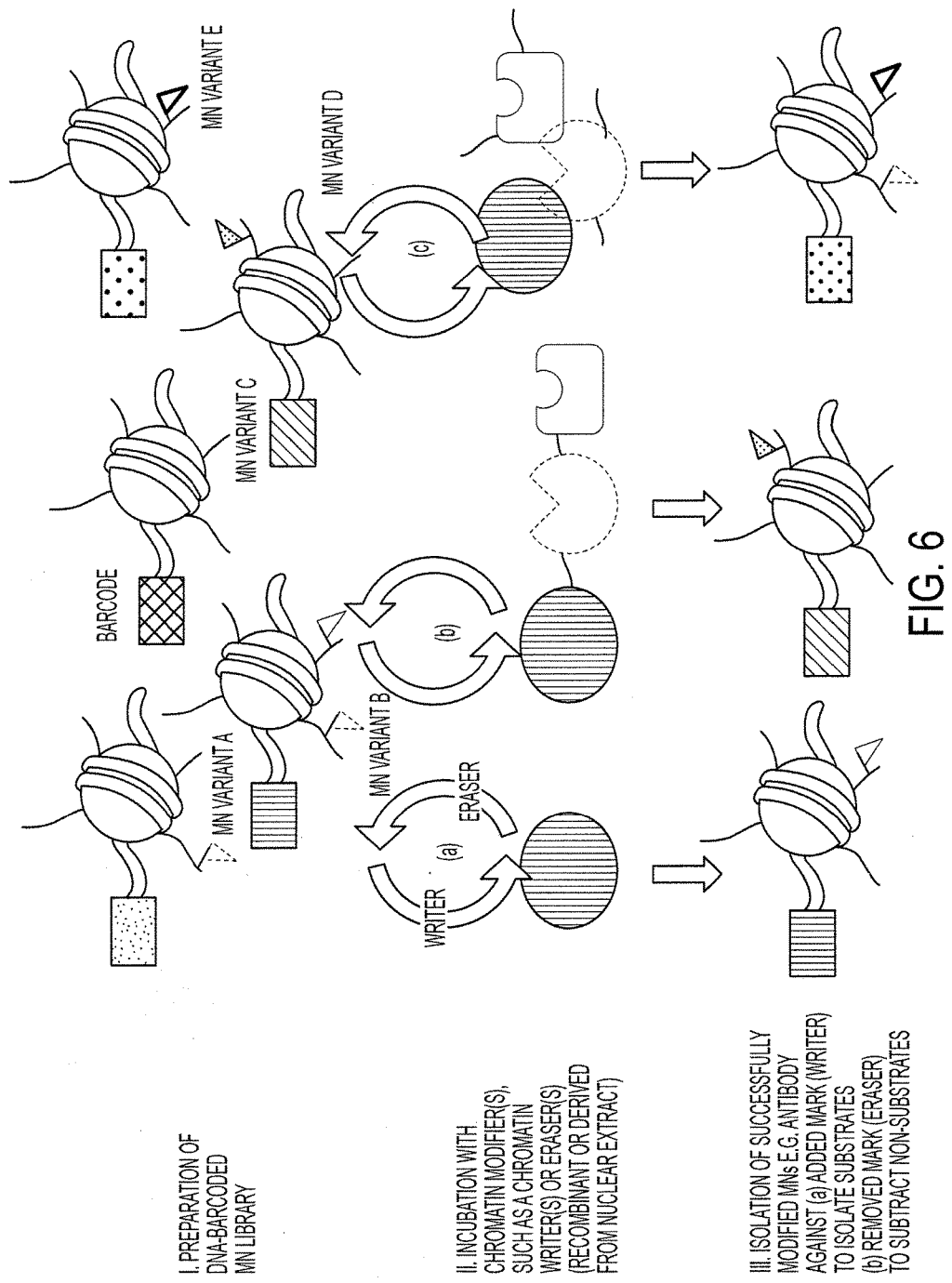
FIG. 6: Example for the use of a barcoded and multiplexed MN library for profiling of chromatin modifiers. I. In this particular version, each MN library member is barcoded at the 5'-end of the nucleosomal DNA. The MN barcode encodes the histone variants and/or DNA variants. II. The library is split and incubated with various chromatin modifiers, e.g. containing the catalytic domain (a), the full-length enzyme (b), or a an enzyme embedded in a large multisubunit complex (c) (recombinant or derived from nuclear cell extracts). III. Isolation of modified MNs, such as by antibody pull-down against (a) the attached mark or (b) the removed mark (in this case, the pull-down is performed to subtract the non-substrates). All further steps are equivalent to the procedure described in FIG. 5. White: histone octamer; gray: nucleosomal DNA; black protrusions: N-terminal histone tails. The flags represent different modifications shown on histones but potentially also on DNA, as in prior Figures. The different barcodes represent different DNA sequences encoding the respective MN variant. H: histone. MN: mononucleosomes. MP: Multiplex (experiment) barcode.

(2) Profiling of Chromatin Modifiers, Such as Histone Writers or Erasers, and their Preferred Substrate Modification Recognition Patterns A chromatin writer or eraser, or versions thereof, such as (a) the catalytic domain, (b) the full-length enzyme, or (c) a large multi-subunit complex (FIG. 6), is incubated with the library (in this particular case, containing a single barcode at the 5'-end of the nucleosomal or array DNA) in the presence of any required substrate, such as S-adenosyl methionine (SAM), Acetyl-Coenzyme A (AcCoA), and adenosine triphosphate (ATP). As an alternative approach, a nuclear cell lysate of the organism to be studied can be prepared and incubated with the barcoded library in the presence of any required substrate, such as SAM, AcCoA, and ATP. This step is followed by isolation of the MN or CA substrates that have been successfully modified by the chromatin writer or eraser, such as by antibody pull-down of the attached or removed mark. In case of a chromatin writer, an antibody against the attached mark is used to pull-down the MNs/CAs that have been modified by the chromatin writer. In case of a chromatin eraser, an antibody against the removed mark is used to subtract the MNs/CAs that have not been targeted by the chromatin erasers, leaving the preferred substrates of the histone eraser behind. After DNA isolation, a second barcode, or multiplex, which encodes the specific experiment, as well as the FW and RV priming sites for DNA sequencing are added by PCR (Note: optionally, the FW and/or RV priming site can also be included in the nucleosomal DNA prior to MN formation). The substrates are identified through decoding of the MN or CA and multiplex barcodes using DNA sequencing. Multiple experiments, e.g. using varying protein/MN concentrations, varying enzymes, truncations or mutants thereof, can be performed in parallel and read-out in a single sequencing step due to the multiplexing PCR step.

(3) Profiling of the Epigenetic Signature of a Cell Line

Using the strategy outlined above, histone modifier activities can be conveniently assayed in nuclear extracts as well. This setup enables identification of chromatin modification activities and specific cross-talks, some of which are characteristic of a given cell type. In particular, cancer cells possess distinct chromatin modification tendencies. For example, EZH2 is a marker of aggressive breast cancer (Kleer et al., 2003), and the ability to measure enzyme activities rather than abundance from tissue samples is of high diagnostic value (Spacil et al., 2013). Barcoded nucleosome libraries are incubated with nuclear extracts from tissue biopsies to catalogue chromatin modification (such as histone and/or DNA modification) signatures for distinct cell types and disease states, thus enabling diagnosis of malfunction of nuclear biochemistry.

(4) Profiling of MN Stability

Figure 7:
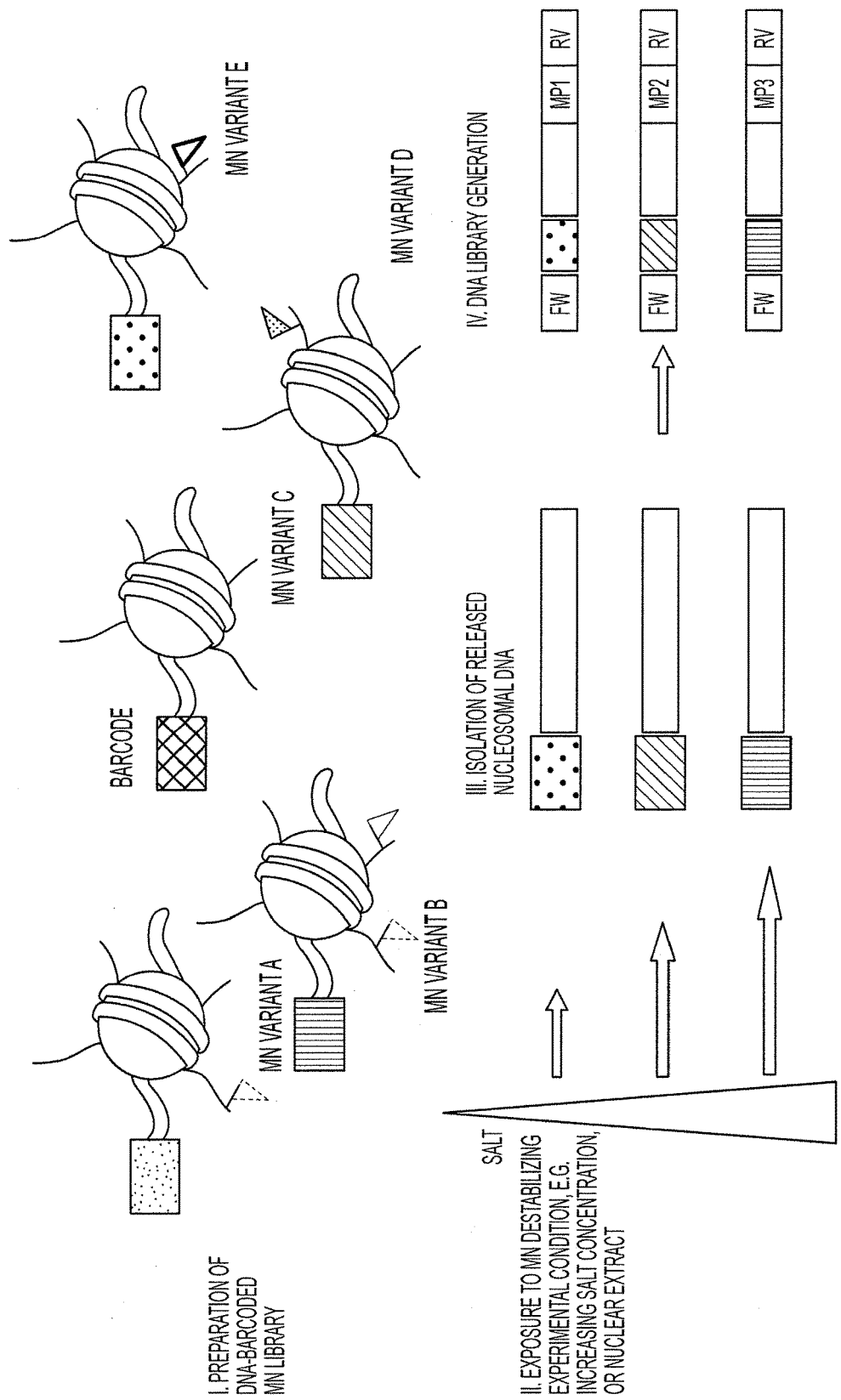
FIG. 7: Example for the use of a barcoded and multiplexed MN library for profiling MN stability. I. In this particular version, each MN library member is barcoded at the 5'-end of the nucleosomal DNA. The MN barcode encodes the histone variants and/or DNA variants. II. The library is split and exposed to various experimental conditions that destabilize MNs, such as increasing salt concentrations or exposure to nuclear cell extract containing chromatin remodeling complexes. III. Isolation of released barcoded nucleosomal DNA, such as by agarose gel purification. All further steps are equivalent to the procedure described in FIG. 5. White: histone octamer; gray: array DNA; black protrusions: N-terminal histone tails. The flags represent different modifications as in prior Figures. The different barcodes represent different DNA sequences encoding the respective MN variant. H: histone. MN: mononucleosomes. MP: Multiplex (experiment) barcode. FW: forward sequencing priming site. RV: reverse sequencing priming site.

The barcoded MN library (in this particular case, containing a single barcode at the 5'-end of the nucleosomal DNA) is exposed to various experimental conditions that destabilize the MNs, such as increasing salt concentrations (FIG. 7). As an alternative approach, a nuclear cell lysate of the organism to be studied can be prepared and incubated with the barcoded library. Nucleosomal DNA release after each salt increment is used to monitor the stability of the respective MNs. After DNA isolation, a second barcode, or multiplex, which encodes the specific experiment, such as the salt concentration used, as well as the FW and RV priming sites for DNA sequencing are added by PCR. (Note: optionally, the FW and/or RV priming site can also be included in the nucleosomal DNA prior to MN formation). The differentially stable MNs are identified through decoding of the MN and multiplex barcodes using DNA sequencing. These stability tests can be extended to experiments in the presence of proteins that modulate MN stability, such as histone chaperones or chromatin remodeling factors, performed in parallel, and read-out in a single sequencing step due to the multiplexing PCR step.

(5) Profiling of CA Stability

A CA library (in this particular case, containing a single barcode at the 5'-end of the array DNA) is exposed to experimental conditions that destabilize the chromatin arrays, such as increasing salt concentrations (in analogy to FIG. 7). As an alternative approach, a nuclear cell lysate of the organism to be studied can be prepared and incubated with the barcoded library. Chromatin DNA release after each salt increment is used to monitor the stability of the respective CA. After DNA isolation, a second barcode, or multiplex, which encodes the specific experiment, such as the salt concentration used, as well as the FW and RV priming sites for DNA sequencing are added by PCR (Note: optionally, the FW and/or RV priming site can also be included in the nucleosomal DNA prior to MN formation). The differentially stable CAs are identified through decoding of the CA and multiplex barcodes using DNA sequencing. These stability tests can be extended to experiments in the presence of proteins that modulate array stability, such as histone chaperones or chromatin remodeling factors, which can be performed in parallel and read-out in a single sequencing step due to the multiplexing PCR step.

(6) Profiling of CA Accessibility

The CA library is exposed to experimental conditions that modulate the folding of the MNs and/or CAs, such as increasing salt concentrations. As an alternative approach, a nuclear cell lysate of the organism to be studied can be prepared and incubated with the barcoded library. The accessibility of the CA library members can be investigated by various ways, such as by recognition of a PTM pattern (e.g. by a histone reader) that is fixed within the CA or by recognition of a DNA binding site such as for a transcription factor embedded within the CA DNA. After DNA isolation, a second barcode, or multiplex, which encodes the specific experiment, as well as the FW and RV priming sites for DNA sequencing are added by PCR (Note: optionally, the FW and/or RV priming site can also be included in the nucleosomal DNA prior to MN formation). The respective CAs are identified through decoding of the CA and multiplex barcodes using DNA sequencing. These accessibility tests can be extended to experiments in the presence of proteins that modulate chromatin array compaction/decompaction, which can be performed in parallel and read-out in a single sequencing step due to the multiplexing PCR step.

Figure 8:
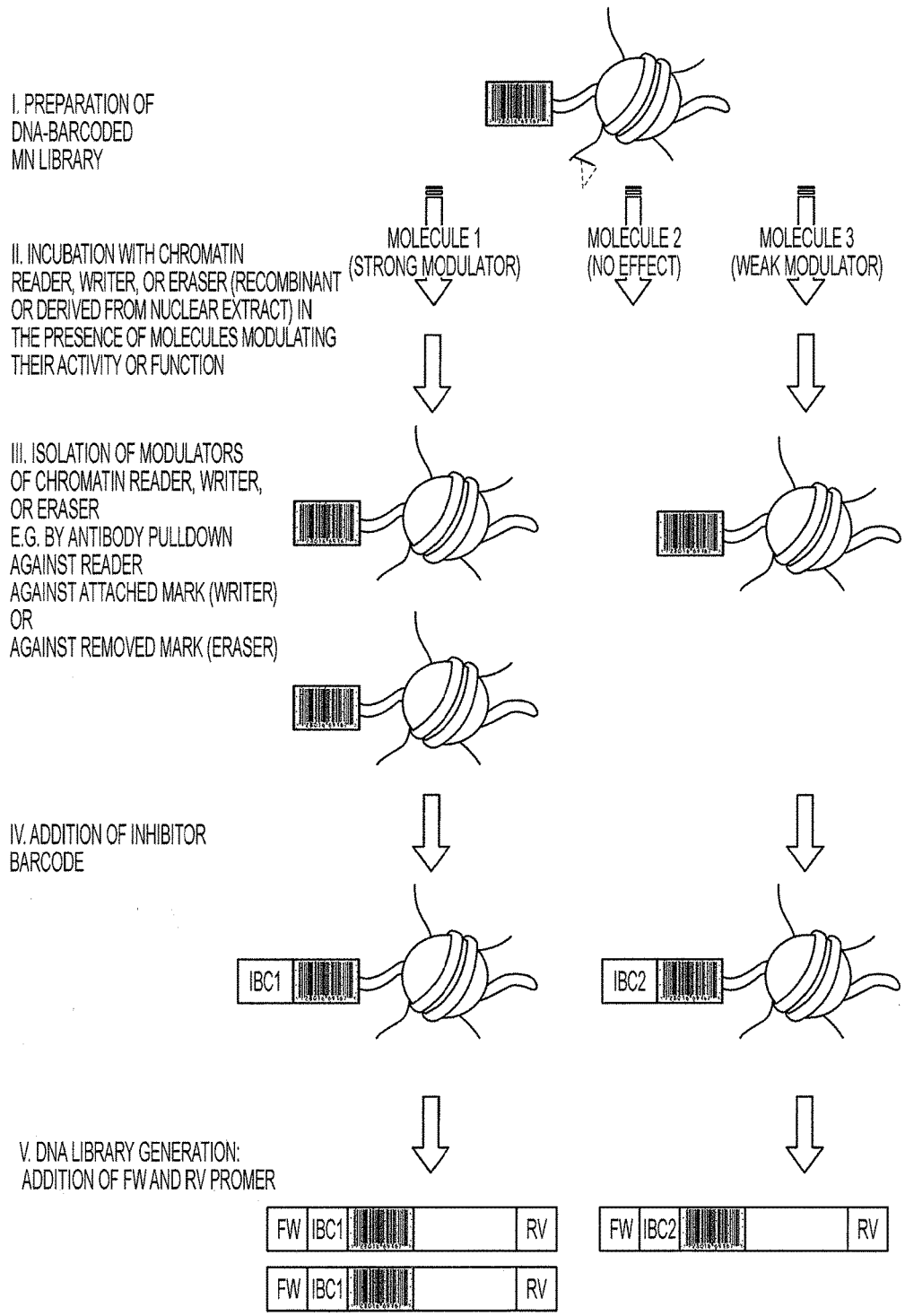
FIG. 8: Example for the use of a barcoded MN library for profiling molecules that modulate the activity or function of chromatin interactors and modifiers. I. In this particular version, only one MN variant is shown, which is barcoded at the 5'-end of the nucleosomal DNA. The MN barcode encodes the histone variants and/or DNA variants. II. The library is split and exposed to various molecules that modulate the function or activity of the chromatin interactors or modifiers (recombinant or derived from nuclear cell extracts). III. Isolation of hits, such as by pull-down against the reader, the attached mark (writer), or removed mark (eraser). IV. Addition of inhibitor barcode (e.g. by DNA ligation). V. DNA library generation: addition of FW and RV primers (by DNA ligation and/or PCR). All further steps are equivalent to the procedure described in FIG. 5. White: histone octamer; gray: nucleosomal DNA; black protrusions: N-terminal histone tails. The flags represent different modifications as in prior Figures. The different barcodes represent different DNA sequences encoding the respective MN variant. H: histone. MN: mononucleosomes. IBC: Inhibitor barcode. FW: forward sequencing priming site. RV: reverse sequencing priming site.

(7) Screening for Molecules Modulating the Activity of Chromatin Interactors and Modifiers, Such as Histone Readers/Writers/Erasers One or several barcoded MNs or CAs are incubated with the chromatin reader, writer, or eraser of interest in the presence of members of a molecular library (e.g. small molecules, peptides, nucleic acids, peptide-nucleic acids, foldamers) containing a putative inhibitor(s) (FIG. 8). The choice of the MN or CA substrates is determined by which reader, writer, or eraser is used in the specific experiment. As an alternative approach, a nuclear cell lysate of the organism to be studied can be prepared and incubated with the barcoded library in the presence of the molecular library. After each incubation step, a barcode encoding the respective candidate molecule used (herein referred to as inhibitor barcode) as well as the FW priming site is added to the 5'-end of the nucleosomal or chromatin DNA. The MNs/CAs are pooled, and isolation of the sub-libraries that showed impaired chromatin interaction or modification as a result of the specific molecule(s) used is performed, such as by pull-down (against (a) the attached or (b) removed mark or (c) the reader). After DNA isolation, the RV priming site for DNA sequencing is added by PCR (Note: optionally, the FW and/or RV priming site can also be included in the nucleosomal DNA prior to MN formation). The hits are identified through decoding of the inhibitor barcode using DNA sequencing.

The following are examples of histone modifications, histone modifiers (including histone writers and erasers), histone readers, DNA modifications and DNA modifiers and DNA readers, as well as cell types that may be used according to the invention.

Histone Readers, Including Proteins Containing the Following Domain(s):
Bromodomain (BD)
Plant homeo domain (PHD)
Tandem PHD
Chromodomain
WD40
Tudor
double/tandem Tudor
MBT
Ankyrin Repeats
zf-CF
PWWP domain ("PWWP" disclosed as SEQ ID NO: 1)
14-3-3
BRCT
UBA
Histone Writers, Including:
Histone acetyltransferases (HATs)
Histone acyltransferases,
Histone methyltransferases (HMTs)
Kinases
Ubiquitinases (UBs)
ADP-ribosyltransferases
Glycosyltransferases
Proline isomerases
Histone remodeling complexes
Histone Erasers, Including:
Histone deacetylases (HDACs)
Histone demethylases (HDMs)
Deubiquitinases (DUBs)
Phosphatases
Arginine deiminases
DNA Modifiers, Including:
DNA methyltransferases (DNMTs)
Methyl-cytosine hydroxylases/oxidases (TET family enzymes)
DNA Modification Readers, Including:
Methyl-CpG binding domain (MBD)
SET and Ring-finger associated domain (SRA)
DNA Modifications, Including:
[Cytosine] methylation/methyl cytosine
[Cytosine] hydroxymethylation/hydroxymethylcytosine
[Cytosine] formylation/formylcytosin
[Cytosine] carboxylation/carboxycytosin
[Adenosine] methylation/methyladenosine
[Guanidine] oxidation/oxoguanidine
Thymidine dimerization
Abasic sites
Single-strand nicks
Nuclear Cell Lysates, Including Those Originating from:
Human cells (such as 293-T cells, COR-L23, HEK293, HeLa, Jurkat, NIH-3T3)
Human cancer cells (such as 721, U937, BCP1, A2780, A-549, A431, CML-T1, DU145, H1299, KYO1, MCF-7, Raji, THP1)
as well as cells from any other organisms of healthy or disease origin Approaches that have been used by other investigators to investigate proteins that interact with and/or modify chromatin are described below.

(1) MN or Small CA Libraries Upon Digestion of Chromatin, Typically Using Micrococcal Nuclease (MNase) Treatment This approach is a version of an immunoprecipitation experimental technique called Chromatin Immunoprecipitation (ChIP)(Schones & Zhao, 2008), that is used to investigate;
(a) the interaction between proteins and DNA in the cell
(b) the abundance and localization of proteins, including histones, at specific genomic regions (c) the abundance and localization of specific histone PTMs Typically, endogenous chromatin and its associated proteins are cross-linked in a cell lysate chromatin is digested by MNase to give a library of CAs and/or MNs the proteins or PTM marks of interest are selectively immunoprecipitated, and the associated DNA fragments are purified and their sequence is determined While these types of samples represent large and biologically relevant libraries and provide valuable information on their genomic loci, there are drawbacks of using them for profiling chromatin interactors and modifiers, such as:

(a) the impurity/inhomogeneity of the samples, both within the sample (contamination with endogenous chromatin interacting proteins) as well as among different experiments (library composition difficult to reproduce from experiment to experiment, in part due to scrambling in vitro)

(b) the read-out of the MN or CA composition after pull-down, since their synthetic history is not encoded. The read-out is dependent on either antibodies (against a specific mark or protein), sometimes in combination with mass spectrometry (MS)(Britton, Gonzales-Cope, Zee, & Garcia, 2011). MS, in particular, is a very sensitive unbiased method that does not require any tagging of the library. However, MS can only profile recognition patterns of histone readers/writers/erasers within a polypeptide chain, i.e. PTM patterns within one histone, but cannot couple PTMs that reside on different histones in an intact nucleosomal context. Furthermore, while sensitive, MS does have a detection limit with certain modification such as phosphorylation being especially problematic. MS cannot discriminate between certain modifications, for example symmetric versus asymmetric dimethyl-arginine. Lastly, ion signals detected in MS are not amenable to any kind of amplification (unlike DNA based information), again placing real world practical restrictions on sensitivity.

(2) Chemically Defined N-Terminal Histone Peptide Libraries with Specific PTM Marks Large libraries (containing up to thousands of members) of modified N-terminal histone tail peptides have been synthesized using solid-phase chemistry (Garske et al., 2010) and used to profile several known histone reader domains for their binding of PTM patterns. The construction of peptide libraries is, compared to intact MNs or CAs, simpler, faster (can be automated), and modular (e.g. using a split- and pool technology). Furthermore, all library members can be encoded, e.g. by physical separation on solid support. The identity of the differentially modified peptides can be determined, such as by MS. Proteins interactions with histone PTMs that reside on the histone tails within one polypeptide chain can be screened, whereas interactions with (i) PTM patterns within the globular domains of the histones, on different histones, or on different nucleosomes in a physiological mono- and polynucleosomal setting; and (ii) DNA modification patterns, or (iii) a combination thereof cannot be investigated, such as multivalent binding of chromatin readers to specific PTM patterns in the nucleosomal context.

(3) Chemically Defined Single MNs Containing Specific PTM Patterns

Intact chemically defined MN substrates with a specific PTM pattern have been used in traditional single pull-down experiments to investigate the concept of multivalency of a histone reader, *Bromodomain PHD finger transcription factor* (BPTF) (Ruthenburg et al., 2011). This work showed the importance of the native nucleosomal context for the read-out of histone PTM patterns, but suffered from extremely low throughput and a requirement for hypothesis-based experimental design. Each pulldown experiment investigated the binding event of a single histone reader-MN pair and could not be performed with multiple MN variants at the same time, as proposed in the described invention, since their synthetic history was not encoded to enable the identification and quantification of the preferred binder. A mononucleosome library of two nucleosomes was constructed by Kingston and coworkers (for the purpose of subjecting them to a chromatin remodeling factor) by attaching two different fluorophores, Cy3 and Cy5, to the 5'-end of a NPS (Goldman, Garlick, & Kingston, 2010). The disadvantages of this approach, compared to the described invention, include:

(1) very small nucleosome library size, which is limited by the availability and suitability of orthogonal fluorescent molecules (library size is 2 in the described publication, but could be scaled up to approximately 4)

(2) low sensitivity of the read-out (fluorescence-versus DNA-based read-out), therefore material- and cost-inefficient (3) no experiment multiplexing possible due to fluorescence-based read-out (4) difficult normalization of the data To date, no method has been successfully developed for quantitative high-throughput chromatin biochemistry, which requires the construction of large and diverse but chemically defined mononucleosome or chromatin array libraries to profile chromatin interacting/modifying proteins with an appropriate read-out in an unbiased fashion (Allis & Muir, 2011; Fierz & Muir, 2012).

The compositions and methods according to the invention overcome the disadvantages of the three approaches outlined above and provide a solution for the generation of such designer chromatin libraries, the isolation, identification, and quantification of interacting molecules with desirable properties. The following features may be included:

recapitulation of native chromatin states present in vivo in the form of modified mono- and polynucleosomes homogeneous preparations, resulting in chemically defined, yet native mono- and polynucleosomal substrates stability towards DNA scrambling during nucleosome preparation, processing, and subsequent biochemical assays by using an artificial NPS high-throughput nature of the biochemical assays performed on mono- and polynucleosomal libraries thanks to barcoding strategy (unambiguous encoding of both (a) MN or CA variant and (b) experiment)

sensitive (i.e. amplifiable) and quantitative read-out thanks to PCR step and next generation sequencing It is advantageous to use unique DNA barcodes to encode for the individual biochemical and/or biophysical properties of each MN or CA library member. These barcodes are attached to or included within the respective polynucleosomal DNA sequences.

Traditionally, DNA barcoding is performed on the genomic level, where genes of interest are tagged with unique molecular barcodes to facilitate the identification of respective protein pools through barcode amplification, labeling, and microarray hybridization, as shown in the example of nucleosome probing with synthetic histone H3 and H4 mutants (Dai, Hyland, Yuan, Huang, & Bader, 2008)

The use of barcodes for identification other than on the genomic level has been described for DNA-barcoded chemical libraries (Buller et al., 2010; Clark, 2010; Kleiner et al., 2011), where DNA stretches are introduced as artificial handles to uniquely tag each small molecule library member, and DNA-encoded antibody libraries (Agasti et al., 2012; Krutzik & Nolan, 2006).

The use of barcoded nucleosomes or chromatin arrays according to the invention provides several distinct advantages. For example, the barcodes unambiguously encode the individual MN or CA variant in the library and can be decoded by microarray hybridization or DNA sequencing to obtain quantitative information on the preferred binders or substrates. Additionally, this barcoding strategy can be employed to encode every biochemical or biophysical manipulation performed on a given library in a modular fashion.

Methods of preparing mononucleosome libraries and chromatin array libraries include the following:

(1) Histone Synthesis (a) Wild-Type (wt) and Native Post-Translationally Modified Histones and Versions Thereof Using Described Procedures.

Figure 9A:
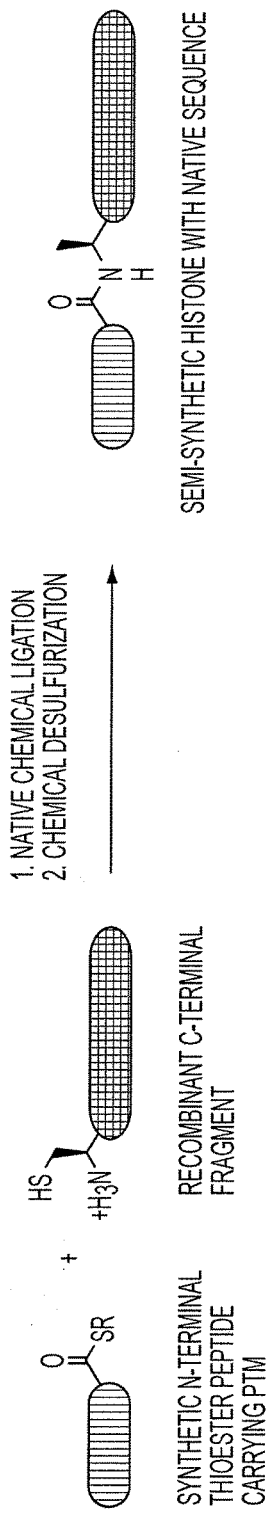
FIG. 9: Overview of histone semi-synthesis and nucleosome assembly. (A) Schematic representation of the semi-synthetic strategy for the preparation of modified histones, in this particular case, N-terminally modified histones. (B) Recombinant wt or semi-synthetic modified histones are combined at equimolar ratios and dialyzed from denaturant to high salt ('Dialysis 1'). Without further purification, a mixture of BC-601 (0.6 eq with respect to histone octamer) and biotinylated MMTV buffer DNA (0.4 eq, with respect to histone octamer; 'BIO-MMTV') is added ('Dialysis 2', high to low salt). Purification of the desired nucleosomes is achieved by streptavidin pulldown (SAP) to remove unproductively formed DNA-histone complexes. MN: mononucleosome; NT: N-terminus; BIO: biotin; SAP: streptavidin affinity purification; PTM: post-translational modification. The sequence of BIO-MMTV at the bottom of the figure is SEQ ID NO: 13.

Recombinant protein synthesis, solid-phase peptide synthesis, or a combination thereof (using technologies such as Native Chemical Ligation (NCL) (Dawson & Kent, 2000), Expressed Protein Ligation (Muir, 2003) (EPL) or amber suppression methods (Wang, Xie, & Schultz, 2006)) are used to synthesize the histone variants that are subsequently incorporated into the MNs or CAs, including wild-type, post-translationally modified, artificially tagged, or truncated histones (FIG. 9a).

(b) Post-Translationally Modified Histones Carrying Methylated Lysine (Kme) or Acetylated Lysine (Kac) Analogs Using Described Procedures.

Cysteine mutants are alkylated to give methylaminoethyl cysteines (Kme analogs)(Simon et al., 2007) or subjected to a thiol-ene reaction to give acetamidoethyl cysteines (Kac analogs)(Cao, Korolev, & Nordenskiold, 2011) using the strategy described by Shokat and coworkers and Nordenskiold and coworkers, respectively.

Synthesis of a single post-translationally modified histone is time consuming but can be expedited through automation and parallelization, such as through the development of modular NCL junctions and protocols, as well as the inclusion of histones containing modified amino acid analogs.

(2) Octamer Formation

Histones are assembled via addition of wt and/or modified histones at equal ratios, dialysis from 6 M GdmHCl to 2 M NaCl, followed by SEC purification (Dyer et al., 2004; Luger, Rechsteiner, & Richmond, 1999). Alternatively, octamer formation can be performed on a scale as little as 1 nmole histone (approximately 50 µg total histone, depending on the histone variant). However, the scale can be increased, if more material is needed, or decreased, as long as appropriate dialysis devices are used to accommodate the volumes used. Concentrations can be measured by UV spectrometry at 280 nm and background subtraction at 300 nm, and calculated extinction coefficients may be obtained by using common websites such as the world wide web site expasy.org/protparam. The histones are mixed at equimolar ratios on ice in approximately 55 µL unfolding buffer (6 M guanidinium chloride, 20 mM Tris-HCl, pH 7.5 at 4° C., 1 mM Na-EDTA, 1 mM DTT) to yield a total protein concentration of about 1 mg/mL at 4° C. The mixtures are placed in mini dialysis buttons (3,500 Da cutoff) and dialyzed against 3×600 mL of refolding buffer (2 M NaCl, 10 mM Tris-HCl, pH 7.5 at 4° C., 1 mM Na-EDTA, 1 mM DTT) for at least 4 h each at 4° C., with one dialysis step overnight. The next day, the mixtures are transferred to a Eppendorf tubes and spun down at 17,000 g for at least 5 min at 4° C. to remove precipitates. Supernatants are transferred into a fresh tube. 50% (v/v) glycerol is added, and the octamer concentrations are measured using their UV absorption and were typically 2-5 µM. The octamers can be directly processed for MN assemblies, and/or stored at −20° C.

(3) Preparation of Barcoded Unmodified and Modified Nucleosomal and Array DNA (a) Nucleosomal and Array Scaffold:

Unmodified DNA can be obtained by known methods such as molecular cloning, PCR, or DNA ligation of pieces thereof, or chemical synthesis. Any DNA sequence can be used, provided that it can direct the nucleosomal positioning, such as the Widom 601 sequence (Lowary & Widom, 1998) used in the presented examples. Various lengths and types of NPS and DNA linkers can be utilized, depending on the application needed. In general, a sufficiently strong NPS is required for successful library member barcoding and identification to avoid DNA scrambling between library members at a concentration of tens of nM (e.g., 5, 10, 20, 30, 40, 50 or more). Modified DNA needs to be synthesized using appropriate methods and, depending on the modification(s) introduced, including enzymatic or chemical methods.

(b) Barcode(s)

One or several barcodes are incorporated anywhere within the nucleosomal or array DNA, at, or near their 5'- or 3'-ends, or within linker regions. The choice and length of the barcode(s) can be adjusted to the specific experiment and extent of combinatorial power needed to encode the entire library. The barcodes encode any biochemical or biophysical property of the library members, such as the histone variant(s), DNA variant(s), MN connectivity, linker DNA, linker histones, non-histone proteins, and/or type of manipulation. For example, as shown in the proof-of-principle experiment described in section 9, a nucleotide stretch of 6 bps can be attached to the 5'-end of the nucleosomal or array DNA, encoding up to 4096 MN or CA variants. These barcodes can be introduced by methods such as:

(i) molecular cloning into plasmid DNA followed by enzymatic restriction to release the nucleosomal or array DNA (ii) PCR (iii) Enzymatic DNA ligations to the 5'- or 3'-end of the nucleosomal or array DNA prior to MN or CA formation (iv) Enzymatic DNA ligations to the 5'- or 3'-end of the nucleosomal or array DNA after MN or CA formation (v) combinations thereof.

(c) FW and RV sequencing priming sites.

If DNA sequencing is used as a read-out, the FW and RV sequencing priming sites can be introduced prior to or after MN, or CA formation or after experiment has been performed, or a combination thereof, using technologies such as molecular cloning, PCR, or DNA ligation.

In one version of barcoded MN libraries (FIG. 10a), a double-stranded (ds) DNA stretch of 190 bps containing a 30 bp FW priming site, compatible with a subsequent next generation sequencing readout using the ionTorrent® sequencer (Rothberg et al., 2011), a 6 bp barcode coding for the MN variant, a 4 bp linker, 147 bps of nucleosomal 601 DNA (Lowary & Widom, 1998), and a short 3 bp appendage at the 3'-end is prepared by PCR using the nucleosomal 601 sequence as a template.

In another version of barcoded MN libraries, a ds DNA stretch of 177 bp containing the Widom 601 nucleosomal DNA (Lowary & Widom, 1998) with an 5'-AA-3' overhang at the 5'-end of the bottom strand and a 5'-CAC-3' overhang at the 3'-end of the upper strand ('BC-601'; FIG. 10b) is prepared by (1) release of the nucleosomal 601 sequence, either cloned as a 12-mer repeat in a circular plasmid or produced by PCR, using BsaI and DraIII; (2) annealing of complementary single-stranded DNA spanning nt 10-30 of the forward ion Torrent priming site ('FW-iT$_{10-30}$')(Rothberg et al., 2011) and the respective 6 bp MN barcodes ('BC-MN'; bottom strand contains 5'-AA-3' overhang at the 3'-end and 5'-CATC-3' overhang at the 5'-end); (3) combining of these hybridized DNA sequences with the nucleosomal 601 DNA; (4) in situ phosphorylation using T4 DNA Polynucleotide Kinase (PNK); (5) ligation using T4 DNA ligase to yield 'BC-601'; and (6) purification of the final DNA product (FIG. 10b). The concentration of the final DNA product is determined by UV absorption of the ds DNA at 260 nm with a subtraction of the background at 340 nm, and calculated extinction coefficients can be obtained by using common websites such as the world wide web site biophysics.idtdna.com/UVSpectrum,html.

(4) MN Formation

Mononucleosomes can be assembled by addition of barcoded nucleosomal DNA to the respective SEC-purified octamer variant, followed by dialysis from high to low salt buffer using described methods (Dyer et al., 2004; Luger et al., 1999). This may be followed by a purification step, such as preparative gel electrophoresis or ion exchange chromatography.

A correct DNA-to-octamer ratio can be determined experimentally for a successful MN or CA assembly (Dyer et al., 2004; Luger et al., 1999). For large scale production where the ratio is predetermined, the process can be expedited by automation.

Alternatively, MN assemblies can be performed in a high-throughput fashion in as little as three days with a new protocol based on the use of buffer DNA, such as the MMTV (Flaus & Richmond, 1998) DNA sequence. A biotin-affinity handle is installed on the 5'-end of the MMTV DNA by PCR (FIG. 9b), which facilitates removal of incorrectly assembled histone-MMTV complexes and potentially free MMTV DNA, and thus eliminates the following time- and material-limiting steps: (1) requirement for purification of the histone octamer prior to nucleosome assembly, such as by SEC; and (2) empirical DNA-to-octamer ratio tests. This new protocol enables material preparation on a very small histone octamer and nucleosome assembly scale (1 nmol of each respective histone, but can be further decreased or increased, if necessary) in a highly parallelized fashion of tens, hundreds, and potentially thousands of nucleosome variants. Typically, nucleosome assemblies are performed on a scale of tens of pmol (e.g., 49 pmol), but this can be scaled up or down, depending on the application needed. Typically, 1 equivalent (eq) (e.g., 49 pmol) of the respective octamers (e.g. from a 39-mer octamer library) is individually combined with 0.6 eq (with respect to octamer of the nucleosomal 601 DNA) (e.g., 29 pmol) of barcoded DNA (BC-601') and 0.4 eq (with respect to octamers) (e.g., 20 pmol) of BIO-MMTV DNA at a concentration of about 0.7 μM octamer (e.g., total volume of about 70 μM pmol) in refolding buffer (10 mM Tris-HCl, pH 7.5 at 4° C., 2 M NaCl, 1 mM EDTA, 1 mM DTT) at 4° C. MN assemblies can be performed using (1) the dilution, (2) the step-wise dialysis, or (3) the continuous dialysis method as described (Dyer et al., 2004; Luger et al., 1999). In this particular case, a continuous dialysis using a peristaltic pump was employed. For example, the MN assembly mixtures can be placed into mini-dialysis buttons and dialyzed against 200 mL MN start buffer (1.4 M KCl, 10 mM Tris-HCl, pH 7.8, 0.1 mM EDTA, 1 mM DTT) for 1 h at 4° C. under stirring. Over a course of approximately 6 h, 320 mL of MN end buffer (10 mM KCl, 10 mM Tris-HCl, pH 7.8, 0.1 mM EDTA, 1 mM DTT) are added at a rate of 1.0 mL/min under stirring, and the mixtures are dialyzed against that resulting buffer for another hour under stirring at 4° C. Subsequently, the mixtures are dialyzed against 2×200 mL MN end buffer (one step for 1 h, the other for at least 4 h under stirring at 4° C.). The mixtures are transferred into Eppendorf tubes, spun down at 17,000 g for at least 5 min at 4° C. to remove precipitates, the supernatants transferred into fresh tubes and supplemented with protease inhibitors, such as 0.5 mM phenylmethylsulfonyl fluoride (PMSF). The assembled MNs are cleared from MMTV DNA (in the free form and/or bound to histones) by incubating the solutions with sufficient amounts of streptavidin coated beads for 1 h at room temperature (RT) on an end-to-end nutator. The solutions are cleared from the beads and spun down at 17,000 g for at least 5 min at 4° C. to remove precipitates. The supernatants are transferred into fresh tubes. Quantification of the final MNs is performed using the absorbance of the ds nucleosomal DNA at 260 nm with a background subtraction at 340 nm. Calculated extinction coefficients can be obtained by using common websites such as the world wide web site biophysics.idtdna.com/UVSpectrum,html. To analyze the quality of the resulting MNs, typically 0.5 pmol of resulting MNs are supplemented with about 15 (v/v)-% sucrose and analyzed by native polyacrylamide gel electrophoresis and staining by EtBr. Visualization is performed using the ImageQuant LAS4000 (GE Healthcare). For storage, 20 (v/v)-% glycerol is added, and the MNs are either split into 3 pmole aliquots, flash-frozen, and stored at −80° C. individually or combined at equimolar ratios, concentrated using a protein concentrator (Vivaspin 500, 10,000 Da cutoff) to approximately 1.0 μM (total nucleosome concentration), split into 3 pmole aliquots, flash-frozen, and stored at −80° C. Overall, nucleosomes can be prepared in as little as three days, starting from recombinant and/or synthetic histones, in a highly parallelized fashion, on the scale of tens, hundreds, and potentially thousands of variants in the described time frame with available robotics.

(5) CA Formation

A uniform array with only one MN subunit type (or variant) can be assembled similarly to (4) above. In a nonuniform array, more than one MN subunit type is present, and the MNs are assembled individually and ligated to one another in a defined sequence using DNA ligation with unique DNA overhangs (Blacketer, Feely, & Shogren-Knaak, 2010). In some arrays, each MN may be unique in its modifications.

(6) MN or CA Library Formation: Pooling of Desired Modified MNs at Desired Concentrations A library can be formed by addition of uniquely DNA-barcoded MNs/CAs to give desired composition of libraries. The ratios of the library members can be either equimolar, or non-equimolar, e.g. to recapitulate the different distributions of MN/CA types, i.e. chromatin states, in vivo.

A purification step can be used to purify the library members, if necessary, e.g. by preparative gel electrophoresis, ion exchange, or gel filtration (Bao, Chakravarthy, Muthurajan, & Luger, 2003). Since the MNs and CAs are barcoded, the resulting pooled library may be purified in one step.

A library may include separate vessels for each MN or CA member, or may include multiple MN or CA members in a single vessel, or may include all members of a library or sublibrary in a single vessel. A library may include both MNs and CAs.

(7) Isolation, Identification, and Quantification of Library Members with Desired Biochemical or Biophysical Properties (a) Biochemical or Biophysical Assay on the Encoded MN/CA Library.

The methods for the biochemical or biophysical assays below are described for MN libraries, but can be applied to CA libraries identically.

(i) Binding Profile of a Chromatin Reader

A chromatin reader (recombinant or derived from a nuclear cell extract) is immobilized on a solid support, e.g. through an affinity tag or immunoprecipitation, and incubated with the nucleosome library in standard protein buffers. These include 2-Amino-2-hydroxymethyl-1,3-propanediol (Tris) buffer, phosphate buffer, and (4-(2-hydroxyethyl)-1-piperazineethanesulfonic acid (Hepes) buffer, at a pH close to neutral (such as 6.5-8), and should contain all reagents and additional cofactors required for (a) nucleosome stability and integrity (such as reducing reagents, protease inhibitors), stability of the chromatin reader (such as glycerol, salts), and (c) for the specificity of the binding event (such as salts, or detergents). The incubation is typically performed at a total nucleosome concentration of tens of nM in a volume of low hundreds of µL, but both numbers can be increased or decreased. Incubation temperature is typically 4° C., but can be anywhere between 4° C. and a temperature that is still tolerated by the nucleosome and chromatin reader, such as 37° C. Incubation time is typically 4 h, when the experiment is performed at 4° C., but can be adjusted to the specific experiment. Alternatively, the binding events between chromatin reader and the nucleosome(s) can be performed in solution first, and immobilization of the chromatin reader-nucleosome complexes can be performed afterwards.

(ii) Enzymatic Modification Pattern of a Chromatin Writer and Eraser

A chromatin writer (recombinant or derived from a nuclear cell extract) is incubated with the nucleosome library in standard protein buffers. These include 2-Amino-2-hydroxymethyl-1,3-propanediol (Tris) buffer, phosphate buffer, and (4-(2-hydroxyethyl)-1-piperazineethanesulfonic acid (Hepes) buffer, at a pH close to neutral (such as 6.5-8), and should contain all reagents and additional cofactors required for (a) nucleosome stability and integrity (such as reducing reagents, protease inhibitors), (b) the enzymatic reaction (such as substrates, e.g. ATP, SAM, and/or AcCoA), (c) stability of the enzymes (such as salts or glycerol), (d) the stability of the reaction products (e.g. inhibitors of the reversal reaction, e.g. HDAC inhibitors when following an histone acetyltransferase reaction), and (e) the specificity of the downstream immunoprecipitation step (such as salts, glycerol, or detergents). The reaction is typically performed at a total nucleosome concentration of tens of nM in a volume of low tens of µL at an appropriate enzyme concentrations, but that can be increased or decreased as desired. Incubation temperature is typically 25-37° C., but can be anywhere between 4° C. and a temperature that is still tolerated by the nucleosome and chromatin writer. Incubation time is typically 10-60 min, when the experiment is performed at 30° C., but can be adjusted to the specific experiment. Subsequently, an antibody binding a enzymatically modified amino acid within the histone sequence is added, typically at a concentration of low tens of µg/mL for 1 h at RT. Subsequently, the antibody-nucleosome complexes are captured by protein G or A beads by incubation for typically 1.5 hours at RT. Alternatively, the binding step between antibody and enzymatically modified nucleosome(s) can be performed in solution, and immobilization of the antibody-nucleosome complexes can be performed afterwards. For an eraser, the nucleosome substrates that were not modified are depleted by immunoprecipitation with an antibody against the removed mark accordingly.

(b) DNA Isolation

Separation of the nucleosomal or array DNA from the associated proteins can be performed by standard methods, such as by protein digestion, such as proteinase K treatment, which is followed by DNA purification (e.g. Qiagen PCR purification kit). The absolute DNA amount can be determined using DNA quantification techniques, such as by UV spectrometry, or hybridization of fluorescent probes, such as Qubit, or qPCR.

(c) Barcode Decoding Using Microarray Hybridization

Decoding can be achieved using a microarray chip with the immobilized DNA sequences using standard procedures (Heller, 2002).

(d) Multiplexing and Barcode Decoding Using DNA Sequencing

The forward (FW) and reverse (RV) sequencing priming sites can be included during nucleosomal or array DNA preparation using methodologies such as PCR, molecular cloning, or DNA ligation. Alternatively, the priming sites may be added after MN or CA formation and the binding or enzymatic experiment using PCR or DNA ligation, enabling simultaneous insertion of a multiplexing barcode encoding a specific experiment. A combination of pre- and post-experimental attachment of priming sites is feasible. The resulting DNA library, thus containing barcodes of nucleosomes with a given biochemical or biophysical property, can be pooled, subjected to a next generation sequencer, and decoding of the sequencing reads (as exemplified by ionTorrent® sequencing in the specific examples shown) can be achieved by sorting the data according to the list of experimental multiplex barcodes first, followed by sorting according to the list of nucleosome barcodes and normalization to the library input, such as by the barcode splitter tool Fastx Toolkit, web site hannonlab.cshl.edu/fastx toolkit/ind3ex.html (FIG. 10d).

Figure 10A:
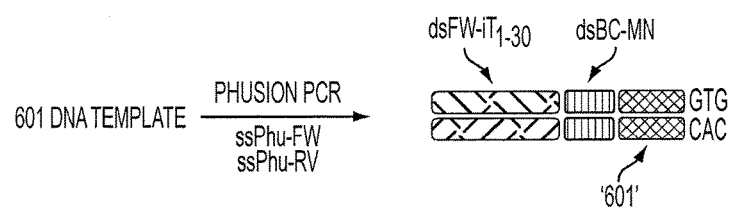
FIG. 10: Generation of multiplexed doubly barcoded DNA sequences for next generation sequencing. (A) Generation of an exemplary barcoded nucleosomal 601 DNA molecules for MN formation (length in this example: 190 bp) by PCR. (B) T4 DNA ligation strategy using appropriate non-palindromic overhangs enables a flexible preparation of barcoded nucleosomal 601 DNA sequence. Complementary single-stranded DNA spanning nt 10-30 of the forward ion Torrent priming site ('FW-iT$_{10-30}$') and the respective 6 bp MN barcodes were annealed, combined with a BsaI-DraIII-digested nucleosomal 601 sequence, in situ phosphorylated using T4 DNA Polynucleotide kinase (PNK), and ligated using T4 DNA ligase. An AA overhang was attached at the 3'-end of the bottom strand to prevent blunt end self-ligation of the 'BC-601' DNA template. (C) DNA experiment multiplexing. Shown is an example for barcoded DNA templates originating from 4 different MN variants and two experiments (EXP1 and EXP2). PCR multiplexing to encode the experimental origin of the MNs is achieved using appropriate reverse primers (containing a common 601 annealing site, '601-RV', multiplexing experiment barcodes 'BC-EXP1' o 'BC-EXP2', as well as the reverse ionTorrent® adaptor 'RV-iT'). The doubly barcoded DNA molecules are pooled, and analyzed using the ionTorrent® next generation sequencer. For decoding and normalization, see (D). (D) Overview of data analysis after ionTorrent® sequencing. In this example, 4 different MNs were subjected to 3 experiments (EXP1-3), with EXP2 being the sequencing of the library input. The raw sequencing reads are first sorted according to their experimental barcodes, followed by sorting according to the MN barcodes. The sorted reads are subsequently normalized against the sequenced input to correct for differences in the initial amounts of each individual MN (middle). The final normalized data is displayed as % input. eq: equivalent; FW: forward; RV: reverse; iT: ionTorrent®; MN: mononucleosome; BC: barcode; EXP: experiment; IP: input; ss: single-stranded; ds: double-stranded. The sequences at the bottom of the figure are, reading from top to bottom, SEQ ID NO's: 14, 10, 15, 11, and 16-18, respectively.
Figure 10B:
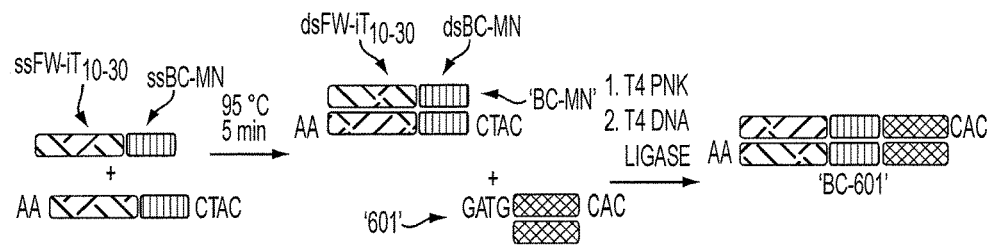
Figure 10C:
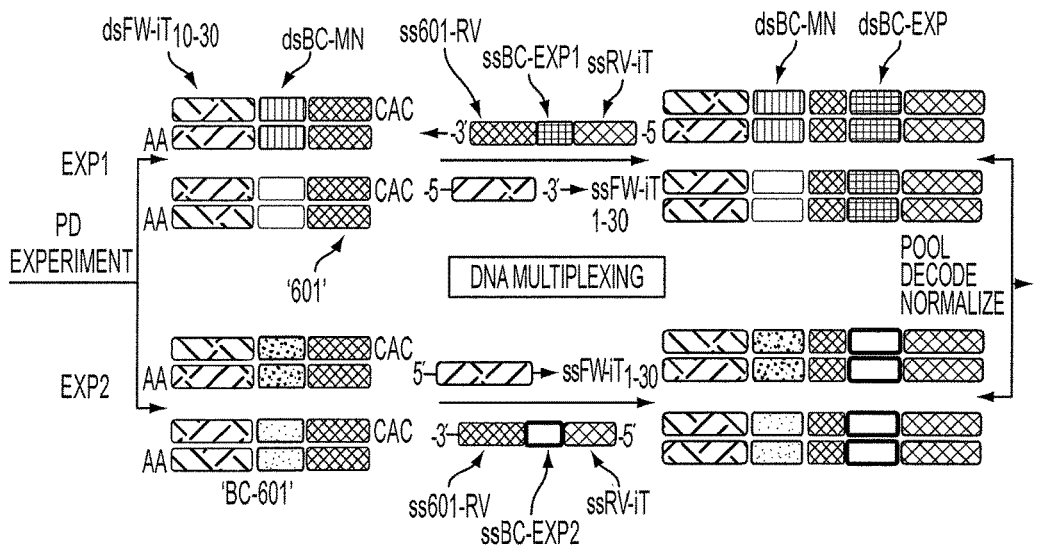
Figure 10D:
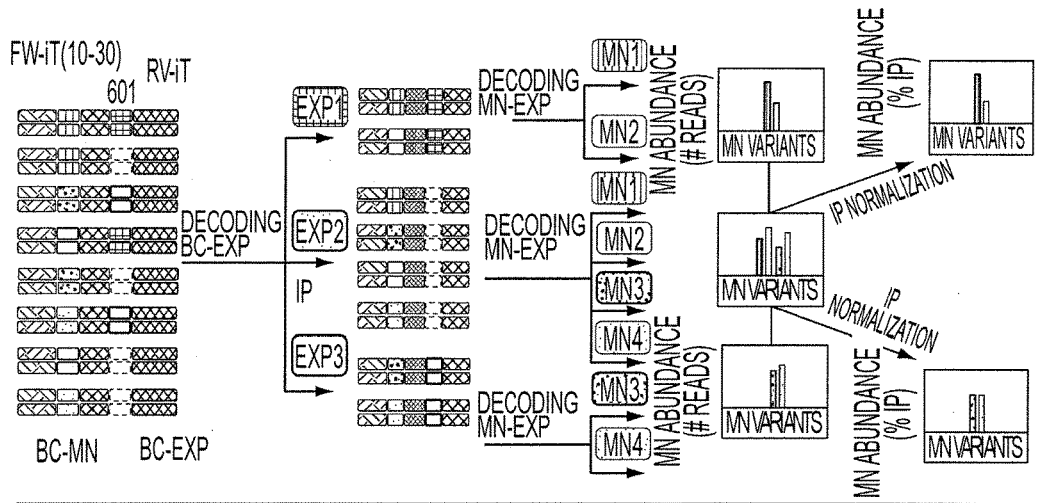
Figure 11A:
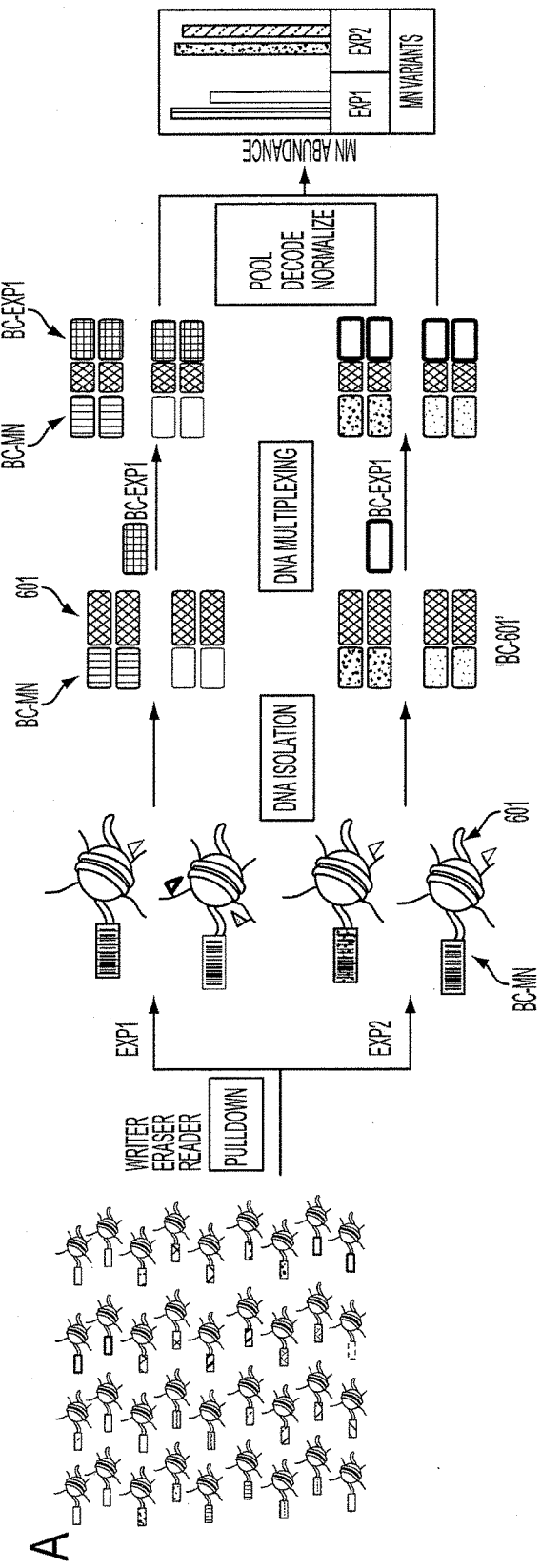
FIG. 11: The encoded nucleosome library enables rapid and detailed investigations of hundreds of nucleosome-chromatin regulator interactions in a short time. (a) A nucleosome library, containing different PTM patterns that are encoded in a 6 bp barcode ('BC-MN') appended on the nucleosomal 601 DNA ('BC-601'), is subjected to a histone writer(s), eraser(s), and/or reader(s) or a combination thereof in form of a nuclear cell extract in multiple separate experiments (shown here: EXP1 and EXP2). Using pulldown experiments, the barcoded nucleosomal DNA of the best binders are isolated, further encoded with multiplexing experiment barcodes BC-EXP1 and BC-EXP2, pooled, decoded using the ionTorrent® next generation sequencer, and normalized against the input. For details on DNA design and preparation, see FIG. 10 A-C. (B) The streamlined workflow enables the equivalent of thousands of experiments (with a library size of 39 subjected to 120 library experiments) in one week, starting from available histones.
Figure 11B:
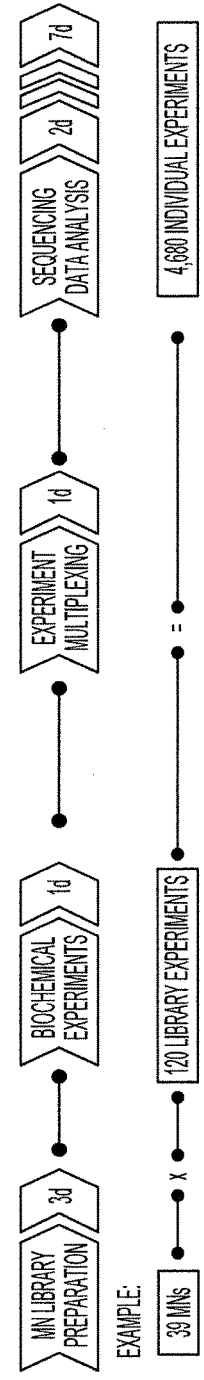

In the embodiment shown in FIGS. 10a and 10b, the FW priming site (compatible with the subsequent next generation sequencing step by ionTorrent® (Rothberg et al., 2011)) is included during the PCR step to generate the barcoded nucleosomal 601 DNA with a 30 bp FW priming site (FIG. 10a) or ligated along with the nucleosome barcode to the 601 nucleosomal 601 building block by T4 DNA ligation ('BC-601', FIG. 10b). After DNA isolation after the appropriate biochemical experiment, the 23 bp RV adaptor priming site compatible with the subsequent ionTorrent® next generation sequencer (Rothberg et al., 2011) as well as the 6 bp multiplex (experiment) barcode as well as the first 10 bp of the ionTorrent® FW priming site are added by a subsequent PCR step (FIG. 10c).

Using DNA sequencing for a readout requires minimal material. However, a certain amount is required to produce the histone octamers and MNs, and for pull down experiments, e.g. using beads, and other techniques that can be used to yield high throughput results. These include implementing microfluidics (Weibel & Whitesides, 2006; Whitesides, 2006) devices to parallelize and miniaturize octamer and MN formation, and also to provide for high throughput operations using the libraries for profiling and screening tests.

Embodiments of the invention include a kit containing defined MN or CA libraries that can be produced and distributed and used to profile chromatin interactors and/or modifiers and to screen for molecules modulating their activity. The kits, compositions, and methods of the invention can be used for the discovery and profiling of existing or new chromatin interactors and/or modifiers; as a diagnostic tool for the analysis of epigenetic signatures of a given cell line, including those derived from human cancer patients; and for the discovery and profiling of existing or new epigenetic drugs.

Using the techniques described here, mononucleosomes and chromatin arrays may be prepared having any desired modifications in type and number, whether to the histone and non-histone protein, the nucleosomal or array DNA, or combinations thereof. With up to about 100 modifications on the histone proteins alone possible, the combinatorics are extremely high. However, only a limited number of the modifications and combinations are biologically relevant. Thus, a selected library may have only 100s of combinations of histone modifications, corresponding to the limited set of biologically relevant modifications typically found in eukaryotes. That is, for efficiency and biological relevance, libraries may exclude non-natural posttranslational histone modifications and non-natural modifications of DNA in mononucleosomes. For example, the modifications may be based on those found in humans and/or yeast.

The mononucleosomes and chromatin arrays may differ from natural chromatin in various ways, including use of a synthetic barcode correlated with the synthesis and modification of the nucleosome or array, a strong synthetic NPS, DNA recognition sites, and/or other synthetic DNA sequences. They have unusually high stability and homogeneity, allowing controlled experiments without confounding variables such as different DNA sequences on each nucleosome, or decoupling of DNA from protein and "scrambling" of the synthetic mononucleosomes. The chromatin arrays may have a precise and predetermined number N of nucleosome units, where N is 2-96. All these features are important for high throughput analysis.

Other aspects of the invention involve the use of computers to analyze the large quantities of data that may be required for some high throughput analyses, such as the analysis of results from large numbers of DNA sequences.

For example, one aspect of the invention is a non-transitory computer-readable medium comprising instructions that, when executed by a computer, cause the computer to
a) identify the presence and location of a barcode of interest coding for the particular experiment (multiplex, or experiment barcode),
b) compare the barcode obtained in a) to a database of barcodes indexed with regard to a particular experiment,
c) identify the presence and location of a barcode of interest in a nucleosome DNA from a synthetic nucleosome that has been interacted with a histone interactor or modifier of interest (e.g., in a DNA sequence obtained by sequencing the DNA from a fixed starting point in the nucleosome DNA),
d) compare the barcode obtained in c) to a database of barcodes indexed with regard to particular patterns of nucleosome modifications in nucleosomes, and
e) identify the pattern of nucleosome modifications associated with the barcode, thereby determining the modification associated with the interactor or modifier.

A skilled worker will recognize additional steps for the computer to perform, or other series of steps for carrying out other methods of the invention.

Another aspect of the invention is a method to establish the nucleosome modification associated with the interactor or modifier of interest, comprising
a) identifying by (on) a computer the presence and location of a barcode of interest coding for the particular experiment (multiplex, or experiment barcode),
b) comparing the barcode obtained in a) to a database of barcodes indexed with regard to a particular experiment,
c) identifying the presence and location of a barcode of interest in a nucleosome DNA from a synthetic nucleosome that has been interacted with a histone interactor or modifier of interest (e.g., in a DNA sequence obtained by sequencing the DNA from a fixed starting point in the nucleosome DNA),
d) comparing the barcode obtained in c) to a database of barcodes indexed with regard to particular patterns of nucleosome modifications in nucleosomes; and
e) identifying the pattern of nucleosome modifications associated with the barcode, thereby determining the modification associated with the interactor or modifier.

Another aspect of the invention is a system for establishing the nucleosome modification associated with the interactor or modifier of interest, comprising
memory and
a processor configured to
a) identify the presence and location of a barcode of interest coding for the particular experiment (multiplex, or experiment barcode),
b) compare the barcode obtained in a) to a database of barcodes indexed with regard to a particular experiment,
c) identify the presence and location of a barcode of interest in a nucleosome DNA from a synthetic nucleosome that has been interacted with a histone interactor or modifier of interest (e.g., in a DNA sequence obtained by sequencing the DNA from a fixed starting point in the nucleosome DNA),
d) compare the barcode obtained in c) to a database of barcodes indexed with regard to particular patterns of nucleosome modifications in nucleosomes (e.g., with regard to the particular experiment, such as a multiplex or an experiment barcode), and
e) identify the pattern of nucleosome modifications associated with the barcode, thereby determining the modification associated with the interactor or modifier.

Figure 17:
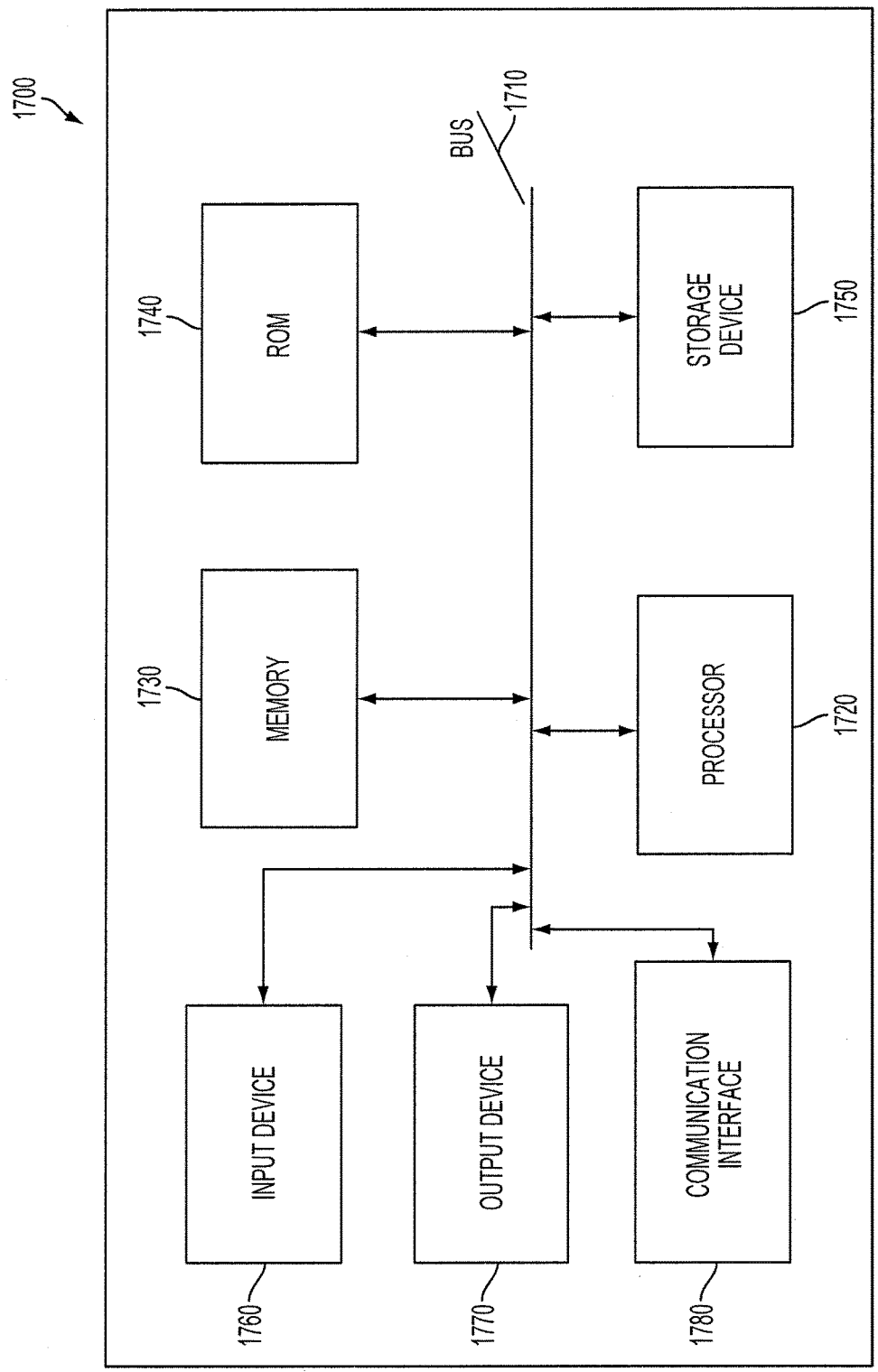
FIG. 17 depicts an exemplary architecture for implementing a computing device in accordance with one or more embodiments.

FIG. 17 depicts an exemplary architecture for implementing a computing device 1700 in accordance with one or more embodiments, which may be used to implement any of the devices, or any other computer system or computing device component thereof. It will be appreciated that other devices that can be used with the computing device 1700, such as a client or a server, may be similarly configured. As illustrated in FIG. 17, computing device 1700 may include a bus 1710, a processor 1720, a memory 1730, a read only memory (ROM) 1740, a storage device 1750, an input device 1760, an output device 1770, and a communication interface 1780.

Bus 1710 may include one or more interconnects that permit communication among the components of computing device 1700. Processor 1720 may include any type of processor, microprocessor, or processing logic that may interpret and execute instructions (e.g., a field programmable gate array (FPGA)). Processor 1720 may include a single device (e.g., a single core) and/or a group of devices (e.g., multi-core). Memory 1730 may include a random access memory (RAM) or another type of dynamic storage device that may store information and instructions for execution by processor 1720. Memory 1730 may also be used to store temporary variables or other intermediate information during execution of instructions by processor 1720.

ROM 1740 may include a ROM device and/or another type of static storage device that may store static information and instructions for processor 1720. Storage device 1750 may include a magnetic disk and/or optical disk and its corresponding drive for storing information and/or instructions. Storage device 1750 may include a single storage device or multiple storage devices, such as multiple storage devices operating in parallel. Moreover, storage device 1750 may reside locally on the computing device 1700 and/or may be remote with respect to a server and connected thereto via network and/or another type of connection, such as a dedicated link or channel.

Input device 1760 may include any mechanism or combination of mechanisms that permit an operator to input information to computing device 1700, such as a keyboard, a mouse, a touch sensitive display device, a microphone, a pen-based pointing device, and/or a biometric input device, such as a voice recognition device and/or a finger print scanning device. Output device 1770 may include any mechanism or combination of mechanisms that outputs information to the operator, including a display, a printer, a speaker, etc.

Communication interface 1780 may include any transceiver-like mechanism that enables computing device 1700 to communicate with other devices and/or systems, such as a client, a server, a license manager, a vendor, etc. For example, communication interface 1780 may include one or more interfaces, such as a first interface coupled to a network and/or a second interface coupled to a license manager. Alternatively, communication interface 1780 may include other mechanisms (e.g., a wireless interface) for communicating via a network, such as a wireless network. In one implementation, communication interface 1780 may include logic to send code to a destination device, such as a target device that can include general purpose hardware (e.g., a personal computer form factor), dedicated hardware (e.g., a digital signal processing (DSP) device adapted to execute a compiled version of a model or a part of a model), etc.

Computing device 1700 may perform certain functions in response to processor 1720 executing software instructions contained in a computer-readable medium, such as memory 1730. In alternative embodiments, hardwired circuitry may be used in place of or in combination with software instructions to implement features consistent with principles of the disclosure. Thus, implementations consistent with principles of the disclosure are not limited to any specific combination of hardware circuitry and software.

Exemplary embodiments may be embodied in many different ways as a software component. For example, it may be a stand-alone software package, a combination of software packages, or it may be a software package incorporated as a "tool" in a larger software product. It may be downloadable from a network, for example, a website, as a stand-alone product or as an add-in package for installation in an existing software application. It may also be available as a client-server software application, or as a web-enabled software application. It may also be embodied as a software package installed on a hardware device.

Numerous specific details have been set forth to provide a thorough understanding of the embodiments. It will be understood, however, that the embodiments may be practiced without these specific details. In other instances, well-known operations, components and circuits have not been described in detail so as not to obscure the embodiments. It can be appreciated that the specific structural and functional details are representative and do not necessarily limit the scope of the embodiments.

Although some embodiments may be illustrated and described as comprising exemplary functional components or modules performing various operations, it can be appreciated that such components or modules may be implemented by one or more hardware components, software components, and/or combination thereof. The functional components and/or modules may be implemented, for example, by logic (e.g., instructions, data, and/or code) to be executed by a logic device (e.g., processor). Such logic may be stored internally or externally to a logic device on one or more types of computer-readable storage media.

Some embodiments may comprise an article of manufacture. An article of manufacture may comprise a storage medium to store logic. Examples of a storage medium may include one or more types of computer-readable storage media capable of storing electronic data, including volatile memory or non-volatile memory, removable or non-removable memory, erasable or non-erasable memory, writeable or re-writeable memory, and so forth. Examples of storage media include hard drives, disk drives, solid state drives, and any other tangible storage media.

It also is to be appreciated that the described embodiments illustrate exemplary implementations, and that the functional components and/or modules may be implemented in various other ways which are consistent with the described embodiments. Furthermore, the operations performed by such components or modules may be combined and/or separated for a given implementation and may be performed by a greater number or fewer number of components or modules.

Some of the figures may include a flow diagram. Although such figures may include a particular logic flow, it can be appreciated that the logic flow merely provides an exemplary implementation of the general functionality. Further, the logic flow does not necessarily have to be executed in the order presented unless otherwise indicated. In addition, the logic flow may be implemented by a hardware element, a software element executed by a processor, or any combination thereof.

EXAMPLES

The following experiments demonstrate the feasibility of the barcoding strategy to encode the composition of MN variants for the identification of the preferred PTM pattern in the nucleosomal context of a histone reader, a histone writer, and the combined histone reading, writing, and erasing activity of a nuclear cell lysate derived from human 293T cells, which can be achieved within one week, starting from available recombinant and/or synthetic histones (11a and b).

A 39-membered library of individually barcoded MN variants, containing combinations of wt histones and/or modified histones H2A, H2B, H3, and H4 (FIG. 12a) was generated.

The wt human histones were expressed in *E. coli* and purified using described methodologies (Dyer et al., 2004; Luger et al., 1999) The modified human H2A, H2B, H3, and H4 histones were prepared using NCL of N-terminal peptides made by solid-phase peptide synthesis and recombinant N-terminally truncated histones with an N-terminal cysteine (FIG. 9a)(Dawson & Kent, 2000; Fierz et al., 2011; Fierz, Kilic, Hieb, Luger, & Muir, 2012) with the following PTMs: lysine ubiquitination (ub) on K119 and K120 for H2A and H2B, respectively, lysine trimethylation (me3) on K4, K9, K27 as well as lysine penta-acetylation (acPoly, K9/14/18/23/27ac) for H3, and lysine mono-acetylation (ac) on K5, K8, K12, K16, K20, as well as lysine penta-acetylation (H4Kac$_5$, K5/8/12/16/20ac) for H4. The proteins were purified by C18 reverse-phase HPLC to a purity of >95%, as judged by ESI-MS. The histones were combined to form 39 nucleosomes with different PTM combinations (for a full list, see FIG. 12b).

T4 DNA ligation was used to attach the MN barcodes, along with nucleotides 10-30 of the FW priming site compatible with the ionTorrent® sequencer (Rothberg et al., 2011), to the nucleosomal 601 DNA sequences at the 5'-end to encode each unique MN variant, resulting in DNA molecules that contained a 20 bp FW priming site (with an single-stranded (ss) 5'-AA-3' overhang at the 3'-end of the bottom DNA strand), a 6 bp barcode (encoding either the respective MN variant), a 4 bp linker (originating from the non-palindromic BsaI DNA ligation site), the 147 bp 601 nucleosomal DNA sequence, and a 3 nt 5'-CAC-3' appendage at the 3'-end of the upper DNA strand as result of DraIII restriction digestion of the 601 nucleosomal DNA (FIG. 10b). In particular, the 147 bp 601 building block containing a 5'-BsaI and a 3'-DraIII overhang was prepared by digestion of a DNA fragment produced by (a) Phusion PCR using a 601 DNA template (Lowary & Widom, 1998) (HPLC purified primers; FW primer: 5'-ACCCTAGGTCTCTGAT-GCTGGAGAATCCCGGTGCCGAGG-3' (SEQ ID NO: 2), RV primer: 5'-CTACCACATCGTGGGATGTATATATCT-GACACGTGCCTGG-3') (SEQ ID NO: 3) or of (b) a plasmid containing 12 copies of the desired sequence (flanked by EcoRV sites on either site; full sequence of 1 repetitive unit: 5'-GATATCACCCTAGGTCTCTGAT-GCTGGAGAATCCCGGTGCCGAGGCCGCTCAATTG GTCGTAGACAGCTCTAGCACCGCTTAAACGCACG-TACGCGCTGTCCCCCGCGTTTTA ACCGC-CAAGGGGATTACTCCCTAGTCTCCAGGCACGT-GTCAGATATATACATCCTGT CACGCGGTGAACAGCGATATC-3') (SEQ ID NO: 4). The PCR product was produced on a 500 mg scale and purified using a Qiagen PCR purification kit. The PCR product was digested at 20° C. for 20 h with BsaI and DraIII (0.5 mg of DNA in a total volume of 0.5 mL containing 100 U/mL of each restriction enzyme) to release the 147 bp 601 sequence, purified using a Qiagen PCR purification kit, ethanol (70 vol.-%) precipitated, redissolved in elution buffer (10 mM Tris-HCl, pH 8.5, EB), quantified by UV spectroscopy at 260 nm with background subtraction at 340 nm ($\epsilon$=2407002 L*mol$^{-1}$*cm$^{-1}$), and stored in aliquots at −80° C. The plasmid was produced in DH5α competent cells on a 1 L scale and purified using a Qiagen Qiafilter Plasmid Giga kit. The plasmid was digested at 20° C. for 20 h with BsaI and DraIII to release the 147 bp 601 sequence (5 mg of DNA in a total volume of 5 mL containing 100 U/mL of each restriction enzyme). The digestion reactions were purified by acrylamide electrophoresis, and precipitation of the purified product using 70 vol.-% ethanol. The pellet was redissolved in EB, quantified by UV spectroscopy at 260 nm with background subtraction at 340 nm ($\epsilon$=2407002 L*mol$^{-1}$*cm$^{-1}$), and stored in aliquots at −80° C. The ds FW-iT$_{10-30}$-BC-MN DNA was produced by hybridizing equal amounts of 5'-CCTGCGTGTCTCCGACTCA-GHXXXXH-3' (SEQ ID NO: 5) (upper strand) and 5'-CATCDXXXXDCTGAGTCGGAGACACGCAGGAA-3' (SEQ ID NO: 6) (bottom strand) by incubation at 95° C. for 5 min and slowly cooled down to RT for 1 h (FIG. 10b). In a typical ligation reaction, 1.25 µM of the 601 building block was combined with 1.1 eq ds FW-iT$_{10-30}$ and incubated with 0.1 U/µL Polynucleotide kinase (PNK) in a volume of 800 µL T4 ligase buffer for 1 h at 37° C. Subsequently, 10 U/µL T4 DNA ligase was added and incubated for 1 h at RT (FIG. 10b). The ligation reaction was monitored by native gel electrophoresis followed by ethidium bromide DNA staining (5% acrylamide gel, 200 V, 40 min; FIG. 12c). The final product was purified using a Qiagen PCR purification kit, eluted with 50 µL EB, and quantified by UV spectroscopy at 260 nm with background subtraction at 340 nm ($\epsilon$=2886629 L*mol$^{-1}$*cm$^{-1}$). The BIO-MMTV DNA was prepared by Phusion PCR using a MMTV DNA template (Flaus & Richmond, 1998) with the following primers: 5'-Biotin-TATCACTTGCAACAGTC-CTAACATTCACCTC-3' (SEQ ID NO: 7) (FW primer) and 5'-ATCCAAAAAACTGTGCCGCAGTCGG-3' (SEQ ID NO: 8) (RV primer). The PCR product was purified using a QIAGEN PCR purification kit followed by precipitation using 70 vol.-% ethanol, redissolving of the pellet in EB, quantified by UV spectroscopy at 260 nm with background subtraction at 340 nm ($\epsilon$=2414925 L*mol$^{-1}$*cm$^{-1}$), and stored in aliquots at −80° C.

Figure 9B:
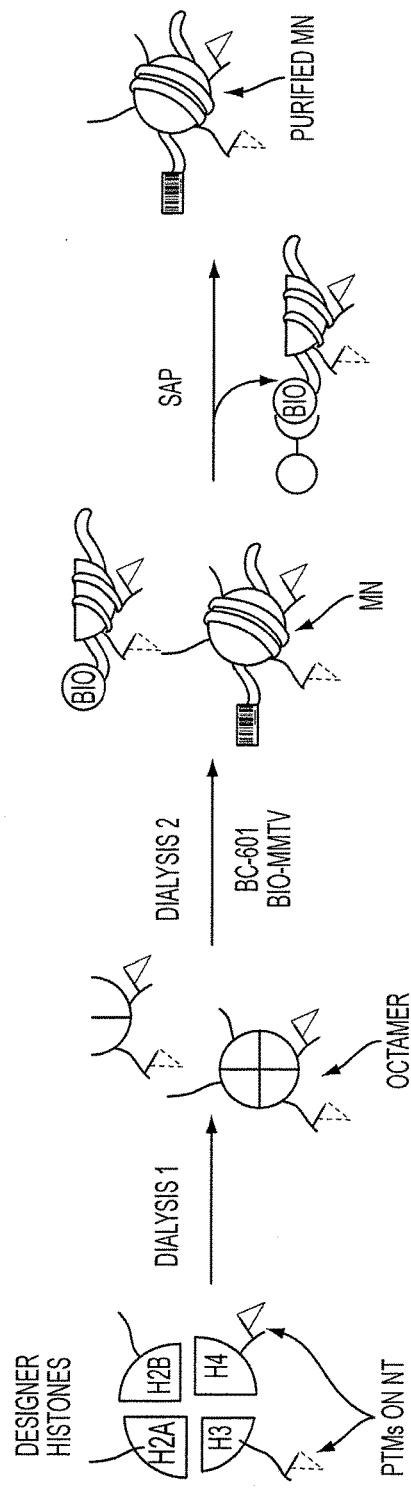

Octamers with the respective histone variants were assembled by refolding stoichiometric amounts of individual histones from GdmHCl on a 1 nmol scale (with respect to each histone variant, approximately 50 µg total histone, depending on the histone variant)) without further purification (FIG. 9b). Concentrations were measured by UV spectrometry at 280 nm and background subtraction at 300 nm (extinction coefficients: $\epsilon_{H2A}$=4470 L*mol$^{-1}$*cm$^{-1}$; $\epsilon_{H2B}$=7450 L*mol$^{-1}$*cm$^{-1}$; $\epsilon_{H3}$=4470 L*mol$^{-1}$*cm$^{-1}$; $\epsilon_{H4}$=5960 L*mol$^{-1}$*cm$^{-1}$). The histones were mixed at equimolar ratios on ice in approximately 55 µL unfolding buffer (6 M guanidinium chloride, 20 mM Tris-HCl, pH 7.5 at 4° C., 1 mM Na-EDTA, 1 mM DTT) to yield a total protein concentration of about 1 mg/mL. The mixtures were placed in mini dialysis buttons (3,500 Da cutoff) and dialyzed against 3×600 mL of refolding buffer (2 M NaCl, 10 mM Tris-HCl, pH 7.5 at 4° C., 1 mM Na-EDTA, 1 mM DTT) for at least 4 h each at 4° C., with one dialysis step overnight. The next day, the mixtures were transferred to a Eppendorf tubes and spun down at 17,000 g for at least 5 min at 4° C. to remove precipitates. Supernatants were transferred into fresh tubes. 50% (v/v) glycerol was added, and the octamer concentrations are measured using their UV absorption ($\epsilon_{octamer}$=35760 L*mol$^{-1}$*cm$^{-1}$) and were typically in the range of 2-5 µM. A fraction of the octamers were directly processed for MN assemblies, and the rest was stored at −20° C. Typical yields were 60-80% to give about 300-400 pmol of histone octamers.

Figure 13:
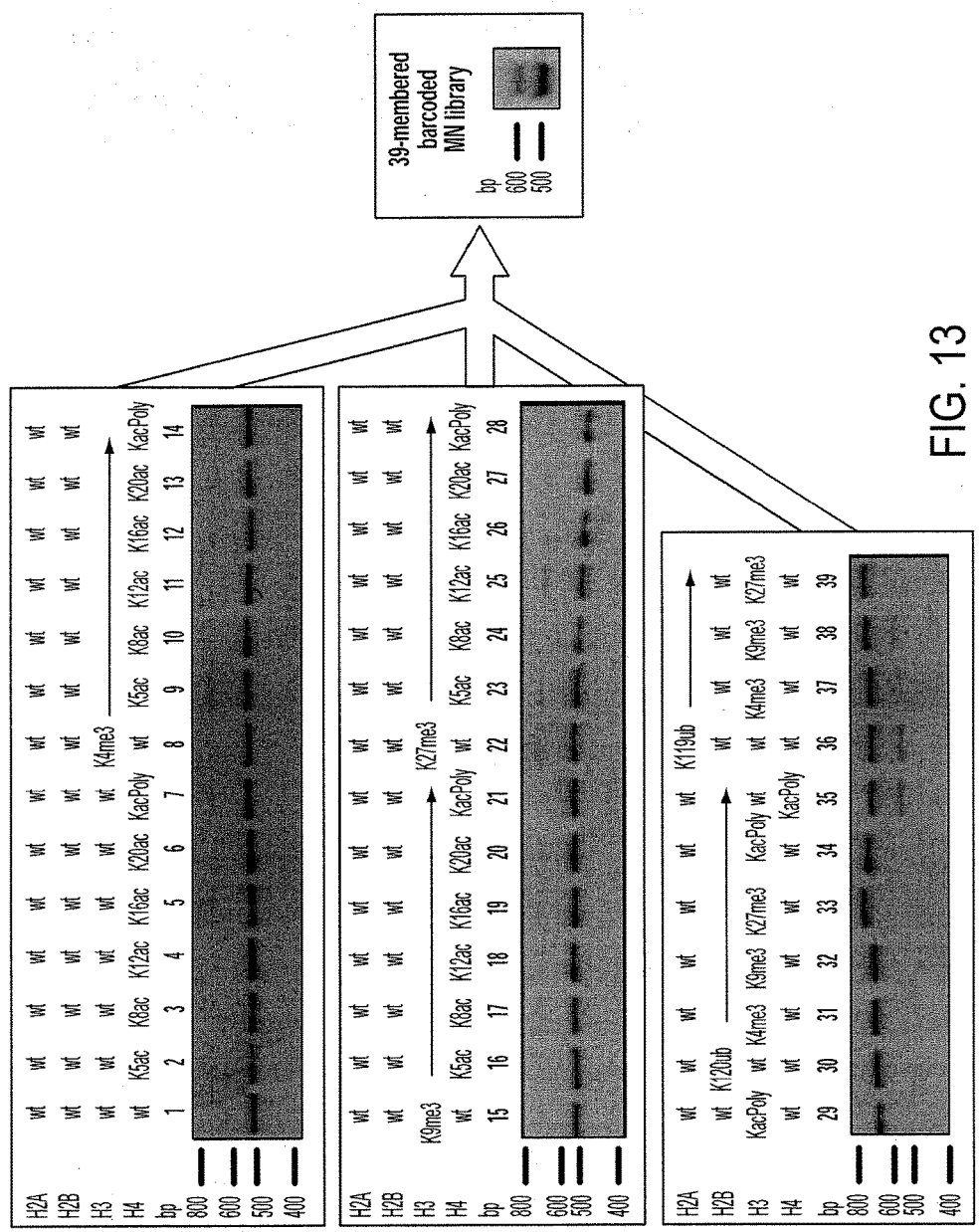
FIG. 13: Analysis of the quality of individual barcoded nucleosome library members by native polyacrylamide gel electrophoresis (PAGE) followed by DNA ethidium bromide staining. All nucleosomes formed a single band (>90% purity) and showed differential gel migration behaviors, depending on the modifications installed on the assembled histone proteins. A native ethidium bromide-stained polyacrylamide gel of the pooled 39mer MN library is shown on the right. ub: ubiquitin; ac: acetyl; me: methyl; wt: wild-type; MN: mononucleosome.

In this particular case, only a fraction of the available histone octamers were used for further nucleosome assembly. Appropriate histone octamers at a concentration of about 1.0 µM in 70 µL reconstitution buffer were combined with 0.6 µM of barcoded 'BC-601' DNA (FIG. 9b) and 0.4 µM of BIO-MMTV buffer DNA at 4° C. The mixture was transferred into a Slide-A-Lyzer MINI dialysis unit and dialyzed at 4° C. against reconstitution buffer containing 200 mL of 1.4 M KCl for 1 h. Subsequently, 330 mL of buffer containing 10 mM KCl were added at a rate of 1 mL/min, followed by two final dialysis steps against reconstitution buffer containing 10 mM KCl (1 h and overnight). Purification of non-productively assembled histone complexes and potentially free BIO-MMTV was achieved by streptavidin affinity purification using 50 uL MyOne Dynabeads (Invitrogen) for 1 h at RT, followed by the addition of 20 vol.-% glycerol and 0.5 mM PMSF. The quality of the nucleosomes was assessed by separation on a 5% acrylamide gel run in 0.5× Tris/Borate/EDTA (TBE) buffer (200 V, 40 min), followed by DNA staining with ethidium bromide (FIG. 13, left). The MNs were quantified by UV spectroscopy at 260 nm with background subtraction at 340 nm ($\varepsilon$=2886629 L*mol$^{-1}$*cm$^{-1}$). The barcoded nucleosomes were combined at equimolar ratios to form the library and concentrated using Vivaspin 500 centrifugal filter units (10,000 Da molecular weight cutoff). The nucleosome library was shock-frozen in aliquots at a concentration of approximately 1 µM and stored at −80° C. Typical yields were close to 60%, resulting in an overall yield of about 40%, starting from the individual histones. For example, 1 nmole of each histone would yield about 200 pmoles of final nucleosomes, which is sufficient for approximately 1000 histone reader binding experiments (see example 1A and 1B), or >10,000 enzymatic histone writer experiments (see example 2 and 3).

Integrity of the pooled MN library after extended storage for >1 month at 4° C. was assessed by native PAGE, followed by ethidium bromide DNA staining (FIG. 13, right). Additionally, the individual nucleosomes were probed for their stability in solution, in particular with respect to DNA scrambling. Therefore, we immunoprecipitated the library with specific antibodies directed against a pre-installed mark, $\alpha$-H3K4me3 (abcam, ab8580). 15 µL of a 30 nM of (total) library nucleosome mixture (i.e. 12 fmoles of each MN variant per antibody pulldown) in buffer (50 mM Tris, pH 8.0, 0.1 mM EDTA, 1 mM PMSF, 100 mM Na-butyrate, 10% glycerol, 1 mM DTT) was supplemented with the $\alpha$-H3K4me3 antibody in a total volume of 100 µL antibody (AB) buffer (20 mM Tris-HCl, pH 7.5, 50 mM NaCl, 5 mM EDTA) to give a final antibody concentration of 15 µg/mL, and incubated at RT for 1 h on an end-to-end rotator. Subsequently, 100 µL AB buffer as well as 10 µL of a protein G bead slurry (Invitrogen) was added, and the mixture was incubated on an end-to-end rotator for 1 h at RT. The beads were washed 4 times with 200 µL AB buffer, and the DNA was eluted using 100 µL of DNA elution buffer (100 mM Tris, pH 7.8, 10 mM EDTA, 1% SDS, 10 mM β-mercaptoethanol (βME), 200 ug/mL proteinase K, NEB) for 1.5 h at 50° C. and purified using the Qiagen PCR purification kit. The resulting pulldown DNA was eluted with 50 µL EB buffer and quantified by the Qubit high sensitivity DNA quantification kit (Invitrogen). The DNA was diluted with H$_2$O to a final concentration of 2 pg/µL (the dilution factors of the respective experiment was considered later during sequencing data analysis, see below). Input samples (10-50% of the initial library input, depending on the experiment) were processed identically. An internal standard mixture for the multiplexing PCR step was produced by Phusion PCR using a 601 template and the following primers: FW: 5'-PCR step was produced by Phusion PCR using a 601 template and the following primers: FW: 5'-CCTGCGTGTCTCCGACTCAGXXXXXXGAT-GCTGGAGAATCCCGGTGCCGAGG-3' (SEQ ID NO: 9) (standard A: CTCAGT, standard B: CATGCT, standard C: TGAGTC, standard D: ACTGCA); RV: 5'-GTGACAGGAT-GTATATATCTGACACGTGCCTGG-3' (SEQ ID NO: 10). The PCR products were purified using a Qiagen purification kit, eluted with DNA EB buffer, quantified using the Qubit high sensitivity DNA quantification kit (Invitrogen), and mixed in EB to a total DNA concentration of 2 pg/µL with the following distribution: 1,000 eq standard A, 100 eq standard B, 10 eq standard C, and 1 eq of standard D.

In a typical multiplex PCR reaction, 9 pg of each pulldown DNA was combined with 1 pg of the internal standard mixture in the presence of 0.01 U/µL Phusion, 0.2 mM dNTPs, 0.5 µM of each of the FW primer (FW-iT: 5'-CCATCTCATCCCTGCGTGTCTCCGACTCAG-3') (SEQ ID NO: 11) and the respective barcoded RV primer (RV-601-BC-EXP-RV-iT: 5'-CCTCTCTATGGGCAGTCG-GTGATBXXXXDGGTGCTAGAGCTGTCTACGAC-CAATTG AGC-3' (SEQ ID NO: 12); PCR cycle program: initial denaturation, 30 s/98° C.; denaturation, 10 s/98° C.; annealing, 15 s/62° C.; extension, 5 s/72° C.; 15 cycles total; final extension, 7 min/72° C.; FIG. 10c). The PCR products were purified using a Qiagen PCR purification kit and eluted with 50 µL EB. The multiplexed DNA sequences were pooled at equal volumes and sequenced using an Ion Torrent Personal Genome Machine according to the manufacturer's instructions (Merriman, R D Team, & Rothberg, 2012; Rothberg et al., 2011). For data analysis, the raw sequencing reads were first sorted according to the 3' experimental barcodes. Subsequently, the reads were sorted according to the 5' MN barcodes (FIG. 10d). The individual reads of each MN variant were multiplied by the DNA dilution factor of the DNA sample of the respective pulldown experiment. Finally, these corrected reads were normalized against the reads of the individual MNs of the library input (averaged from at least 2 input samples). The resulting values represented the pulldown efficiencies of the individual MNs expressed as % input in the respective experiment. In some cases, the pulldown efficiencies were further normalized against the pulldown efficiency of one variant.

Figures 14A, 14B:
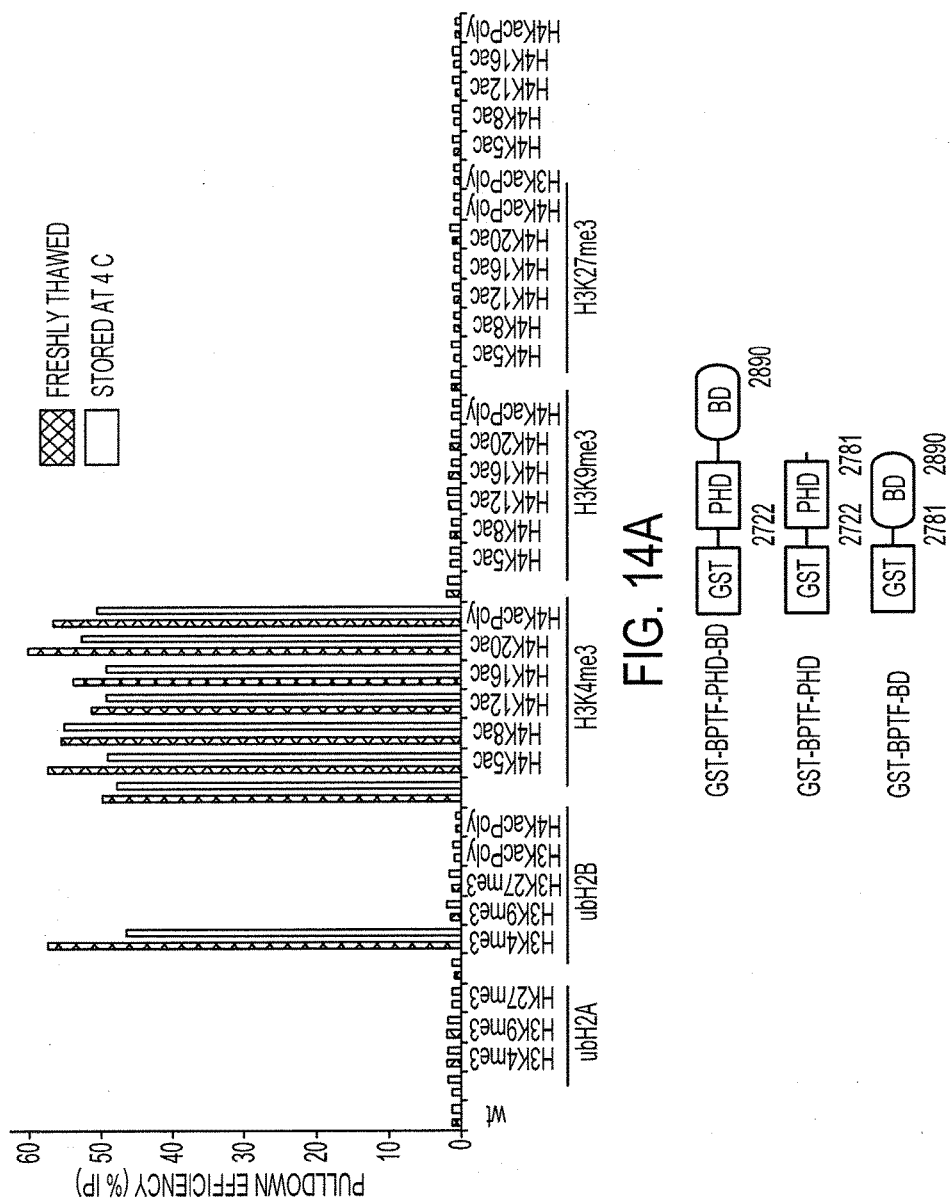
FIG. 14. Profiling of MN library using modification-specific antibodies and the histone reader 'Bromodomain Plant Homeodomain (PHD) finger transcription factor BPTF'. (A) The stability of the barcoded MN library was tested by immunoprecipitation of the library using an α-H3K4me3 antibody (ab8580). No DNA scrambling was observed (cross hatched) even after extended storage at 4° C. (white). (B) Recombinant N-terminally GST-tagged BPTF constructs employed in this study. N-terminally GST-tagged constructs were expressed recombinantly in *E. coli* and purified by glutathione affinity, ion exchange, and size exclusion chromatography. The purity of the proteins was assessed by SDS-PAGE followed by CBB staining. (C, D) GST pull-down of the barcoded nucleosome library using BPTF constructs. Resin-bound BPTF-PHD (C), BPTF-PHD-BD (D, left) and BPTF-PHD (D, right) were probed against the 39 nucleosome variants. Processing of the data was performed as shown in FIG. 10C, D, and the input-normalized sequencing reads were further normalized against the H3K4me3 variant (set to 1 and indicated as *; (mean±SD) % input value is shown in the inset). IP: input; GST: glutathione-S-transferase; PHD: plant homeodomain; BD: bromodomain; CBB: Coomassie brilliant blue.

Only nucleosomes carrying a H3K4me3 barcode were isolated when an $\alpha$-H3K4me3 antibody was used in the pulldown (50-60% pulldown efficiency compared to input); those equipped with different PTMs were bound at background levels only (less than 0.5% pulldown efficiency compared to input), suggesting that DNA exchange among the library members was not observed, even when the library was exposed to freeze-thawing cycles or extended storage for months at 4° C. (FIG. 14a).

Example 1A

Profiling of two adjacent histone reader modules of a recombinantly expressed Bromodomain Plant Homeodomain (PHD) finger transcription factor BPTF: With a diversely modified and stable nucleosome library in hand, we sought to profile the binding properties of BPTF. Since our collection of MNs covered variants that had not been investigated previously in the context of BPTF (Ruthenburg et al., 2011), such as those carrying Kac$_5$ on H3 or H4, Kme3 at positions 9 and 27 on H3, or Kub on H2A and H2B (FIGS. 12a and b)(Ruthenburg et al., 2011), the library allowed us to systematically interrogate BPTF's multivalent nucleosomal binding behavior with a larger substrate sampling size. Additionally, experimental variations were minimized as all nucleosomes were probed for BPTF binding simultaneously in one single experiment, a unique key advantage of barcoded nucleosomes.

Figure 14C:
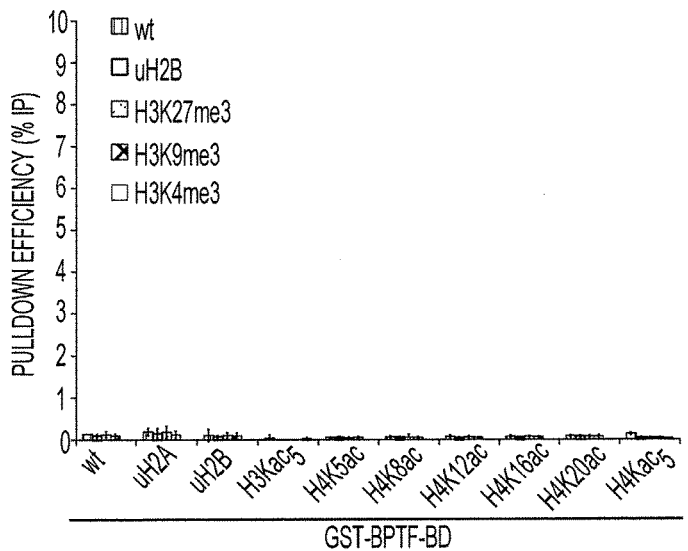
Figure 14D:
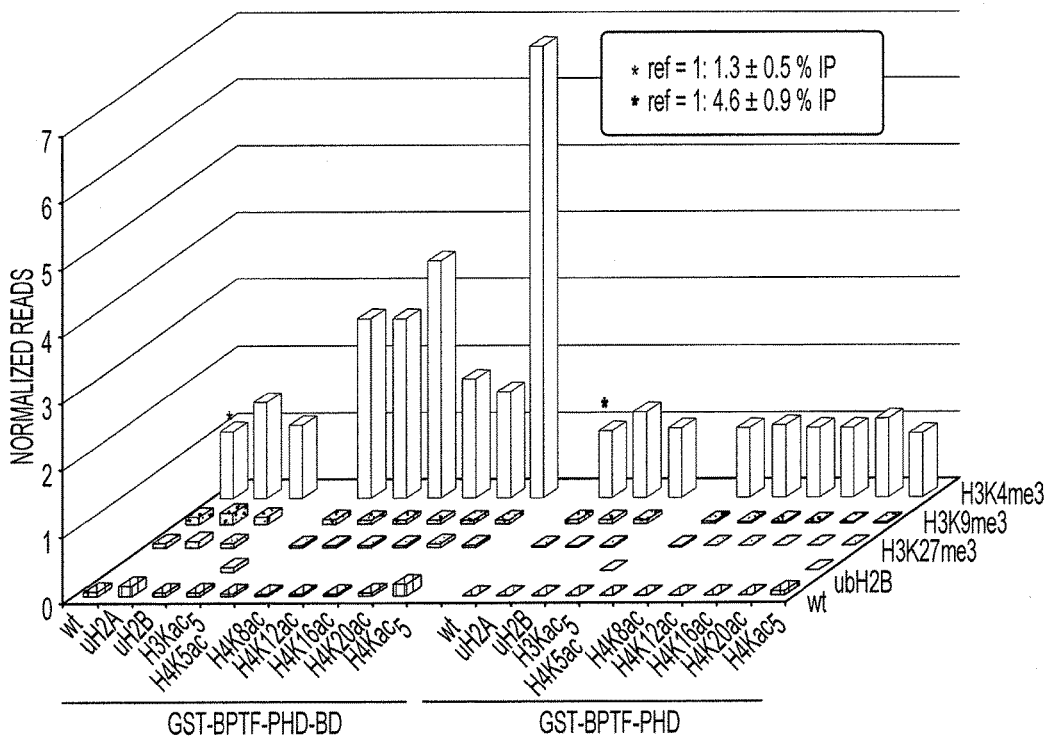
Figure 15A:
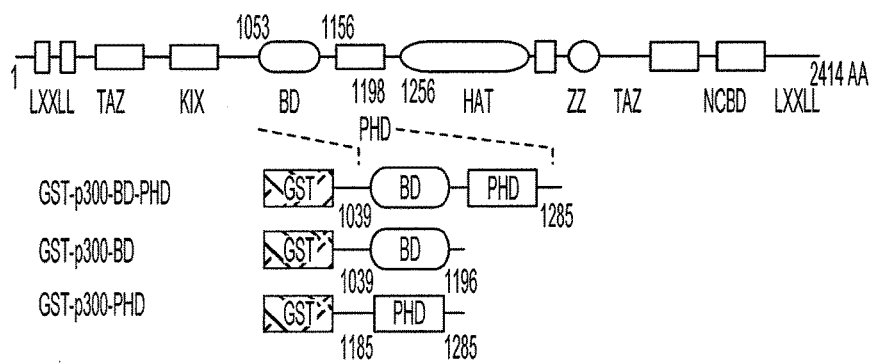
FIG. 15. Profiling of MN library using the histone reader and writer p300. (A) Recombinant N-terminally GST-tagged p300 constructs employed in the library binding experiment. N-terminally GST-tagged constructs were expressed recombinantly in *E. coli* and purified by glutathione affinity, ion exchange, and size exclusion chromatography. The purity of the proteins was assessed by SDS-PAGE followed by CBB staining. (B, C, D) GST pull-down of the barcoded nucleosome library using the GST-tagged p300 constructs. Resin-bound GST-p300-BD-PHD (B, left), GST-p300-BD (B, right), and GST-p300-PHD (C) were probed against the 39 nucleosome variants. This was followed by DNA isolation, purification, multiplexing using the reverse experimental multiplex barcodes, sequencing using the ionTorrent® technology, decoding, and input normalization as described in FIG. 10 C, D. The input-normalized sequencing reads were further normalized against the H4Kac$_5$ variant (set to 1 and indicated as *; (mean±SD) % input value is shown in the inset). IP: input; GST: glutathione-S-transferase; PHD: plant homeodomain; BD: bromodomain; CBB: Coomassie brilliant blue.
Figure 15B:
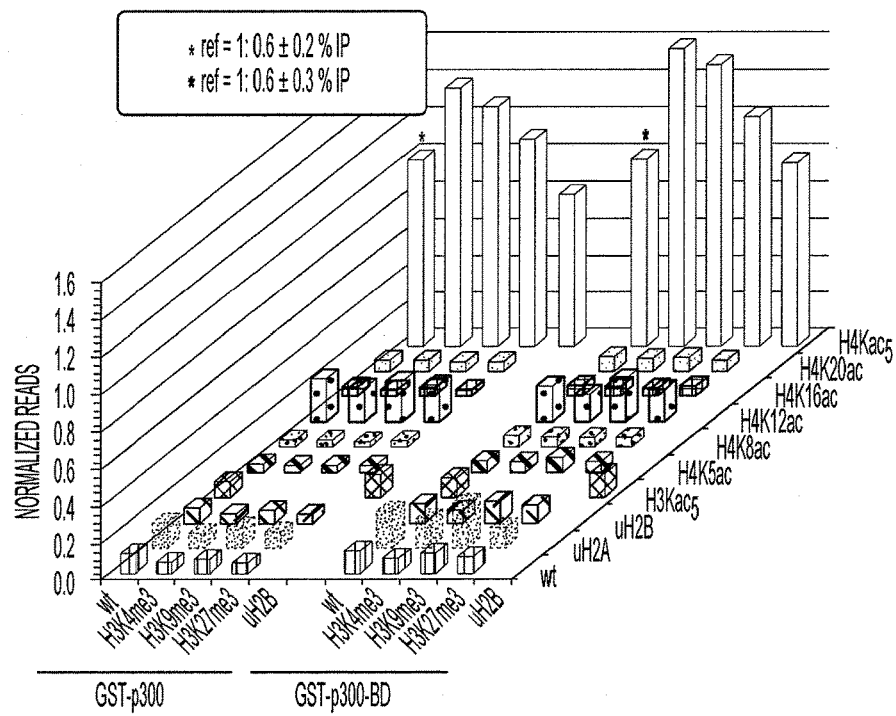
Figure 15D:
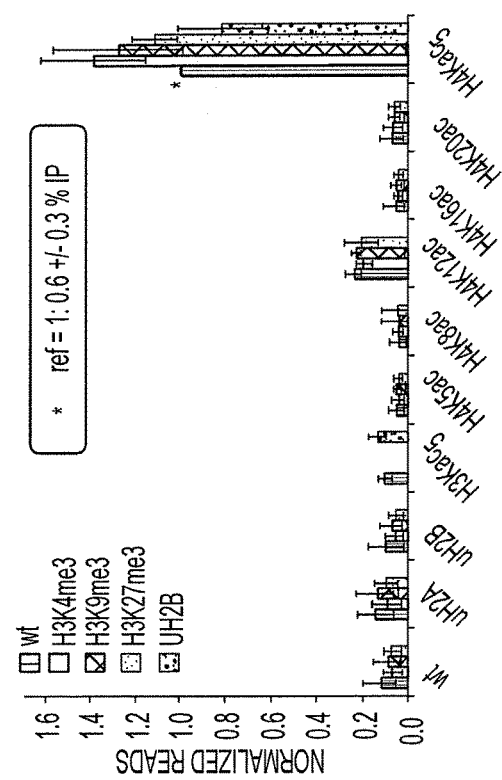
Figure 15C:
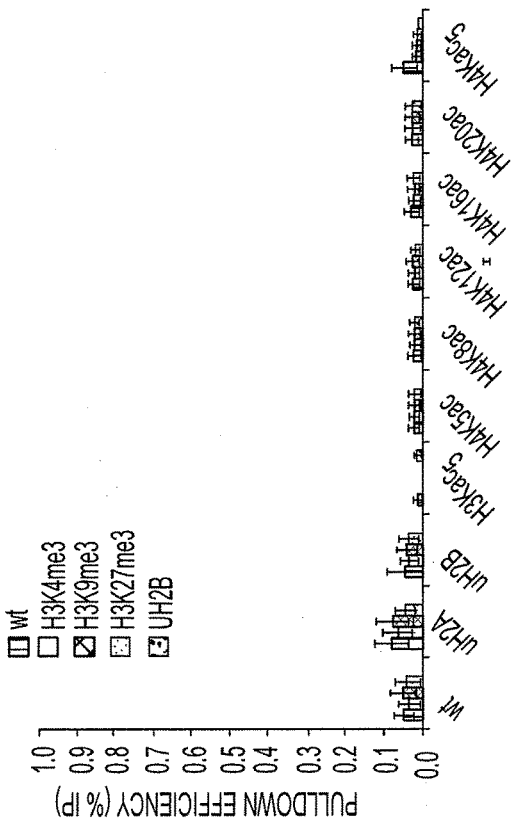

An excess of N-terminally fused glutathione-S-transferase (GST) BPTF constructs containing either the coupled PHD-BD module or the respective single domains (approximately 200 pmoles, FIG. 13b) were immobilized on 3 µL of a glutathione resin slurry (1 h, RT) and incubated with the encoded nucleosome library (0.125 pmoles of each MN variant) in a volume of 200 µL in GDP300 buffer (20 mM HEPES, pH 7.9, 30 mM KCl, 20% w/v glycerol, 0.2 mM EDTA, 1 mM DTT, 0.01% NP-40; final nucleosome concentration: 24 nM) for 4 h at 4° C. on an en-to-end nutator. The beads were washed 4 times with 200 µL of GDP300 buffer. DNA isolation, purification, multiplexing, decoding, and normalization were performed as described above. GST-tagged BPTF-BD did not interact with acetylated nucleosomes under the conditions tested, which is consistent with results from previous work (FIG. 14c). In contrast, GST-tagged BPTF-PHD recognized nucleosomes trimethylated on H3K4, independent of whether other marks were present in the same nucleosome or not. No binding was observed when either Kme3 was installed at other positions within the H3 tail or the bulky Kub mark was attached to H2A or H2B (FIG. 13d, red, right). When the double PHD-BD domain was used as a bait, all nucleosomes with H3K4me3 marks were isolated, while those carrying only acetylated lysine(s) were not (FIG. 13d, red, left). However, the coexistence of H3K4me3 and H4Kac within the same nucleosome enhanced the binding efficiency by 1.5-3.5-fold (single marks at K5, K8, K12, K16, or K20) compared to H3K4me3 alone (FIG. 13d, red). A 2-3-fold increase in nucleosomal binding had been observed previously with nucleosomes modified with H3K4me3-H4K16ac, and the contribution of Kac to multivalency was less pronounced at adjacent sites in the H4 tail (Ruthenburg et al., 2011). In our case, this positional dependence is flattened out while a strong enhancement of about 7-fold was found with H4Kac$_5$-containing nucleosomes, a variant that had not been previously characterized (FIG. 13d, red). Since the Kac-binding pocket of BPTF's BD can only accommodate one acetylated lysine, the enhanced affinity is likely to be a consequence of binding avidity resulting from multiple acetylated lysines in the H4 tail. We verified these findings using traditional isolated pulldown experiments and found similar binding behaviors Example 1B Profiling of two adjacent (potentially) histone reader modules of a recombinantly expressed histone acetyltransferase p300: Having demonstrated the ability of our technology to rapidly scrutinize the multivalent binding behavior of BPTF, we decided to extend the investigation to the transcriptional coactivator p300. Recombinant GST-tagged p300-BD-PHD (FIG. 15a) was incubated with the nucleosome library as described in example 1B. Nucleosome binder isolation, DNA isolation, purification, multiplexing, decoding, and normalization were performed as described above. Although nucleosome binding was weaker than for BPTF under the conditions used, robust association of the GST-tagged p300 BD-PHD module with H4Kac$_5$-containing nucleosomes was detected (FIG. 15b, red). Since additional Kme3 marks did not corroborate or weaken the strength of association, this new finding proposes that the PHD finger does not bind to either trimethylated or unmodified H3K4. In order to break down the individual contributions of the BD and PHD finger for association with acetylated nucleosomes, we repeated the experiments with each domain alone. While the PHD finger showed no detectable interaction to any nucleosome variant (FIG. 15c), the BD displayed a similar binding behavior as the BD-PHD module (FIG. 14d), suggesting that the PHD finger is dispensable for this association. Together with earlier reports, our library pulldown data led us to generate the hypothesis that p300 may operate via a positive feedback loop either by binding to its own marks and/or by a Kac-mediated allosteric regulation, potentially through its BD. Our developed technology is highly suitable to directly test such theory due to its modularity and ability to combine binding with enzyme assays using the same nucleosome library.

Example 2

Figure 16A:
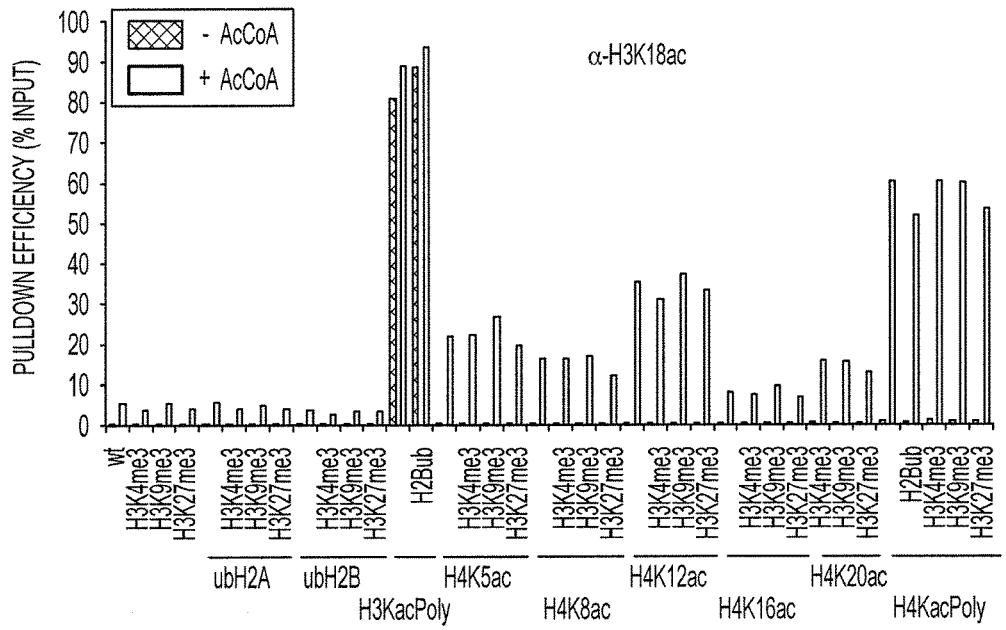
FIG. 16. Profiling of histone writing activity of p300 and of a nuclear cell extract using the barcoded MN library. (A, B) The barcoded 39-mer library was subjected to p300 acetylation in the absence (cross hatched) or presence (white) of acetyl-coenzyme A (A). The extent of site-specific acetylation was assessed by immunoprecipitation of reaction products using antibodies directed towards H3K18ac (A) or H4K5ac (B), followed by DNA isolation, purification, multiplexing using the reverse experimental multiplex barcodes, sequencing using the ionTorrent® technology, decoding, and input normalization as described in FIG. 10 C, D. The pulldown efficiencies, representing extent of acetylation at that particular site, are expressed in % input. (C) Detection of histone writing activity of a nuclear cell lysate derived from human 293T cells. The barcoded library was incubated with a nuclear cell extract in the presence of 20 μM AcCoA, 10 μM S-adenosine methionine (SAM), and 10 μM adenosine triphosphate (ATP), and the reaction product was isolated using an antibody specific for the H3K14ac mark. This was followed by DNA isolation, purification, multiplexing using the reverse experimental multiplex barcodes, sequencing using the ionTorrent® technology, decoding, and input normalization as described in FIG. 10 C, D.
Figure 16B:
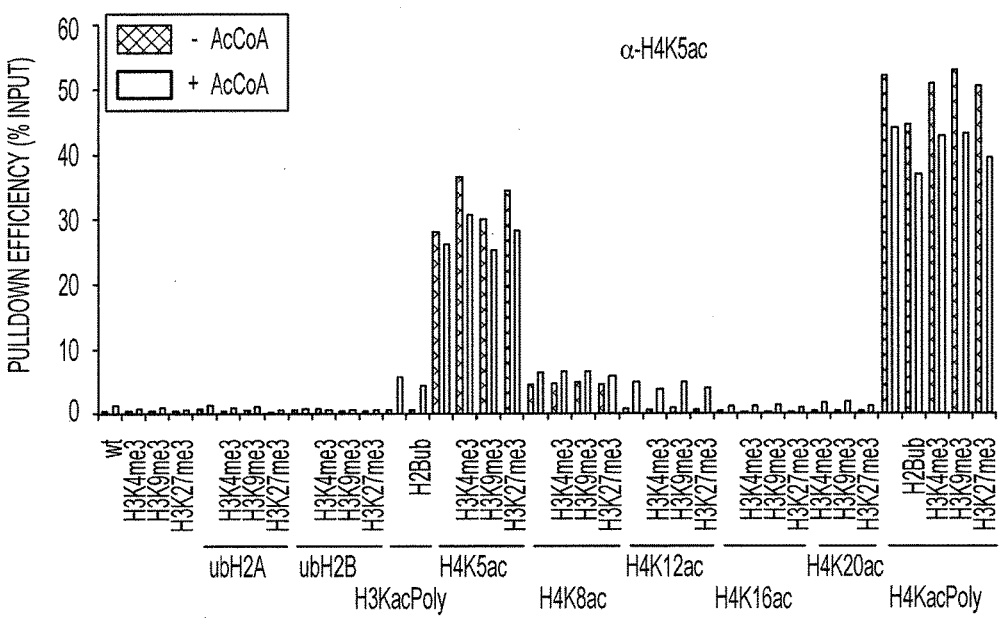
Figure 16C:
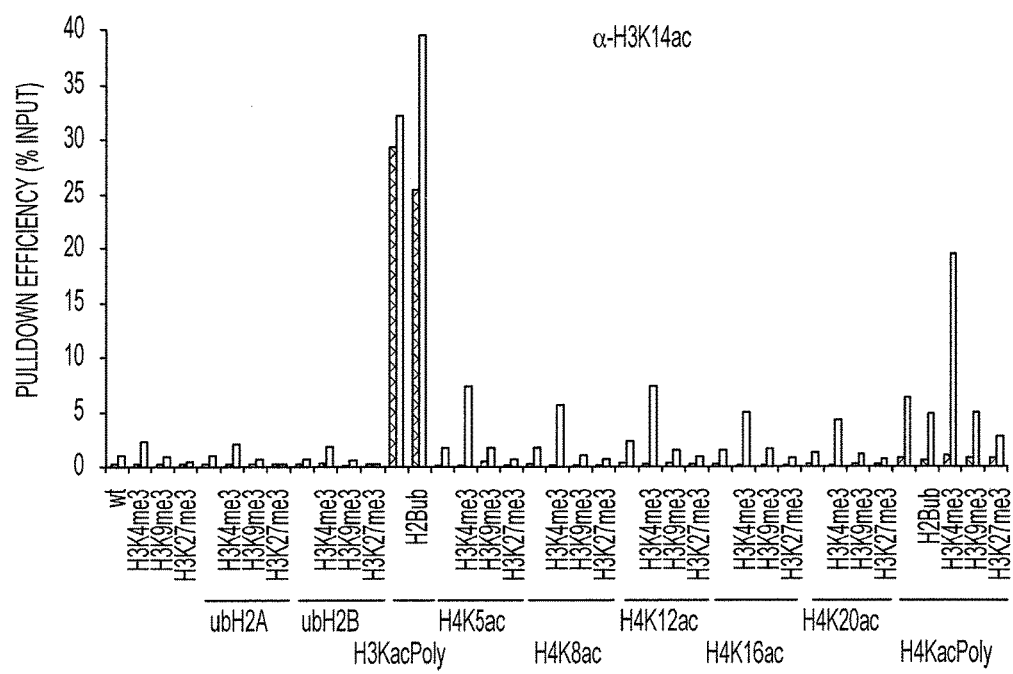

Profiling of a recombinantly expressed histone writer, the histone acetyltransferase p300: The encoded nucleosomes (at a concentration of 30 nM) were incubated with 3 nM of recombinant full-length human p300, prepared in Sf9 insect cells, in the absence or presence of 10 µM AcCoA for 1 h at 30° C. in histone acetyltransferase (HAT) buffer (50 mM Tris, pH 8.0, 0.1 mM EDTA, 1 mM PMSF, 10 mM Na-butyrate, 10% glycerol, 1 mM DTT). The reaction products, or subsets thereof, were isolated by immunoprecipitation using antibodies specific for H4K5ac and H3K18ac (FIG. 16 a and b). In brief, 15 µL of the reaction were supplemented with the respective antibody (i.e. 12 fmoles of each MN variant per reaction and antibody pulldown), in this case α-H3K18ac or α-H4K5ac antibodies, adjusted to a total volume of 100 µL AB buffer to give a final antibody concentration of 15 µg/mL, and incubated for 1 h at RT on an end-to-end rotator. Subsequently, 100 µL AB buffer as well as 10 µL of a protein G bead slurry were added and incubated on an end-to-end rotator for 1.5 h at RT. The beads were washed 4 times with 200 µL AB buffer. Antibody pulldown, DNA isolation, purification, multiplexing, decoding, and normalization were performed as described above. When the library was treated with AcCoA and immunoprecipitated with α-H3K18ac, an increase in pulldown from 0.3% to about 4% input was observed for wt nucleosomes, which reflected an increase in lysine acetylation at that site caused by p300 (FIG. 16a). The extent of acetylation was not influenced by the existence of Kme3 or Kub marks. However, significantly stronger H3 acetylation (FIG. 16a, 13-fold compared to wt) was found on nucleosomes poly-acetylated in the H4 tail, which is in line with our library binding data (FIG. 15a). Interestingly, as little as one Kac mark on H4 could recapitulate this H4Kac to H3Kac cross-talk, albeit with lower efficiency. This effect was dependent on the exact position of the mark within the tail and was most pronounced for H4K12ac (FIG. 16a). In order to test whether this cross-talk existed in the reverse direction, we immunoprecipitated the reaction mixture with an α-H4K5ac antibody (FIG. 16b). A small increase in acetylation was observed for wt nucleosomes in the presence of AcCoA (0.5 to 0.9% input), which was not influenced by Kub or Kme3 modifications (FIG. 16b, right). In contrast, H3Kac$_5$-containing nucleosomes were modified more readily (FIG. 16b, 6-fold increase compared to wt), suggesting an inter-tail cross-talk from H3Kac to H4Kac as well. Additionally, nucleosomes with pre-existing K12ac marks led to an elevated pulldown efficiency (4.4% input, FIG. 16b, right), proposing an additional intra-tail cross-talk within the H4 tail. However, this increase could also be a result of a higher antibody affinity for poly-acetylated, compared to mono-acetylated, nucleosomes. Our experiments show that p300 operates via a positive feedback mechanism through position-dependent, Kac-mediated inter-tail and potentially intra-tail cross-talks. Therefore, we probed these new findings with traditional single modified nucleosomes containing preinstalled Kac marks within the H3 or H4 tail with antibody-independent methods, such as radioactive gel-based enzyme assays and mass spectrometry, which confirmed the library screening results.

Example 3

Profiling of histone readers, writers, and erasers of a nuclear cell extract derived from human 293T cells: To investigate the epigenetic signature of a given cell line, barcoded nucleosome library was profiled with a nuclear extract derived from human 293T cells prepared as described earlier (Dignam, Lebovitz, & Roeder, 1983). 15 µL of the encoded nucleosome library (at a concentration of 30 nM, i.e. 12 fmoles of each MN variant per reaction and antibody pulldown)) was incubated with 7.5 µL of the nuclear extract in the presence of 20 µM AcCoA, 10 µM SAM, and 10 µM ATP for 1 h at 30° C. in HAT buffer. Nucleosomes that were acetylated at H3K14 as a result of the acetyltransferase activities of the endogenous HATs in the nuclear extract were isolated using an α-H3K14ac antibody. Antibody pulldown, DNA isolation, purification, multiplexing, decoding, and normalization were performed as described above. Increase in H3K14 acetylation of an uncharacterized HAT, potentially p300, was observed for wt nucleosomes. The extent of acetylation was significantly increased for those MN variants carrying a pre-installed H3K4me3 and/or single of multiple Kac marks within the H4 tail (FIG. 16c), suggesting enzymatic cross-talks between histone writers, erasers, and/or readers. These results are intriguing since they demonstrate that this experimental procedure can be exploited as a rapid and efficient diagnostic tool to investigate the epigenetic signature of a given cell line, including those derived from human cancer patients.

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding preferred specific embodiments are to be construed as merely illustrative, and not limiting of the scope of the invention in any way whatsoever. The entire disclosure of all applications, patents, and publications cited above, including U.S. Provisional Application 61/656,233, filed Jun. 6, 2012, and U.S. Provisional Application 61/712,148, filed Oct. 10, 2012, are hereby incorporated by reference in their entirety, particularly with regard to the disclosure for which they are cited in the application.

REFERENCES

Agasti, S. S., Liong, M., Peterson, V. M., Lee, H., & Weissleder, R. (2012). Photocleavable DNA Barcode—Antibody Conjugates Allow Sensitive and Multiplexed Protein Analysis in Single Cells. *Journal of the American Chemical Society*, 134(45), 18499-18502. doi:10.1021/ja307689w Allis, C. D., & Muir, T. W. (2011). Spreading chromatin into chemical biology. *Chembiochem: a European journal of chemical biology*, 12(2), 264-279. doi:10.1002/cbic.201000761

Bao, Y., Chakravarthy, S., Muthurajan, U. M., & Luger, K. (2003). Reconstitution of nucleosome core particles from recombinant histones and DNA . . . *in enzymology*.

Blacketer, M. J., Feely, S. J., & Shogren-Knaak, M. A. (2010). Nucleosome interactions and stability in an ordered nucleosome array model system. *The Journal of biological chemistry*, 285(45), 34597-34607. doi:10.1074/jbc.M110.140061

Britton, L.-M. P., Gonzales-Cope, M., Zee, B. M., & Garcia, B. A. (2011). Breaking the histone code with quantitative mass spectrometry. *Expert review of proteomics*, 8(5), 631-643. doi:10.1586/epr.11.47

Buller, F., Mannocci, L., & Scheuermann, J. (2010). Drug discovery with DNA-encoded chemical libraries. *Bioconjugate* . . . .

Cao, Y., Korolev, N., & Nordenskiöld, L. (2011). A Direct Method for Site-Specific Protein Acetylation. *Angewandte Chemie* . . . .

Clark, M. A. (2010). Selecting chemicals: the emerging utility of DNA-encoded libraries. *Current Opinion in Chemical Biology*, 14(3), 396-403. doi:10.1016/j.cbpa.2010.02.017

Dai, J., Hyland, E. M., Yuan, D. S., Huang, H., & Bader, J. S. (2008). Probing nucleosome function: a highly versatile library of synthetic histone H3 and H4 mutants. *Cell*.

Dawson, P. E., & Kent, S. B. (2000). Synthesis of native proteins by chemical ligation. *Annual Review of Biochemistry*, 69, 923-960. doi:10.1146/annurev.biochem.69.1.923

Dignam, J. D., Lebovitz, R. M., & Roeder, R. G. (1983). Accurate transcription initiation by RNA polymerase II in a soluble extract from isolated mammalian nuclei. *Nucleic Acids Research*.

Dyer, P. N., Edayathumangalam, R. S., White, C. L., Bao, Y., Chakravarthy, S., Muthurajan, U. M., & Luger, K. (2004). Reconstitution of nucleosome core particles from recombinant histones and DNA. *Methods in enzymology*, 375, 23-44.

ENCODE Project Consortium, Dunham, I., Kundaje, A., Aldred, S. F., Collins, P. J., Davis, C. A., et al. (2012). An integrated encyclopedia of DNA elements in the human genome. *Nature*, 489(7414), 57-74. doi:10.1038/nature11247

Fierz, B., & Muir, T. W. (2012). Chromatin as an expansive canvas for chemical biology. *Nature chemical biology*, 8(5), 417-427. doi:10.1038/nchembio.938

Fierz, B., Chatterjee, C., McGinty, R. K., Bar-Dagan, M., Raleigh, D. P., & Muir, T. W. (2011). Histone H2B ubiquitylation disrupts local and higher-order chromatin compaction. *Nature chemical biology*, 7(2), 113-119. doi:10.1038/nchembio.501

Fierz, B., Kilic, S., Hieb, A. R., Luger, K., & Muir, T. W. (2012). Stability of Nucleosomes Containing Homogenously Ubiquitylated H2A and H2B Prepared Using Semisynthesis. *Journal of the American Chemical Society*, 134(48), 19548-19551. doi:10.1021/ja308908p Flaus, A., & Richmond, T. J. (1998). Positioning and stability of nucleosomes on MMTV 3'LTR sequences. *Journal of Molecular Biology*, 275(3), 427-441. doi:10.1006/jmbi.1997.1464

Garske, A. L., Oliver, S. S., Wagner, E. K., Musselman, C. A., LeRoy, G., Garcia, B. A., et al. (2010). Combinatorial profiling of chromatin binding modules reveals multisite discrimination. *Nature Methods*, 6(4), 283-290. doi:10.1038/nchembio.319

Goldman, J. A., Garlick, J. D., & Kingston, R. E. (2010). Chromatin remodeling by imitation switch (ISWI) class ATP-dependent remodelers is stimulated by histone variant H2A.Z. *The Journal of biological chemistry*, 285(7), 4645-4651. doi:10.1074/jbc.M109.072348

Heller, M. J. (2002). DNA microarray technology: devices, systems, and applications. *Annual review of biomedical engineering,* 4, 129-153. doi:10.1146/annurev.bioeng.4.020702.153438

Kleer, C. G., Cao, Q., Varambally, S., Shen, R., Ota, I., Tomlins, S. A., et al. (2003). EZH2 is a marker of aggressive breast cancer and promotes neoplastic transformation of breast epithelial cells. *Proceedings of the National Academy of Sciences,* 100(20), 11606-11611. doi:10.1073/pnas.1933744100

Kleiner, R. E., Dumelin, C. E., & Liu, D. R. (2011). Small-molecule discovery from DNA-encoded chemical libraries. *Chemical Society Reviews.*

Krutzik, P. O., & Nolan, G. P. (2006). Fluorescent cell barcoding in flow cytometry allows high-throughput drug screening and signaling profiling. *Nature Methods,* 3(5), 361-368. doi:10.1038/nmeth872

Lowary, P. T., & Widom, J. (1998). New DNA sequence rules for high affinity binding to histone octamer and sequence-directed nucleosome positioning. *Journal of Molecular Biology,* 276(1), 19-42. doi:10.1006/jmbi.1997.1494

Luger, K., Rechsteiner, T. J., & Richmond, T. J. (1999). Preparation of nucleosome core particle from recombinant histones. *Methods in enzymology,* 304, 3-19.

Mardis, E. R. (2008). Next-generation DNA sequencing methods. *Annual review of genomics and human genetics,* 9, 387-402. doi:10.1146/annurev.genom.9.081307.164359

Merriman, B., R D Team, I. T., & Rothberg, J. M. (2012). Progress in Ion Torrent semiconductor chip based sequencing. *Electrophoresis,* 33(23), 3397-3417. doi:10.1002/elps.201200424

Muir, T. W. (2003). Semisynthesis of proteins by expressed protein ligation. *Annual Review of* Biochemistry, 72, 249-289. doi:10.1146/annurev.biochem.72.121801.161900

Rothberg, J. M., Hinz, W., Rearick, T. M., Schultz, J., Mileski, W., Davey, M., et al. (2011). An integrated semiconductor device enabling non-optical genome sequencing. *Nature,* 475(7356), 348-352. doi:10.1038/nature10242

Ruthenburg, A. J., Li, H., Milne, T. A., Dewell, S., McGinty, R. K., Yuen, M., et al. (2011). Recognition of a Mononucleosomal Histone Modification Pattern by BPTF via Multivalent Interactions. *Cell,* 145(5), 692-706. doi:10.1016/j.cell.2011.03.053

Schones, D. E., & Zhao, K. (2008). Genome-wide approaches to studying chromatin modifications. *Nature reviews. Genetics,* 9(3), 179-191. doi:10.1038/nrg2270

Simon, M. D., Chu, F., Racki, L. R., la Cruz, de, C. C., Burlingame, A. L., Panning, B., et al. (2007). The site-specific installation of methyl-lysine analogs into recombinant histones. *Cell,* 128(5), 1003-1012. doi:10.1016/j.cell.2006.12.041

Spacil, Z., Tatipaka, H., Barcenas, M., Scott, C. R., Turecek, F., & Gelb, M. H. (2013). High-throughput assay of 9 lysosomal enzymes for newborn screening. *Clinical chemistry,* 59(3), 502-511. doi:10.1373/clinchem.2012.189936

Wang, L., Xie, J., & Schultz, P. G. (2006). Expanding the genetic code. *Annual review of biophysics and biomolecular structure.*

Weibel, D. B., & Whitesides, G. M. (2006). Applications of microfluidics in chemical biology. *Current Opinion in Chemical Biology.*

Whitesides, G. M. (2006). The origins and the future of microfluidics. *Nature,* 442(7101), 368-373. doi:10.1038/nature05058

]Peterson et al., U.S. Pat. No. 5,972,608, "Assays and Reagents for Chromatin Remodeling Enzymes and their Modulators."

Steinman et al., US 2009/0062130, "Nucleosome-Based Biosensor."

---

We claim:

1. A method for identifying one or more modifications associated with one or more chromatin interactors or modifiers, comprising dividing a library of synthetic mononucleosomes into one or more sublibraries;

incubating the one or more chromatin interactors and/or modifiers with the one or more sublibraries;

isolating one or more unique DNA barcodes from one or more modified mononucleosomes associated with one or more chromatin interactors or modifiers;

multiplexing the isolated DNA barcodes by furnishing each isolated DNA sequence with an additional DNA barcode corresponding to the one or more chromatin interactors or modifiers via polymerase chain reaction; and identifying the one or more modifications associated with each of the one or more chromatin interactors or modifiers through barcode detection via polymerase chain reaction or DNA sequencing, wherein the library of synthetic mononucleosomes comprises two or more synthetic mononucleosomes, wherein each of the two or more synthetic mononucleosomes comprises a complex of:

(a) a protein octamer, comprising 2 copies of each of histones H2A, H2B, H3, and H4 and optionally a linker histone, wherein at least one of the histones is unmodified and/or wherein at least one of the histones is modified, to form a pattern of histone modifications, and (b) a nucleosomal DNA molecule, comprising (i) a nucleosome positioning sequence (NPS), wherein the nucleosome positioning sequence is a nucleotide sequence that forms a stable protein association with one or more of the histones, (ii) one or more unique DNA barcode sequence(s) located at defined position(s) in the nucleosomal DNA, and (iii) one or more DNA extensions, on the 5'- and/or 3'-end of the NPS and/or within the NPS, wherein the DNA extensions are unmodified and/or wherein at least one nucleotide in the DNA extensions is modified, to form a pattern of DNA modifications, and optionally (c) one or more non-histone chromatin-associated proteins, wherein for each of the two or more synthetic mononucleosomes the pattern of histone modifications and the pattern of DNA modifications form a pattern of mononucleosome modifications, and wherein for each of the two or more synthetic mononucleosomes the sequence and position of the one or more unique DNA barcode sequence(s) in the nucleosomal DNA is indicative of the pattern of mononucleosome modifications in the synthetic mononucleosome.

2. A method for assembling a synthetic mononucleosome, comprising combining one or more modified histone proteins, complementary unmodified histones and one or more barcoded nucleosomal DNA with an affinity-tagged buffer DNA, in a predetermined ratio, wherein the synthetic mononucleosome comprises a complex of:

(a) a protein octamer, comprising 2 copies of each of histones H2A, H2B, H3, and H4 and optionally a linker histone, wherein at least one of the histones is unmodified and/or wherein at least one of the histones is modified, to form a pattern of histone modifications, and
(b) a nucleosomal DNA molecule, comprising
  (i) a nucleosome positioning sequence (NPS), wherein the nucleosome positioning sequence is a nucleotide sequence that forms a stable protein association with one or more of the histones,
  (ii) one or more DNA barcode sequence(s) located at defined position(s) in the nucleosomal DNA, and
  (iii) one or more DNA extensions, on the 5'- and/or 3'-end of the NPS and/or within the NPS, wherein the DNA extensions are unmodified and/or wherein at least one nucleotide in the DNA extensions is modified, to form a pattern of DNA modifications, and optionally
(c) one or more non-histone chromatin-associated proteins,
wherein for the synthetic mononucleosome the pattern of histone modifications and the pattern of DNA modifications form a pattern of nucleosome modifications, and
wherein for the synthetic mononucleosome the sequence and position of the one or more DNA barcode sequence(s) in the nucleosomal DNA is indicative of the pattern of nucleosome modifications in the synthetic mononucleosome.

3. A method for determining the specificity of the recognition patterns and affinities of one or more chromatin readers which are of recombinant origin and/or extracted from nuclear cell extracts, or for determining the specificity and chromatin modification cross-talks of one or more chromatin modifiers which are of recombinant origin and/or extracted from nuclear cell extracts of one or more cell lines, comprising
  (i) contacting one or more synthetic mononucleosomes with the one or more chromatin readers or the one or more chromatin modifiers,
  (ii) isolating bound and/or modified synthetic mononucleosomes, and
  (iii) identifying and/or quantitating the bound or modified synthetic mononucleosomes and any added marks or removed marks,
  wherein the identifying and/or quantitating the bound or modified synthetic mononucleosomes comprises the use of quantitative polymerase chain reaction or next generation sequencing,
  wherein each of the one or more synthetic mononucleosomes comprises a complex of:
    (a) a protein octamer, comprising 2 copies of each of histones H2A, H2B, H3, and H4 and optionally a linker histone, wherein at least one of the histones is unmodified and/or wherein at least one of the histones is modified to form a pattern of histone modifications, and
    (b) a nucleosomal DNA molecule, comprising
      (i) a nucleosome positioning sequence (NPS), wherein the nucleosome positioning sequence is a nucleotide sequence that forms a stable protein association with one or more of the histones,
      (ii) one or more DNA barcode sequence(s) located at defined position(s) in the nucleosomal DNA, and
      (iii) one or more DNA extension(s), on the 5'- and/or 3'-end of the NPS and/or within the NPS, wherein the DNA extension(s) are unmodified and/or wherein at least one nucleotide in the DNA extension(s) is modified, to form a pattern of DNA modifications, and optionally
    (c) one or more non-histone chromatin-associated protein(s),
    wherein for each of the one or more synthetic mononucleosomes the pattern of histone modifications and the pattern of DNA modifications form a pattern of nucleosome modifications, and
    wherein for each of the one or more synthetic mononucleosomes the sequence and position of the one or more DNA barcode sequence(s) in the nucleosomal DNA is indicative of the pattern of nucleosome modifications in the mononucleosome.

4. The method of claim 2, wherein the buffer DNA is MMTV.

5. The method of claim 1, wherein each of the two or more synthetic mononucleosomes comprises a linker histone.

6. The method of claim 1, wherein at least one of the two or more synthetic mononucleosomes comprises a linker histone.

7. The method of claim 1, wherein each of the two or more synthetic mononucleosomes comprises one or more non-histone chromatin-associated proteins.

8. The method of claim 1, wherein at least one of the two or more synthetic mononucleosomes comprises one or more non-histone chromatin-associated proteins.

9. The method of claim 2, wherein the synthetic mononucleosome comprises a linker histone.

10. The method of claim 2, wherein the synthetic mononucleosome comprises one or more non-histone chromatin-associated proteins.

11. The method of claim 3, wherein each of the one or more synthetic mononucleosomes comprises a linker histone.

12. The method of claim 3, wherein at least one of the one or more synthetic mononucleosomes comprises a linker histone.

13. The method of claim 3, wherein each of the one or more synthetic mononucleosomes comprises one or more non-histone chromatin-associated protein(s).

14. The method of claim 3, wherein at least one of the one or more synthetic mononucleosomes comprises one or more non-histone chromatin-associated protein(s).

15. A method for determining the specificity of the recognition patterns and affinities of one or more chromatin readers which are of recombinant origin and/or extracted from nuclear cell extracts, or for determining the specificity and chromatin modification cross-talks of one or more chromatin modifiers which are of recombinant origin and/or extracted from nuclear cell extracts of one or more cell lines, comprising
  (i) contacting one or more synthetic polynucleosome(s) with the one or more chromatin readers or the one or more chromatin modifiers,
  (ii) isolating bound and/or modified synthetic polynucleosome(s), and
  (iii) identifying and/or quantitating the bound or modified synthetic polynucleosome(s) and any added marks or removed marks,
  wherein the identifying and/or quantitating the bound or modified synthetic polynucleosome(s) comprises the use of quantitative polymerase chain reaction or next generation sequencing,
  wherein each of the one or more synthetic polynucleosome(s) comprises two or more synthetic mononucleosomes bonded together by a defined DNA molecule, the two or more bonded synthetic mononucleosomes having a defined connectivity, wherein each of the two or more bonded synthetic mononucleosomes comprises a complex of
  (a) a protein octamer, comprising 2 copies of each of histones H2A, H2B, H3, and H4, and optionally a linker histone, wherein at least one of the histones is unmodified and/or wherein at least one of the histones is modified to form a pattern of mononucleosomal histone modifications, and
  (b) a mononucleosomal DNA molecule, comprising
    (i) a nucleosome positioning sequence (NPS), and
    (ii) one or more DNA extension(s), on the 5'- and/or 3'-end of the NPS and/or within the NPS, wherein the DNA extension(s) are unmodified and/or wherein at least one nucleotide in the DNA extension(s) is modified, to form a pattern of mononucleosomal DNA modifications, and optionally
  (c) one or more non-histone chromatin-associated protein(s), wherein in each of the synthetic polynucleosomes the two or more synthetic mononucleosomes are bonded together by bonding of their respective mononucleosomal DNA molecules, wherein the pattern of mononucleosomal histone modifications and the pattern of mononucleosomal DNA modifications throughout each synthetic polynucleosome comprising two or more bonded mononucleosomes may be uniform or may be different, resulting in a pattern of polynucleosomal modifications, and wherein each synthetic polynucleosome comprises one or more DNA barcode sequence(s) located at defined position(s) in the mononucleosomal DNA of at least one of the two or more bonded mononucleosomes and whose sequence and position in the mononucleosomal DNA is indicative of the pattern of polynucleosomal modifications.

16. The method of claim 15, wherein each of the two or more bonded synthetic mononucleosomes comprises a linker histone.

17. The method of claim 15, wherein at least one of the two or more bonded synthetic mononucleosomes comprises a linker histone.

18. The method of claim 15, wherein each of the two or more bonded synthetic mononucleosomes comprises one or more non-histone chromatin-associated protein(s).

19. The method of claim 15, wherein at least one of the two or more bonded synthetic mononucleosomes comprises one or more non-histone chromatin-associated protein(s).

* * * * *